US00RE39198E

(19) United States
(12) Reissued Patent
Strupczewski et al.

(10) Patent Number: US RE39,198 E
(45) Date of Reissued Patent: Jul. 18, 2006

(54) HETEROARYLPIPERIDINES, PYRROLIDINES AND PIPERAZINES AND THEIR USE AS ANTIPSYCHOTICS AND ANALGESICS

(75) Inventors: Joseph T. Strupczewski, Flemington, NJ (US); Grover C. Helsley, Rosemont, NJ (US); Yulin Chiang, Convent Station, NJ (US); Kenneth J. Bordeau, Kintnersville, PA (US); Edward J. Glamkowski, Warren, NJ (US)

(73) Assignee: Aventis Pharmaceuticals Inc., Bridgewater, NJ (US)

(21) Appl. No.: 09/712,129

(22) Filed: Nov. 15, 2000

Related U.S. Patent Documents

Reissue of:
(64) Patent No.: 5,364,866
Issued: Nov. 15, 1994
Appl. No.: 07/969,383
Filed: Oct. 30, 1992

U.S. Applications:
(63) Continuation-in-part of application No. 07/788,269, filed on Nov. 5, 1991, now abandoned, which is a continuation-in-part of application No. 07/944,705, filed on Sep. 5, 1991, now abandoned, which is a continuation of application No. 07/619,825, filed on Nov. 29, 1990, now abandoned, which is a continuation of application No. 07/456,790, filed on Dec. 29, 1989, now abandoned, which is a continuation-in-part of application No. 07/354,411, filed on May 19, 1989, now abandoned.

(51) Int. Cl.
*A61K 31/445* (2006.01)
*A61K 31/495* (2006.01)
*A61K 31/42* (2006.01)
*C07D 211/00* (2006.01)

(52) U.S. Cl. ..... 514/321; 514/254.02; 514/254.06; 514/318; 514/322; 514/373; 514/379; 514/403; 544/257; 544/366; 544/368; 546/194; 546/198; 546/199; 546/270.1; 546/271.7; 548/207; 548/356.5

(58) Field of Classification Search ..... 514/318, 514/321, 322; 546/194, 198, 199
See application file for complete search history.

(56) References Cited

U.S. PATENT DOCUMENTS

| | | | | | |
|---|---|---|---|---|---|
| 3,950,527 | A | | 4/1976 | Derible et al. | 424/267 |
| 4,355,037 | A | * | 10/1982 | Strupczewski et al. | 546/198 |
| 4,458,076 | A | * | 7/1984 | Strupczewski | 546/199 |
| 4,590,196 | A | * | 5/1986 | Smith et al. | 514/253 |
| 4,670,447 | A | * | 6/1987 | Strupczewski | 514/322 |
| 4,745,117 | A | | 5/1988 | Ishizumi | 514/254 |
| 4,780,466 | A | | 10/1988 | Hrib et al. | 514/254 |
| 4,880,930 | A | | 11/1989 | New | 544/295 |
| 4,937,249 | A | * | 6/1990 | Antoku et al. | 514/321 |
| 4,954,503 | A | * | 9/1990 | Strupczewski et al. | 514/254 |
| 4,968,792 | A | | 11/1990 | Stack et al. | 540/524 |
| 4,999,356 | A | * | 3/1991 | Strupczewski | 514/254 |
| 5,001,134 | A | * | 3/1991 | Ferrand et al. | 514/321 |
| 5,364,866 | A | | 11/1994 | Strupczewski et al. | 514/321 |

FOREIGN PATENT DOCUMENTS

| | | | |
|---|---|---|---|
| DE | 353 0089 | | 3/1986 |
| DK | 2 503 816 | | 7/1975 |
| EP | 0 261 688 | | 3/1980 |
| EP | 0 013 612 | | 7/1980 |
| EP | 0 135 781 | * | 4/1985 |
| EP | 0 196 096 | * | 10/1986 |
| EP | 0 302 423 | | 2/1989 |
| EP | 0 314 098 | * | 5/1989 |
| EP | 0 329 168 | | 8/1989 |
| EP | 0 353 821 | | 2/1990 |
| EP | 0 357 134 | | 3/1990 |
| EP | 0 398 425 | * | 11/1990 |
| EP | 0 402 644 | * | 12/1990 |
| EP | 0 464 846 | | 1/1992 |
| EP | 0 542 136 | | 5/1993 |
| GB | 2 163 432 | * | 2/1986 |
| NZ | 233 710 | | 5/1990 |
| NZ | 233 503 | | 6/1991 |
| NZ | 233 525 | | 9/1991 |
| WO | WO93/09012 | | 5/1993 |
| WO | WO 93/16073 | | 8/1993 |
| WO | WO94/18196 | | 8/1994 |

OTHER PUBLICATIONS

Fuller, R.W., Drugs Acting on Serotonergie Neuronal Systems, Biology of Serotonergic Transmission, John Wiley & Sons Ltd., 1982, pp. 221–247.

* cited by examiner

*Primary Examiner*—Brenda Coleman
(74) *Attorney, Agent, or Firm*—Synnestvedt & Lechner LLP

(57) ABSTRACT

Heteroarylpiperidines, pyrrolidines, and piperazines are useful as antipsychotic and analgesic agents. The compounds are especially useful for treating psychoses by administering to a mammal a psychoses-treating effective amounts of one of the compounds. The compounds are also useful as analgesics by administering a pain-relieving effective amount of one of the compounds to a mammal.

146 Claims, No Drawings

HETEROARYLPIPERIDINES, PYRROLIDINES AND PIPERAZINES AND THEIR USE AS ANTIPSYCHOTICS AND ANALGESICS

Matter enclosed in heavy brackets [ ] appears in the original patent but forms no part of this reissue specification; matter printed in italics indicates the additions made by reissue.

CROSS-REFERENCE TO RELATED APPLICATION

This application is a continuation-in-part of application Ser. No. 788,269, filed Nov. 5, 1991 (Attorney Docket No. 02489-0028-03000), now abandoned, which is a continuation-in-part of application Ser. No. 944,705, filed Sep. 5, 1991 (Attorney Docket No. 02489-0028-04000), now abandoned, which is a continuation of application Ser. No. 619,825, filed Nov. 29, 1990 (Attorney Docket No. 02489-0028-02000), now abandoned, which is a continuation of application Ser. No. 456,790, filed Dec. 29, 1989 (Attorney Docket No. 02489-0028-01000), now abandoned, which is a continuation-in-part of application Ser. No. 354,411, filed May 19, 1989, (Attorney Docket Nos. 02489-0028-00000 and HR-1161), now abandoned. The entire disclosure of these applications is relied upon and incorporated by reference herein.

BACKGROUND OF THE INVENTION

This invention relates to heteroarylpiperidines, pyrrolidines and piperazines. More particularly, this invention relates to heteroarylpiperidines, pyrrolidines and piperazines having antipsychotic activity and to their use as antipsychotic drugs.

The therapeutic treatment of schizophrenic patients by administration of neuroleptic drugs, such as chlorpromazine, haloperidol, sulpiride, and chemically closely related compounds, is widespread. While control of schizophrenic symptoms has been successful, treatment with these drugs does not cure the psychotic patient, who will almost certainly relapse if medication is discontinued. There exists a continuing need in the art for antipsychotic drugs for the treatment of psychoses.

Moreover, some of the known neuroleptics produce unwanted side effects. For example, the side effects of many antipsychotic drugs include the so-called extrapyramidal symptoms, such as rigidity and tremor, continuous restless walking, and tardive dyskinesia which causes facial grimacing, and involuntary movements of the face and extremities. Orthostatic hypotension is also common. Thus, there also exists a need in the art for antipsychotic drugs that produce fewer or less severe manifestations of these common side effects.

Moreover, there has been a need for drugs that can produce other biological effects. For example, relief from pain has been an age-old aspiration which has led to the discovery of natural and synthetic analgetics. Nevertheless, the need for safe and effective analgetics has continued to the present day.

SUMMARY OF THE INVENTION

This invention aids in fulfilling these needs in the by providing a compound of the formula:

(I)

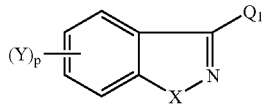

wherein

X is —O—, —S—,

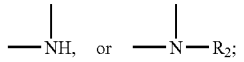

$R_2$ is selected from the group consisting of lower alkyl, aryl lower alkyl, aryl, cycloalkyl, aroyl, alkanoyl, and phenylsulfonyl groups;

p is 1 or 2;

Y is hydrogen, lower alkyl, hydroxy, chlorine, fluorine, bromine, iodine, lower alkoxy, trifluoromethyl, nitro, or amino, when p is 1;

Y is lower alkoxy, hydroxy and halogen when p is 2 and X is —O—;

$Q_1$ is selected from the group consisting of:

(a)

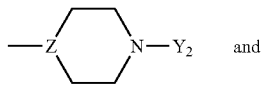

(b)

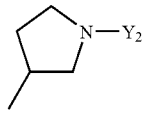

where Z is

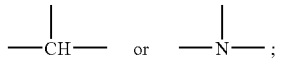

and $Y_2$ is selected from the group consisting of:

(1)

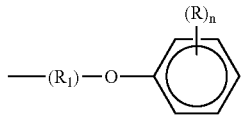

in which $(R_1)$ is $—(CH_2)_n—$ where n is 2, 3, 4, or 5; or $—CH_2—CH═CH—CH_2—$, $—CH_2—C≡C—CH_2—$, $—CH_2—CH═CH—CH_2—CH_2—$, $—CH_2—CH_2—CH═CH—CH_2—$, $—CH_2—C≡C—CH_2—CH_2—$, or $—CH_2—CH_2—C═C—CH_2—$, the —CH═CH— bond being cis or trans; and R and m are as defined hereinafter;

(2)

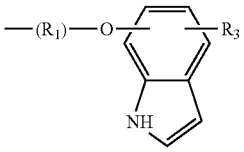

where $R_3$ is H or —$OCH_3$ and n has the above meaning;

(3)

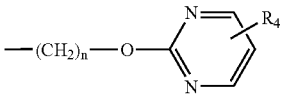

$R_4$ is hydrogen, lower alkyl, lower alkoxy, amino, mono- or dialkylamino, $C_1$–$C_3$ acyl amino, $C_1$–$C_6$ alkanoyl, trifluoromethyl, chlorine, fluorine, bromine,

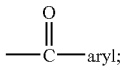

in which aryl is phenyl or

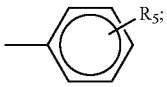

where $R_5$ is hydrogen, lower alkyl, lower alkoxy, hydroxy, chlorine, fluorine, bromine, iodine, lower monoalkylamino, lower dialkylamino, nitro, cyano, trifluoromethyl, trifluoromethoxy;

where n has the above meaning;

(4)

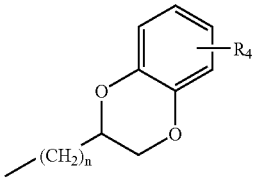

where n and $R_4$ are as previously defined;

(5)

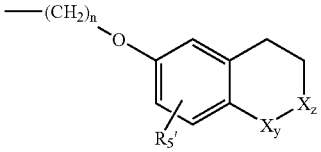

where either one of $X_y$ or $X_z$ is

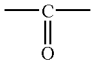

and the other is —$CH_2$—;

and $R_5'$ is hydrogen, lower alkyl, lower alkoxy, chlorine, fluorine, or bromine; and (6)

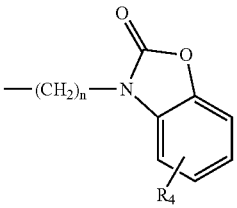

where n and $R_4$ are as previously defined;

(7)

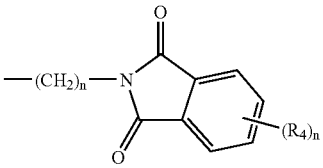

where n and $R_4$ are as previously defined;

(8)

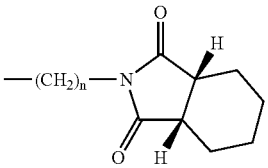

where n is as previously defined;

(9)

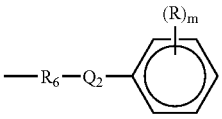

where $Q_2$ is S, NH, or —$CH_2$—;

$R_6$ is the same as $R_1$ when $Q_2$ is S or NH; and when $Q_2$ is —$CH_2$—, $R_6$ is selected from the group consisting of:

—$CH_2$—$CH_2$—
—$CH_2$—$CH_2$—$CH_2$—
—$CH_2$—$CH_2$—$CH_2$—$CH_2$—
—$CH_2$—CH═CH—$CH_2$—
—$CH_2$—$CH_2$—CH═CH—
—$CH_2$—CH═CH—$CH_2$—
—$CH_2$—$CH_2$—CH═CH—
—$CH_2$—CH═CH—$CH_2$—$CH_2$—
—$CH_2$—$CH_2$—CH═CH—$CH_2$—
—$CH_2$—$CH_2$—$CH_2$—CH═CH—
—$CH_2$—CH═CH—$CH_2$—$CH_2$—
—$CH_2$—$CH_2$—CH═CH—$CH_2$—
—$CH_2$—$CH_2$—$CH_2$—CH═CH—
—$CH_2$—C≡C—$CH_2$
—$CH_2$—$CH_2$—C≡C—
—$CH_2$—C≡C—$CH_2$—$CH_2$—
—$CH_2$—$CH_2$—C≡C—$CH_2$—
—$CH_2$—$CH_2$—$CH_2$—$CH_2$—C≡C— the —CH═CH— bone being cis or trans;

R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, dialkylaminocarbonyl, formyl,

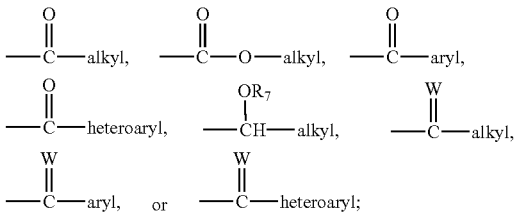

alkyl is lower alkyl;

aryl is as previously defined;

heteroaryl is

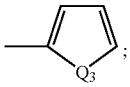

$Q_3$ is —O—, —S—, —NH, —CH═N;

W is $CH_2$ or $CHR_8$ or N—$R_9$;

$R_7$ is hydrogen, lower alkyl, or acyl;

$R_8$ is lower alkyl;

$R_9$ is hydroxy, lower alkoxy, or —$NHR_{10}$; and $R_{10}$ is hydrogen, lower alkyl, $C_1$–$C_3$ acyl, aryl,

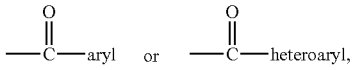

where aryl and heteroaryl are as defined above; and m is 1, 2, or 3;

or a pharmaceutically acceptable acid addition salt thereof.

This invention also aids in fulfilling these needs the art by providing a compound of the formula:

(I)

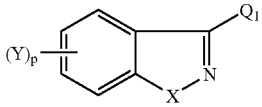

wherein

X is —O—, —S—,

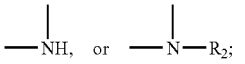

$R_2$ is selected from the group consisting of lower alkyl, aryl lower alkyl, aryl, cycloalkyl, aroyl, alkanoyl, and phenylsulfonyl groups;

p is 1 or 2;

Y is hydrogen, lower alkyl, hydroxy, chlorine, fluorine, bromine, iodine, lower alkoxy, trifluoromethyl, nitro, or amino, when p is 1;

Y is lower alkoxy, hydroxy and halogen when p is 2 and X is —O—;

$Q_1$ is selected from the group consisting of:

(a)

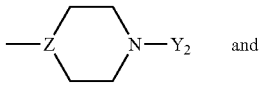

(b)

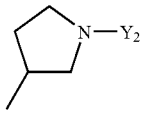

where Z is

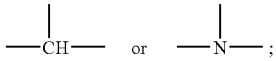

and $Y_2$ is selected from the group consisting of:

(1)

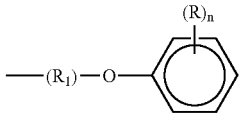

in which $(R_1)$ is $R_{20}$, $R_{21}$ or $R_{22}$, wherein:

$R_{20}$ is —$(CH_2)_n$— where n is 2, 3, 4 or 5;

$R_{21}$ is

—$CH_2$—CH═CH—$CH_2$—,

—$CH_2$—C≡C—$CH_2$—,

—$CH_2$—CH═CH—$CH_2$—$CH_2$—,

—$CH_2$—$CH_2$—CH═CH—$CH_2$—,

—$CH_2$—C≡C—$CH_2$—$CH_2$—, or

—$CH_2$—$CH_2$—C≡C—$CH_2$—, the —CH═CH— bond being cis or trans;

$R_{22}$ is $R_{20}$ or $R_{21}$ in which one or more carbon atoms of $R_{20}$ or $R_{21}$ are substituted by at least one $C_1$–$C_6$ linear alkyl group, phenyl group or

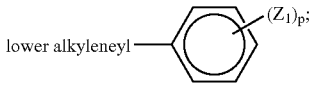

where $Z_1$ is lower alkyl, —OH, lower alkoxy, —$CF_3$, —$NO_2$, —$NH_2$ or halogen; and R and m are as defined hereinafter;

(2)

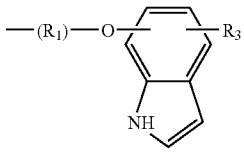

where $R_1$ is as previously defined, and $R_3$ is hydrogen or —$OCH_3$;

(3)

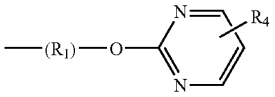

where $R_1$ is as previously defined; and $R_4$ is hydrogen, lower alkyl, lower alkoxy, hydroxy, amino, mono- or dialkylamino, $C_1$–$C_3$ acyl amino, $C_1$–$C_6$ alkanoyl, trifluoromethyl, chlorine, fluorine, bromine,

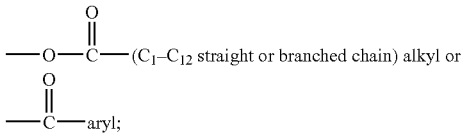

in which aryl is phenyl or

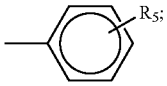

where $R_5$ is hydrogen, lower alkyl, lower alkoxy, hydroxy, chlorine, fluorine, bromine, iodine, lower monoalkylamino, lower dialkylamino, nitro, cyano, trifluoromethyl, trifluoromethoxy;

(4)

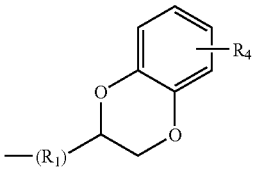

where $R_1$ and $R_4$ are as previously defined;

(5)

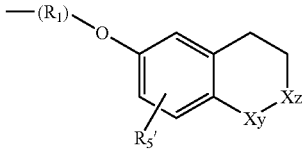

where either one of $X_y$, or $X_z$ is

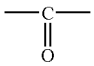

and the other is —$CH_2$—; and $R_5'$ is hydrogen, lower alkyl, lower alkoxy, chlorine, fluorine, or bromine; and $R_1$ is as previously defined;

(6)

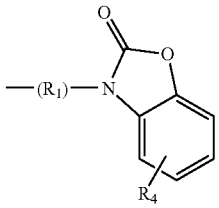

where $R_1$ and $R_4$ are as previously defined;

(7)

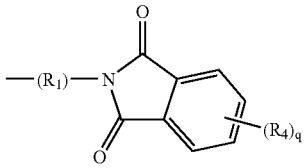

where q is 1, 2, 3 or 4, and $R_1$ and $R_4$ are as previously defined;

(8)

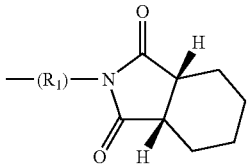

where $R_1$ is as previously defined;

(9)

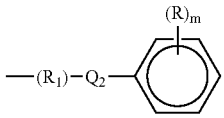

where $R_1$ is as previously defined;

$Q_2$ is S, NH, or —$CH_2$—; and

R and m are as defined hereinafter;

(10)

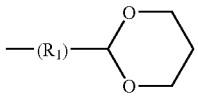

where $R_1$ is as previously defined;

$$—R_1—O—R_{12} \quad (11)$$

where $R_{12}$ is selected from the group consisting of: hydrogen,

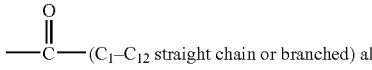

-continued $$-\overset{O}{\overset{\|}{C}}-NR_{13}R_{14},\quad -\overset{O}{\overset{\|}{C}}-NR_{15}R_{16},\quad \text{and}$$

$$-\overset{O}{\underset{O}{\overset{\|}{\underset{\|}{S}}}}-R_{17},$$

where $R_{13}$ is selected from the group consisting of hydrogen and ($C_1$–$C_{12}$) alkyl groups;

where $R_{14}$ is selected from the group consisting of hydrogen and ($C_1$–$C_{12}$) alkyl groups;

where $NR_{15}R_{16}$ taken together form a ring structure selected from the group consisting of piperidinyl, morpholinyl and piperazinyl;

where $R_{17}$ is selected from the group consisting of lower alkyl and aryl groups;

$$-R_1-NR_{18}R_{19} \qquad (12)$$

where $R_{18}$ and R 19 are independently selected from the group consisting of:

hydrogen, ($C_1$–$C_{12}$ straight or branched chain) alkyl, $$-\overset{O}{\overset{\|}{C}}-O-(C_1\text{–}C_{12})\text{alkyl},\quad -\overset{O}{\overset{\|}{C}}-(C_1\text{–}C_{12})\text{alkyl};\quad \text{and}$$

where $NR_{18}R_{19}$ taken together form a ring structure selected from the group consisting of piperidinyl, morpholinyl and piperazinyl;

$$-R_1-S-R_{12} \qquad (12)$$

where $R_1$ and R12 are as previously defined;

R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoalkylaminocarbonyl, dialkylaminocarbonyl, formyl, $$-\overset{O}{\overset{\|}{C}}\text{-alkyl},\quad -\overset{O}{\overset{\|}{C}}-\text{O-alkyl},\quad -\overset{O}{\overset{\|}{C}}\text{-aryl},$$

$$-\overset{O}{\overset{\|}{C}}\text{-heteroaryl},\quad -\overset{OR_7}{\overset{|}{C}}\text{H-alkyl},\quad -\overset{W}{\overset{\|}{C}}\text{-alkyl},$$

$$-\overset{W}{\overset{\|}{C}}\text{-aryl},\quad \text{and}\quad -\overset{W}{\overset{\|}{C}}\text{-heteroaryl};$$

alkyl is lower alkyl;

aryl is as previously defined;

heteroaryl is

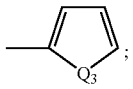

$Q_3$ is —O—, —S—, $$-\overset{|}{N}H,$$

—CH═N—;

W is $CH_2$ or $CHR_8$ or N—$R_9$;

$R_7$ is hydrogen, lower alkyl, or acyl;

$R_8$ is lower alkyl;

$R_9$ is hydroxy, lower alkoxy, or —$NHR_{10}$; and $R_{10}$ is hydrogen, lower alkyl, $C_1$–$C_3$ acyl, aryl, $$-\overset{O}{\overset{\|}{C}}\text{-aryl}\quad \text{or}\quad -\overset{O}{\overset{\|}{C}}\text{-heteroaryl},$$

where aryl and heteroaryl are as defined above; and m is 1, 2, or 3;

with the proviso that in formula (9) Z is not $$-\overset{|}{N}-$$

when X is —S—, $Q_2$ is —$CH_2$—, Y is hydrogen, lower alkyl, lower alkoxy, halogen, hydroxy, or trifluoromethyl, and p is 1 or 2;

with the proviso that in formula (4) $R_4$ is not H when $R_1$ is $R_{20}$, Z is not $$-\overset{|}{N}-,$$

X is —S—, Y is hydrogen, halogen, lower alkyl, lower alkoxy, hydroxy or trifluoromethyl, and p is 1 or 2;

with the proviso that in formula (9) Z is not $$-\overset{|}{C}H-$$

when X is $$-\overset{|}{N}H\quad \text{or}\quad -\overset{|}{N}R_2,$$

Y is hydrogen, halogen, lower alkyl, lower alkoxy, hydroxy or trifluoromethyl and $Q_2$ is —$CH_2$—;

with the proviso that in formula (9) Z is not

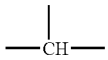

when X is —O—, $Q_2$ is —$CH_2$—, Y is hydrogen, lower alkyl, lower alkoxy, hydroxy or halogen, and p is 1 or 2;

with the proviso that in formula (9) Z is not

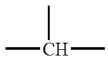

when X is —S—, $Q_2$ is —$CH_2$—, Y is hydrogen, halogen, lower alkyl, lower alkoxy or hydroxy, p is 1 or 2, R is hydrogen, and m is 1;

with the proviso that in formula (9) Z is not

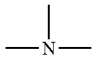

when X is

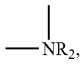

$Q_2$ is —$CH_2$—, R is chlorine, fluorine, bromine, iodine, lower alkyl, lower alkoxy, lower alkyl thio, lower mono- or dialkylamino, amino, cyano, hydroxy, trifluoromethyl; $R_2$ is aryl; Y is hydrogen, halogen, lower alkyl, lower alkoxy or hydroxy, p is 1 or 2;

with the proviso that in formula (9) Z is not

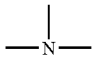

when X is

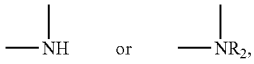

where $R_2$ is lower alkyl, aryl lower alkyl, or phenylsulfonyl, Y is hydrogen, halogen, lower alkyl, lower alkoxy or hydroxy, p is 1 or 2 and $Q_2$ is —$CH_2$—;

with the proviso that $Y_2$ is not the moiety of formula (8) when Z is

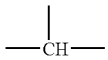

X is O, p is 1, and Y is hydrogen, lower alkyl, lower alkoxy, chlorine, fluorine, bromine, iodine or a hydroxyl group;

with the proviso that in formula (1) Z is not

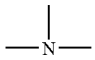

where X is O or S, Y is hydrogen, R is hydrogen, $C_1$–$C_4$ alkyl, chlorine, fluorine, bromine, iodine, cyano, $C_1$–$C_4$alkoxy, aryl, —$COOR_{23}$ where $R_{23}$ is $C_1$–$C_4$ alkyl;

with the proviso that in formula (1) Z is not

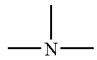

when X is —S—, $R_1$ is $R_{20}$, R is H, and m=1;

with the proviso that in formula (7) $R_4$ is not hydrogen when Y is 6-F, X is —O—, Z is

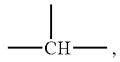

and n is 2, 3 or 4;

with the proviso that in formula (11) $R_{12}$ is not H when Z is

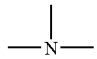

X is

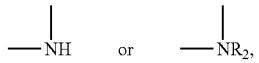

where $R_2$ is lower alkyl, aryl lower alkyl, or phenylsulfonyl Y is hydrogen, lower alkyl, lower alkoxy, chlorine, fluorine, bromine, iodine or a hydroxyl group and p is 1 or 2;

with the proviso that in formula (11), $R_{12}$ is not H when X is

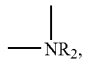

where $R_2$ is phenyl, Z is

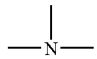

and Y is hydrogen, lower alkyl, lower alkoxy, chlorine, fluorine, bromine, iodine or a hydroxyl group;

with the proviso that in formula (12), $R_{18}$ and $R_{19}$ are not lower alkyl when Z is

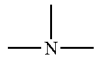

X is

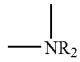

and $R_2$ is aryl and Y is hydrogen, lower alkyl, lower alkoxy, chlorine, fluorine, bromine, iodine or a hydroxyl group;

with the proviso that in formula (12), when X is —O—, Z is

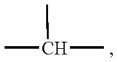

and Y is hydrogen, lower alkyl, lower alkoxy, chlorine, fluorine, bromine, iodine or a hydroxyl group, $R_{18}$ and $R_{19}$ are not lower alkyl;

with the proviso that in formula (12), $R_{18}$ and $R_{19}$ are not hydrogen when $R_1$ is $R_{20}$, Z is

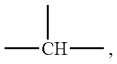

X is —O—, and Y is 6-F;

all geometric optical and stereoisomers thereof, or a pharmaceutically acceptable acid addition salt thereof This invention also provides a pharmaceutical composition, which comprises a compound of the invention and a pharmaceutically acceptable carrier therefor. In one embodiment of the invention, the pharmaceutical composition is an antipsychotic composition comprising a compound of the invention in an amount sufficient to produce an antipsychotic effect.

In addition, this invention provides a method of treating psychoses, which comprises administering to a patient a pharmaceutically effective amount of a compound of the invention.

Finally, this invention provides a method of alleviating pain by administering to a patient a pain-relieving amount of a compound of the invention.

DETAILED DESCRIPTION OF THE PREFERRED EMBODIMENT

The compounds of this invention are useful as antipsychotic drugs and as analgesic agents. The compounds of the invention can contain a variety of different substituents and chemical groups. As used herein, when the term "lower" is mentioned in connection with the description of a particular group, the term means that the group it is describing contains from 1 to 6 carbon atoms.

The term "alkyl" as used herein refers to a straight or branched chain hydrocarbon group containing no unsaturation, for example, methyl, ethyl, isopropyl, 2-butyl, neopentyl, or n-hexyl.

The term "alkoxy" as used herein refers to a monovalent substituent comprising an alkyl group linked through an ether oxygen having its free valence bond from the ether oxygen, e.g. methoxy, ethoxy, propoxy, butoxy, or pentoxy.

The term "alkylene" as used herein refers to a bivalent radical of a lower branched or unbranched alkyl group having valence bonds on two terminal carbons thereof, for example, ethylene ($—CH_2CH_2—$), propylene ($—CH_2CH_2CH_2—$), or isopropylene

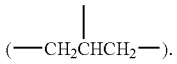

The term "cycloalkyl" refers to a saturated hydrocarbon group possessing at least one carbocyclic ring, the ring containing from 3 to 10 carbon atoms such as cyclopropyl, cyclobutyl, cyclopentyl, cyclohexyl, cycloheptyl, cyclodecyl and the like.

The term "alkanoyl" refers to the radical formed by removal of the hydroxyl function from an alkanoic acid. More particularly, the term "alkanoyl" as used herein refers to an alkyl carbonyl moiety containing from 2 to 11 carbon atoms, e.g.

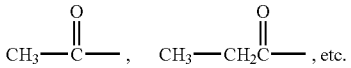

Examples of alkanoyl groups are formyl, acetyl, propionyl, 2,2-dimethylacetyl, hexanoyl, octanoyl, decanoyl, and the like.

The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid, and the like.

The term "aryl lower alkyl" refers to compounds wherein "aryl" and "loweralkyl" are as defined above.

The term "lower alkylthio" refers to a monovalent substituent having the formula lower alkyl—S—.

The term "phenylsulfonyl" refers to a monovalent substituent having the formula phenyl-$SO_2$—.

The term "acyl" refers to a substituent having the formula

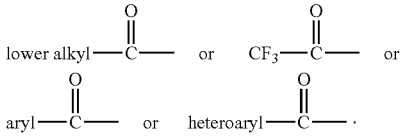

The term "lower monoalkylamino" refers to a monosubstituted derivative of ammonia, wherein a hydrogen of ammonia is replaced by a lower alkyl group.

The term "lower dialkylamino" refers to a disubstituted derivative of ammonia, wherein two hydrogens of ammonia are replaced by lower alkyl groups.

The term "acylamino" refers to a primary or secondary amine, wherein a hydrogen of the amine is replaced by an acyl group, where acyl is as previously defined.

The term "dialkylaminocarbonyl" refers to a derivative of an acid, wherein the hydroxyl group of the acid is replaced by a lower dialkylamino group.

The term "aroyl" refers to a disubstituted carbonyl, wherein at least one substituent is an aryl group, where "aryl" is as previously defined.

Unless otherwise indicated, the term "halogen" as used herein refers to a member of the halogen family selected from the group consisting of fluorine, chlorine, bromine, and iodine.

Throughout the specification and appended claims, a given chemical formula or name shall encompass all geometric, optical and stereoisomers thereof where such isomers exist.

A. COMPOUNDS OF THE INVENTION

The compounds of this invention can be represented by the following formula:

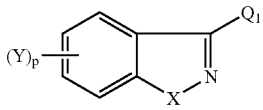

(I)

wherein

X is —O—, —S—,

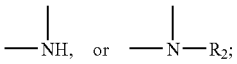

$R_2$ is selected from the group consisting of lower alkyl, aryl lower alkyl, aryl, cycloalkyl, aroyl, alkanoyl, and phenylsulfonyl groups;

p is 1 or 2;

Y is hydrogen, lower alkyl, hydroxy, chlorine, fluorine, bromine, iodine, lower alkoxy, trifluoromethyl, nitro, or amino, when p is 1;

Y is lower alkoxy, hydroxy and halogen when p is 2 and X is —O—;

$Q_1$ is selected from the group consisting of:

(a)

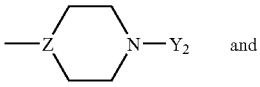

and (b)

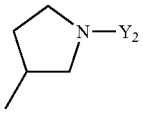

where Z is

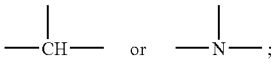

and $Y_2$ is selected from the group consisting of:

(1)

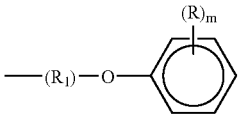

in which $(R_1)$ is $R_{20}$, $R_{21}$ or $R_{22}$, wherein $R_{20}$ is $—(CH_2)_n—$ where n is 2, 3, 4 or 5;

$R_{21}$ is $—CH_2—CH═CH—CH_2—$, $—CH_2—C≡C—CH_2—$, $—CH_2—CH═CH—CH_2—CH_2—$, $—CH_2—CH_2—CH═CH—CH_2—$, $—CH_2—C≡C—CH_2—CH_2—$, or $—CH_2—CH_2—C≡C—CH_2—$, the —CH═CH— bond being cis or trans;

$R_{22}$ is $R_{20}$ or $R_{21}$ in which one or more carbon atoms of $R_{20}$ or $R_{21}$ are substituted by at least one $C_1$–$C_6$-linear alkyl group, phenyl group or

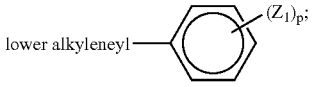

where $Z_1$ is lower alkyl, —OH, lower alkoxy, $—CF_3$, $—NO_2$, $—NH_2$ or halogen; and R and m are as defined hereinafter;

(2)

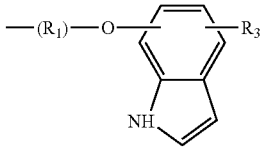

where $R_1$ is as previously defined, and $R_3$ is hydrogen or $—OCH_3$;

(3)

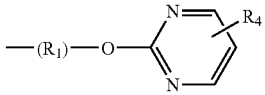

where $R_1$ is as previously defined; and $R_4$ is hydrogen, lower alkyl, lower alkoxy, hydroxy, amino, mono- or dialkylamino, $C_1$–$C_3$ acyl amino, $C_1$–$C_6$ alkanoyl, trifluoromethyl, chlorine, fluorine, bromine,

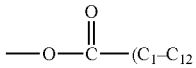

straight or branched chain) alkyl or

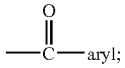

in which aryl is phenyl or

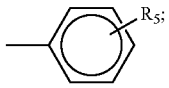

where $R_5$ is hydrogen, lower alkyl, lower alkoxy, hydroxy, chlorine, fluorine, bromine, iodine, lower monoalkylamino, lower dialkylamino, nitro, cyano, trifluoromethyl, trifluoromethoxy;

(4)

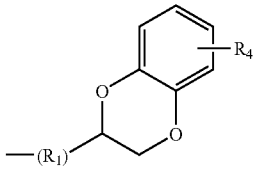

where $R_1$ and $R_4$ are as previously defined;

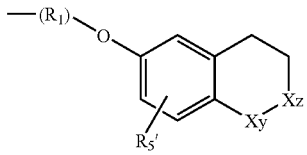

where either one of $X_y$ or $X_z$ is

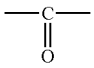

and the other is —$CH_2$—; and $R_5'$ is hydrogen, lower alkyl, lower alkoxy, chlorine, fluorine, or bromine; and $R_1$ is as previously defined;

(6)

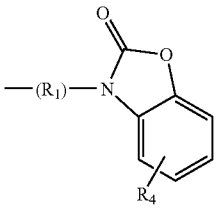

where $R_1$ and $R_4$ are as previously defined;

(7)

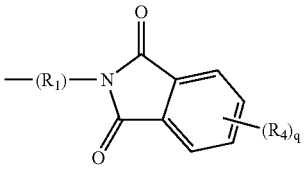

where q is 1, 2, 3 or 4, and $R_1$ and $R_4$ are as previously defined;

(8)

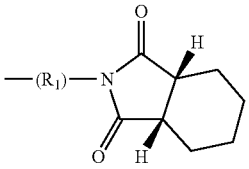

where $R_1$ is as previously defined;

(9)

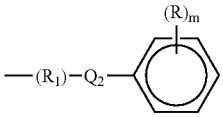

where $R_1$ is as previously defined;

$Q_2$ is S, NH, or —$CH_2$—; and

R and m are as defined hereinafter;

(10)

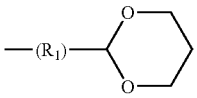

where $R_1$ is as previously defined;

$$—R_1—O—R_{12} \quad (12)$$

where $R_{12}$ is selected from the group consisting of:

hydrogen,

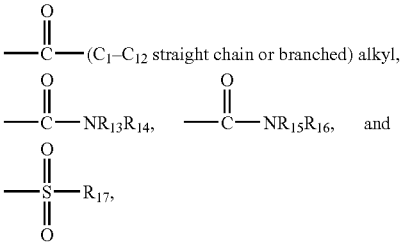

where $R_{13}$ is selected from the group consisting of hydrogen and ($C_1$–$C_{12}$) alkyl groups;

where $R_{14}$ is selected from the group consisting of hydrogen and ($C_1$–$C_{12}$) alkyl groups;

where $NR_{15}R_{16}$ taken together form a ring structure selected from the group consisting of piperidinyl, morpholinyl and piperazinyl;

where $R_{17}$ is selected from the group consisting of lower alkyl and aryl groups;

$$—R_1—NR_{18}R_{19} \quad (12)$$

where $R_{18}$ and $R_{19}$ are independently selected from the group consisting of:

hydrogen,

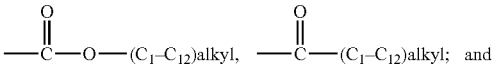

where $NR_{18}R_{19}$ taken together form a ring structure selected from the group consisting of piperidinyl, morpholinyl and piperazinyl;

$$—R_1—S—R_{12} \quad (13)$$

where $R_1$ and $R_{12}$ are as previously defined;

R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoalkylaminocarbonyl, dialkylaminocarbonyl, formyl,

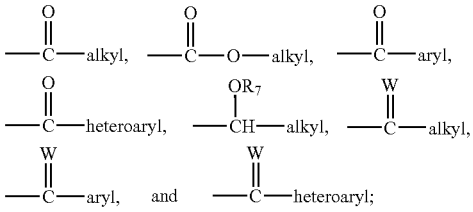

alkyl is lower alkyl;

aryl is as previously defined;

heteroaryl is

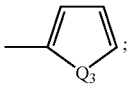

$Q_3$ is —O—, —S—,

—CH═N—;

W is $CH_2$ or $CHR_8$ or N—$R_9$;

$R_7$ is hydrogen, lower alkyl, or acyl;

$R_8$ is lower alkyl;

$R_9$ is hydroxy, lower alkoxy, or —$NHR_{10}$; and $R_{10}$ is hydrogen, lower alkyl, $C_1$–$C_3$ acyl, aryl,

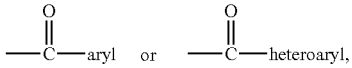

where aryl and heteroaryl are as defined above; and m is 1, 2, or 3;

with the proviso that in formula (9) Z is not

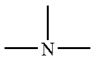

when X is —S—, $Q_2$ is —$CH_2$—, Y is hydrogen, lower alkyl, lower alkoxy, halogen, hydroxy, or trifluoromethyl, and p is 1 or 2;

with the proviso that in formula (4) $R_4$ is not H when $R_1$ is $R_{20}$, Z is not

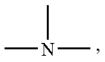

X is —S—S, Y is hydrogen, halogen, lower alkyl, lower alkoxy, hydroxy or trifluoromethyl, and p is 1 or 2;

with the proviso that in formula (9) Z is not

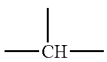

when X is

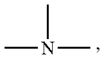

Y is hydrogen, halogen, lower alkyl, lower alkoxy, hydroxy or trifluoromethyl and $Q_2$ is —$CH_2$—;

with the proviso that in formula (9) Z is not

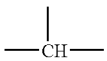

when X is —O—, $Q_2$ is —$CH_2$—, Y is hydrogen, lower alkyl, lower alkoxy, hydroxy or halogen, and p is 1 or 2;

with the proviso that in formula (9) Z is not

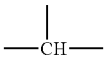

when X is —S—, $Q_2$ is —$CH_2$—, Y is hydrogen, halogen, lower alkyl, lower alkoxy or hydroxy, p is 1 or 2, R is hydrogen, and m is 1;

with the proviso that in formula (9) Z is not

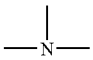

when X is

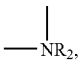

$Q_2$ is —$CH_2$—, R is chlorine, fluorine, bromine, iodine, lower alkyl, lower alkoxy, lower alkyl thio, lower mono- or dialkylamino, amino, cyano, hydroxy, trifluoromethyl; $R_2$ is aryl; Y is hydrogen, halogen, lower alkyl, lower alkoxy or hydroxy, p is 1 or 2;

with the proviso that in formula (9) Z is not

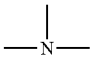

when X is

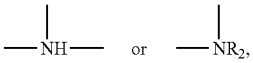

where $R_2$ is lower alkyl, aryl lower alkyl, or phenylsulfonyl, Y is hydrogen, halogen, lower alkyl, lower alkoxy or hydroxy, p is 1 or 2 and $Q_2$ is —$CH_2$—;

with the proviso that $Y_2$ is not the moiety of formula (8) when Z is

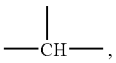

X is O, p is 1, and Y is hydrogen, lower alkyl, lower alkoxy, chlorine, fluorine, bromine, iodine or a hydroxyl group;

with the proviso that in formula (1) Z is not

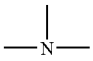

where X is O or S, Y is hydrogen, R is hydrogen, $C_1$–$C_4$ alkyl, chlorine, fluorine, bromine, iodine, cyano, $C_1$–$C_4$ alkoxy, aryl, —$COOR_{23}$ where $R_{23}$ is $C_1$–$C_4$ alkyl;

with the proviso that in formula (1) Z is not

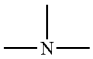

when X is —S—, $R_1$ is $R_{20}$, R is H, and m=1;

with the proviso that in formula (7) $R_4$ is not hydrogen when Y is 6-F, X is —O—, Z is

—CH—, and n is 2, 3 or 4;

with the proviso that in formula (11) $R_{12}$ is not H when Z is

—N—,

X is

—NH— or —$NR_2$, where $R_2$ is lower alkyl, aryl lower alkyl, or phenylsulfonyl Y is hydrogen, lower alkyl, lower alkoxy, chlorine, fluorine, bromine, iodine or a hydroxyl group and p is 1 or 2;

with the proviso that in formula (11), $R_{12}$ is not H when X is

—$NR_2$, where $R_2$ is phenyl, Z is

—N—, and Y is hydrogen, lower alkyl, lower alkoxy, chlorine, fluorine, bromine, iodine or a hydroxyl group;

with the proviso that in formula (12), $R_{18}$ and $R_{19}$ are not lower alkyl when Z is

—N—,

X is

—$NR_2$ $R_2$ is aryl and Y is hydrogen, lower alkyl, lower alkoxy, chlorine, fluorine, bromine, iodine or a hydroxyl group;

with the proviso that in formula (12), when X is —O—, Z is

—CH—, and Y is hydrogen, lower alkyl, lower alkoxy, chlorine, fluorine, bromine, iodine or a hydroxyl group, $R_{18}$ and $R_{19}$ are not lower alkyl;

with the proviso that in formula (12), $R_{18}$ and $R_{19}$ are not hydrogen when $R_1$ is $R_{20}$, Z is —CH—, X is —O—, and Y is 6-F;

all geometric optical and stereoisomers thereof, or a pharmaceutically acceptable acid addition salt thereof.

The compounds of the invention can also be represented by the following formula:

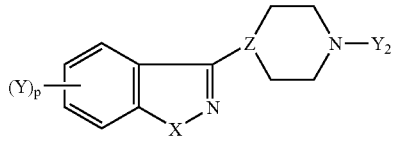

The substituent X in formula (I) is selected from the group consisting of —O—, —S—, —NH—, or

—N—$R_2$.

When the substituent X is —O—, the compounds of the invention contain a 1,2-benzisoxazole nucleus, and when X is —S—, the compounds of the invention contain a 1,2-benzisothiazole nucleus. When X is —NH— or

—N—$R_2$, the compounds of the invention contain the indazole nucleus.

When p in formula (I) is 1, the substituent Y is selected from the group consisting of hydrogen, lower alkyl, hydroxyl, halogen, lower alkoxy, —$CF_3$, —$NO_2$, and —$NH_2$. The substituent Y is preferably in the 5- or 6-position of the ring. Moreover, in the preferred embodiments of the invention, the substituent Y is hydrogen, chlorine, bromine, or fluorine, and in the particularly preferred compounds of the invention. Y is fluorine, especially in the 6-position of the ring.

When p in formula (I) is 2 and X is —O—, each Y substituent can be independently selected from lower alkoxy, hydroxy or halogen groups, preferably methoxy groups.

When the substituent $Y_2$ has the formula (b)(1):

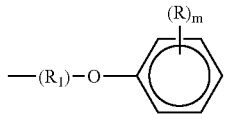

and $R_1$ contains unsaturation, $R_1$ preferably has the formula

—$CH_2$—CH=CH—$CH_2$—

When the substituent $Y_2$ has the formula (b)(3):

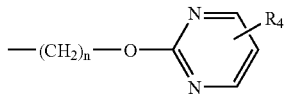

the substituent $R_4$ is preferably hydrogen or $C_1$–$C_6$ alkyl carbonyl and n is 3.

When the substituent $Y_2$ has the formula (b)(4):

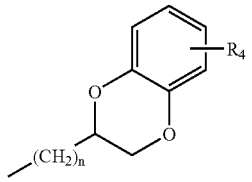

the substituent $R_4$ is preferably hydrogen or

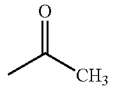

and n is preferably 1 or 2.

When the substituent $Y_2$ has the formula (b)(5):

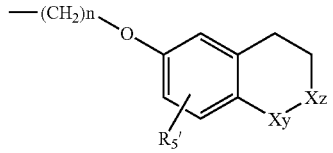

the substituent $R_5'$ is preferably —$OCH_3$ and n is preferably 3.

When the substituent $R_4$ has the formula (b)(6):

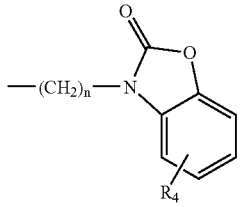

the substituent $R_4$ is preferably

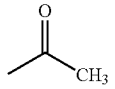

and n is preferably 3.

When the substituent $Y_2$ has the formula (b)(7):

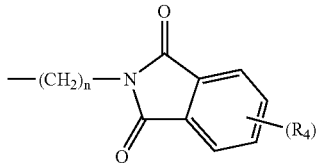

the substituent $R_4$ is preferably hydrogen and n is preferably 3 or 4.

When the substituent $Y_2$ has the formula (b)(8):

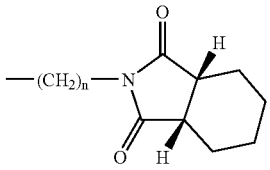

the value of n is preferably 3 or 4.

When the substituent $Y_2$ has the formula (b)(9):

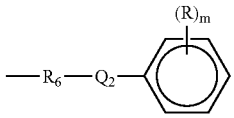

the substituent $R_6$ is preferably —$CH_2$—CH═C—H—$CH_2$— when $R_6$ contains unsaturation.

When the substituent R is

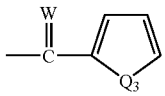

the substituent $Q_3$ is preferably —CH═N; and the substituent W is preferably $CH_2$, the substituent $R_8$ in $CHR_8$ is preferably $CH_3$, the substituent $R_9$ in N—$R_9$ is preferably hydroxy, lower alkoxy, or $NH_2$, and the substituent $R_{10}$ in $NHR_{10}$ is preferably hydrogen.

The value of n in the foregoing formulas can be 2, 3, 4, or 5, and preferably is 2, 3, or 4. In the particularly preferred compounds of the invention n is 3.

When X in the compounds of the invention is

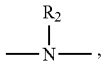

the substituent $R_2$ is selected from the group consisting of lower alkyl, aryl lower alkyl, aryl, cycloalkyl, aroyl, alkanoyl, and phenylsulfonyl groups.

The substituent Z can be

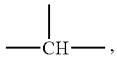

in which case the compounds of the invention are heteroarylpiperidine derivatives, or

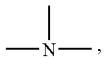

in which case the compounds are heteroarylpiperazine derivatives. When the substituent $Q_1$ has the formula

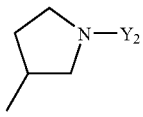

the compounds of the invention are heteroarylpyrrolidines.

The preferred compounds of the invention are the heteroarylpiperidines, i.e. compounds in which Z is

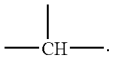

The compounds of the invention can contain one, two, or three R-substituents. The substituent R can be hydrogen, lower alkyl, $C_1$–$C_6$ alkoxy, hydroxyl, carboxyl, Cl, F, Br, I, amino, $C_1$–$C_6$ mono or dialkyl amino, —$NO_2$, lower alkyl thio, —$OCF_3$, cyano, acylamino, —$CF_3$, trifluoroacetyl (i.e.

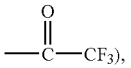

aminocarbonyl (i.e.

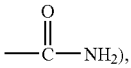

dialkylaminocarbonyl, formyl,

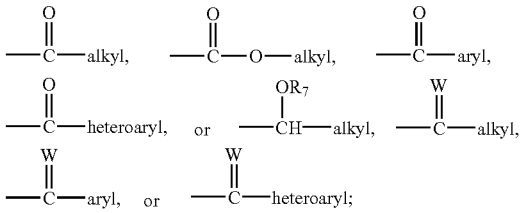

alkyl is lower alkyl;

aryl is phenyl or

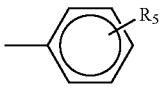

(1)

where $R_5$ is hydrogen, lower alkyl, $C_1$–$C_6$ alkoxy, hydroxy, Cl, F, Br, I, $C_1$–$C_6$ alkylamino, —$NO_2$, —CN, —$CF_3$, —$OCF_3$; heteroaryl is

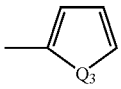

(2)

Q is —O—, —S—,

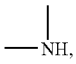

—CH═N—;

W is $CH_2$ or $CHR_8$ or N—$R_9$;

$R_7$ is hydrogen, lower alkyl, or acyl;

$R_8$ is lower alkyl;

$R_9$ is hydroxy, lower alkoxy, or —NHR10; and $R_{10}$ is hydrogen, lower alkyl, $C_1$–$C_3$ acyl, aryl,

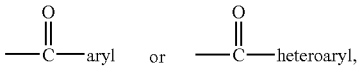

heteroaryl, where aryl and heteroaryl are as defined above; and m is 1, 2, or 3.

When the compounds of the invention contain two or three R-substituents, each of the R-substituents can be independently selected from the above substituents. Preferably, each of the R-substituents is selected from the group consisting of hydrogen, $C_1$–$C_3$ alkyl, $C_1$–$C_3$ alkoxy, hydroxyl, —$COCF_3$, $C_1$–$C_6$ alkanoyl, Cl, F, Br, I, $C_1$–$C_3$ alkylamino, —$NO_2$, —$CF_3$, —$OCF_3$,

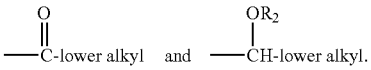

The compounds of the present invention are prepared in the following manner. The substituents R, $R_1$, $R_2$, $R_3$, X, Y, and Z and the integers m, n, and p are as defined above unless indicated otherwise.

B. PREPARATION OF COMPOUNDS OF THE INVENTION

The compounds of the invention can be prepared by reacting a piperidine or a piperazine of the formula:

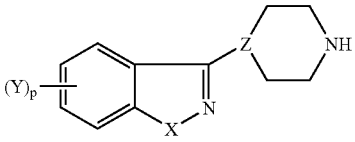

(3)

or a pyrrolidine of the formula:

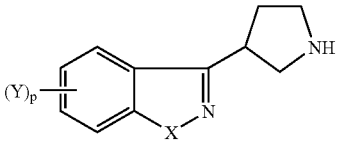

(3A)

under alkylating conditions with a compound of the formula:

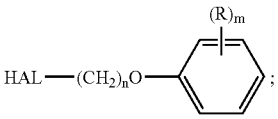

(4)

where HAL is Cl, Br, or I. The procedures that can be employed for preparing the piperidines, the piperazines, and the pyrrolidines and the alkylating agents identified by the above formulas will now be described in detail.

1. Preparation of 3-(1-unsubstituted-4-piperazinyl)-1H-indazoles

Compounds of the formulae:

(5)

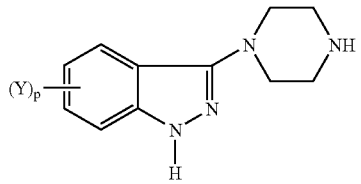

and (6)

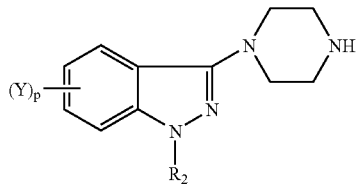

for use in synthesizing the indazolyl-substituted piperazines of the invention can be prepared as follows.

A substituted aryl ester of formula (7) is selected, (7)

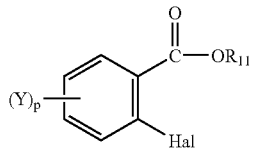

where $R_{11}$ is lower alkyl and Hal is a halogen selected from the group consisting of Cl, Br, and I. The ester of formula (7) is reacted with hydrazine, $H_2NNH_2$, under standard hydrazide formation conditions. Typically, the reaction is carried out in a nonreactive solvent, e.g. ethanol, methanoL, or toluene, at a temperature of ambient temperature to the reflux temperature of the solvent for 4 to 16 hours to form a hydrazide of formula (8):

(8)

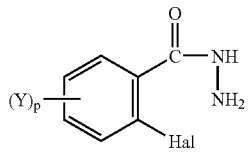

The hydrazide of formula (8) is reacted with a phenyl sulfonyl halide of the formula (9)

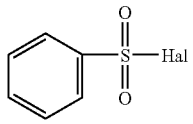

where Hal is a halogen selected from the group consisting Cl and Br, to form a compound of the formula (10)

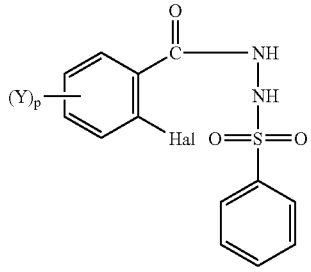

Typically this reaction is carried out in a basic solvent, such as pyridine or collidine, at a temperature of 0° to 30° C. for 2 to 16 hours.

The compound of formula (10) in turn is reacted neat with thionyl chloride at a temperature of 50° to 79° C. (reflux temperature) for 2 to 16 hours to form a compound of formula (11)

(11)

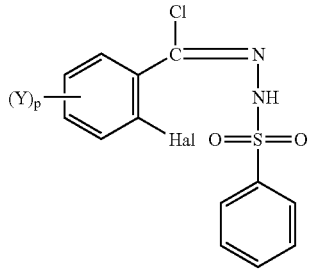

Compound (11) is reacted with a compound of formula (12), (12)

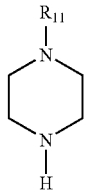

where $R_{11}$ is lower alkyl, under conventional nucleophilic reaction conditions, for example in as font solvent, such as tetrahydrofuran (THF), toluene, or diethylether, at a temperature of 5° to 50° C. for 1to 16 hours to form a compound having the formula (13)

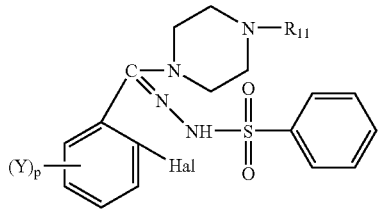

The compound of formula (13) is then reacted with a condensation agent, such a copper, copper-bronze, or cuprons oxide in a solved such as dimethylformamide dimethylacetamide, or tetramethylures, at a temperature of 120° to 177° C. for 1to 16 hours to form a piperazine-substituted phenylsulfonyl indazole of the formula (14)

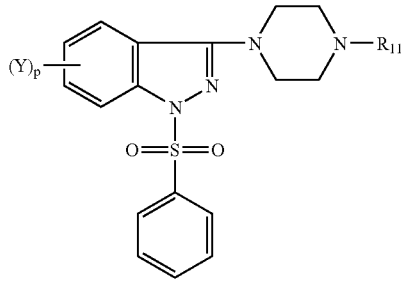

A cyano-substituted piperazine phenylsulfonyl indazole is then formed by reacting the compound of formula (14) with a conventional cyanation source, such as a halo-cyanide e.g. BrCN or ClCN, under conventional cyanation conditions, typically in an inert solvent e.g. dimethyl sulfoxide (DMSO) a $CHCl_3$ at ambient temperature for 2 to 16 hours to form a compound of formula (15)

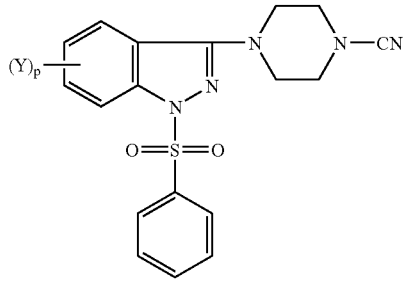

The compound of formula (5) is then subjected to reduction by means of a metal hydride, e.g. lithium aluminum hydride ($LiAlH_4$). Typically the reduction is carried out under standard reduction conditions in a solvent, such as tetrahydrofuran or diethyl ether, at a temperature of 33° to 67° C. for 6to 16 hours to forth a compound of formula (16).

(16)

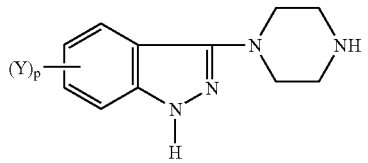

A compound of formula (16) can be formed in an alternative manner by first reacting a compound of formula (14) with a strong base, much as a metal alcoholate, as sodium methoxide sodium ethoxide, or sodium butoxide, or with KOH in tetrahydrofuran to form a compound at formula (17);

(17)

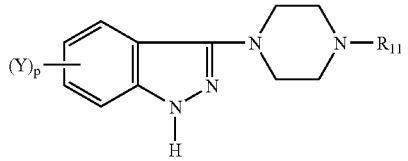

This reaction is typically carried as in a polar solvent, such as for example $CH_3OH$ or $C_2H_5OH$, at a temperature of ambient to 50° C. for 1 to 16 hours.

Alternatively, the compound of formula (17) can be formed by reducing compound (14) with $LiAlH_4$ under conditions as previously described.

The compound of formula (17) in turn can be reacted with a cyanation reagent, as previously described, to form a cyano substituted piperazine indazole of the formula (18)

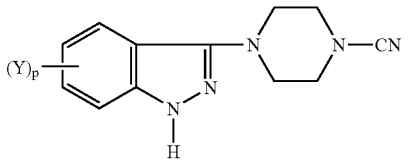

which in turn can be reduced with a metal hydride, as previously described, to form a compound of formula (16).

In an alternative embodiment, a compound of formula (18) can be reacted with an aqueous mineral acid, e.g. $H_2SO_4$ or HCl, at a temperature of 50° to 120° C. for 2to 16 hours to form a compound of formula (16).

2. Preparation of 3-(1-unsubstituted-4-piperazinyl)-1,2-benzisoxazoles

A compound of the formula:

(19)

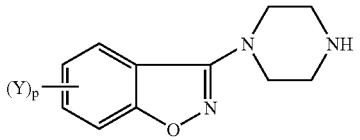

can be prepared according to conventional techniques. Suitable procedures are described in J. Med. Chem. 1986, 29:359. Compounds of formula (19) are useful for synthesizing the benzisoxazole substituted piperazines of the invention.

3. Preparation of 3-(1-unsubstituted-4-piperazinyl)-1,2-benzisothiazoles

A compound of the formula:

(20)

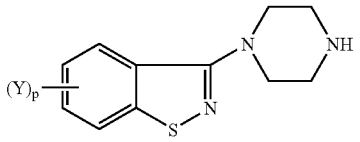

for use in synthesizing the benzisothiazole substituted piperazines of the invention can be prepared according to the techniques described J. Med. Chem. 1986, 29:359 and United Kingdom Patent (GB) 2 163 432 A.

4. Preparation of 3-(1-unsubstituted-4-piperidinyl)-1H-indazoles

A compound of the formula:

(21)

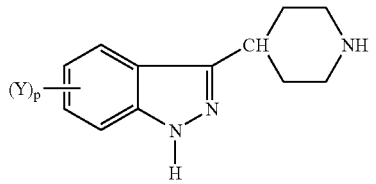

or (22)

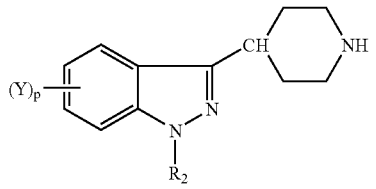

for use in synthesizing the piperidines of the invention can are be prepared using known techniques. For example suitable techniques are described in substantial detail i U.S. Pat. 4,710,573.

5. Preparation of 3-(1-unsubstituted-4-piperidinyl)-1,2-benzisoxazoles

A compound of the formula:

(23)

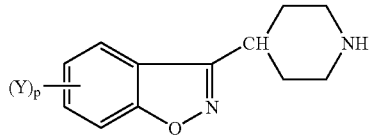

can be prepared by following the teachings from several sources. For example, U.S. Pat. No. 4,355,037 contains a detailed description of compounds of formula (23) and of methods for preparing the compounds. Additional disclosure of methods for preparing the compounds of formula (23) can be found in U.S. Pat. No. 4,327,103 and in Strupczewski et al., J. Med. Chem., 28:761–769 (1985). The compounds of formula (23) can be employed in the synthesis of the benzisoxazole substituted piperidines of the invention.

6. Preparation of 3-(1-unsubstituted-4-piperidinyl)-1,2-benzisothiazoles

Certain 3-(4-piperidinyl)-1,2-benzisothiazoles can be employed in the synthesis of the N-(aryloxyalkyl)-heteroaryl piperidines of the invention. Specifically, a benzisothiazole of the formula:

(24)

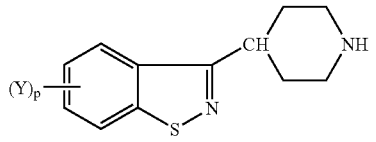

can be reacted with the alkylating agent previously described to form the N-(aryloxyalkyl)heteroarylpiperidines of the invention. Compounds of formula (24) and their methods of preparation are described in detail in U.S. Pat. No. 4,458,076.

7. Preparation of alkylating agents

The compounds described in Section 1-6 above can be reacted with alkylating agents of the formula:

(4)

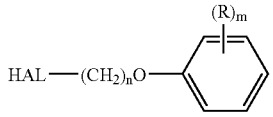

to form the N-(aryloxyalkyl)heteroarylpiperidines, piperazines, and pyrrolidines of the invention. The alkylating agents of formula (4) and methods for preparing the alkylating agents are described in U.S. Pat. No. 4,366,162. Additional disclosure as be found in South African publication EA 86 14522. Is addition, procedures for making agents are described in the following Examples. These procedures can be employed to make other alkylating agents for use in this invention.

8. Alkylation of heteroarylpiperidines, piperazines, and pyrrolidines to form the compounds of the invention The heteroarylpiperidines, piperazines, and pyrrolidines described in Sections 1–6 above can be reacted under alkylating condition with the alkylating agents described in Section 7to form the compounds of this invention. The reaction can be carried out by dissolving the reagents is an inert solvent, such as dimethylformamide, acetonitrile, or butanol, and allowing the reagents to react from a temperature of 50° C. to refluxing of the solvent in the presence of an acid receptor, such as a base. Examples of suitable bases are alkali metal carbonates, such as potassium carbonate, sodium carbonate, or sodium bicarbonate. The reaction can be carried out with or without a catalytic amount of an alkaline iodide, such a potassium iodide or sodium iodide, for a time sufficient to form a compound of formula (I) of the invention. Generally, the alkylation reaction is carried out for about 4to about 16 hours, depending on reactivity of the reagents. The reaction temperature can vary from about 50° to about 120° C. The products can be Isolated by treating the reaction product with water, extracting the product into in organic solvent that is immiscible in water, washing, drying, and concentrating the organic solvent to yield the free base, and then, if indicated, converting the resulting compound to an acid addition salt in a conventional manner.

Following are typical examples of compounds of the invention that can be prepared by following the techniques described above;

1-[4-[3-[4-(1H-indazol-3-yl)-1-piperanzinyl]propoxy]-3-methoxyphenyl]ethanone;

1-[4-[3-[4-(1,2-benzisoxazol-3-yl)-1-piperidinyl]propoxy]-3methoxyphenyl]ethanone;

1-[4-[3-[4-(6-fluoro-1,2-benzisoxazol-3-yl)-1-piperanzinyl]propoxy]-3-methoxyphenyl]ethanone;

1-[4-[4-[4-(1,2-benzisoxazol-3-yl)-1-piperidinyl]butoxy]-3methoxyphenyl]ethanone;

1-[4-[4-[4-(6-fluoro-1,2-benzisoxazol-3-yl)-1-piperandinyl]butoxy]-3-methoxyphenyl]ethanone;

1-[4-[2-[4-(1,2-benzisoxazol-3-yl)-1-piperidinyl]ethoxy]-3-methoxyphenyl]ethanone fumarate;

1-[4-[4-[4-(1H-indazol-3-yl)-1-piperanzinyl]butoxy]-3-methoxyphenyl]ethanone fumarate;

[4-[2-[4-(6-fluoro-1,2-benzisoxazol-3-yl)-1-piperandinyl] ethoxy]-3-methoxyphenyl]ethanone;
[3-[4-(6-fluoro-1,2-benzisoxazol-3-yl)-2-piperandinyl] propoxy]-3-methoxy-α-methylbenzenemethanol;
[4-[3-[4-(1,2-benzisothiazol-3-yl)-1-piperidinyl]-propoxy]-3-methoxyphenyl]ethanone;
[4-[3-[4-(6-fluoro-1,2-benzisoxazol-3-yl)-1-piperandinyl] propoxy]-3-hydrozyphenyl]ethanone;
[4-[3-[4-(6-fluoro-1H-indazol-3-yl)-1-piperandinyl] propoxy]-3-methoxyphenyl]ethanone;
[4-[4-[4-(6-fluoro-1H-indazol-3-yl)-1-piperandinyl] butoxy]-3-methoxyphenyl]ethanone;
1-[4-[3-[4-(1H-indazol-3-yl)-1-piperanzinyl]propoxy]-3methoxyphenyl]ethanone;
1-[4-[3-[4-(6-chloro-1,2-benzisoxazol-3-yl)-1-piperandinyl]propoxy]-3-methoxyphenyl]ethanone;
1-[4-[4-[4-(6-chloro-1,2-benzisoxazol-3-yl)-1-piperandinyl]butoxy]-3-methoxyphenyl]ethanone fumarate;
[4-[3-[4-(5-fluoro-1,2-benzisoxazol-3-yl)-1-piperandinyl] propoxy]-3-methoxyphenyl]ethanone;
6fluoro-3-[1-[3-(2-methoxyphenoxy)propyl]-4-piperandinyl]-1,2-benzisoxazol fumarate;
[4-[3-[4-(6-fluoro-1,2-benzisoxazol-3-yl)-1-piperandinyl] propoxy]-3-methoxyphenyl]phenylmethanone;
1-[4-[4-[4-(1H-indazol-3-yl)-1-piperanzinyl]propoxy]-3-methoxyphenyl]ethanone;
1-[4-[2-[4-(6-chloro-1,2-benzisoxazol-3-yl)-1-piperandinyl]ethoxy]-3-methoxyphenyl]ethanone;
1-[3-[3-[4-(6-fluoro-1,2-benzisoxazol-3-yl)-1-piperandinyl] propoxy]phenyl]ethanone fumarate;
1-[4-[3-[4-(6-fluoro-1,2-benzisoxazol-3-yl)-1-piperandinyl] propoxy]-2-methoxyphenyl]ethanone;
1-[2-[3-[4-(6-fluoro-1,2-benzisoxazol-3-yl)-1-piperandinyl] propoxy]-5-methoxyphenyl]ethanone;
N-[4-[3-[4-(6-fluoro-1,2-benzisoxazol-3-yl)-1-piperidinyl] propoxy]-3-methoxyphenyl]acetamide hemifumarate;
6-chloro-3-(1-piperazinyl)-1H-indazole;
1-[4-[3-[4-(6-fluoro-1H-indazol-3-yl)-1-piperidinyl] propoxy]-2-methoxyphenyl]ethanone;
1-[4-[3-[4-(6-fluoro-1,2-benzisoxazol-3-yl)-1-piperidinyl] propoxy]-3-methoxyphenyl]ethanone hemifumarate;
1-[4-[3-[4-(6-fluoro-1,2-benzisoxazol-3-yl)-1-piperidinyl] propoxy]phenyl]ethanone;
1-[4-[3-[4-(6-chloro-1H-indazol-3-yl)-1-piperazinyl] propoxy]-3-methoxyphenyl]ethanone;
1-[4-[4-[4-(1,2-benzisothiazol-3-yl)-1-piperazinyl]butoxy]-3-methoxyphenyl]ethanone;
4-[3-[4-[(6-fluoro-1,2-benzisoxazol-3-yl)-1-piperidinyl] propoxy]-3-methoxybenzonitrile;
1-[4-[4-[4-(6-fluoro-1H-indazol-3-yl)-1-piperazinyl] butoxy]-3-methoxyphenyl]ethanone;
1-[4-[3-[4-(6-benzoyl-6-fluoro-1H-indazol-3-yl)-1-piperidinyl]propoxy]-3-methoxyphenyl]ethanone sesquifumarate;
1-[4-[4-[4-(6-chloro-1H-indazol-3-yl)-1-piperazinyl]-butoxy]-3-methoxyphenyl]ethanone;
1-[4-[3-[4-(1,2-benzisothiazol-3-yl)-1-piperazinyl]-propoxy]-3-methoxyphenyl]ethanone hemifumarate;
1-[3,5-dibromo-4-[3-[4-(6-fluoro-1,2-benzisothiazol-3-yl)-1-piperadinyl]-propoxy]phenyl]ethanone;
1-[4-[2-[4-(1,2-benzisothiazol-3-yl)-1-piperazinyl]-ethoxy]-3-methoxyphenyl]ethanone;
6-fluoro-3-[1-(3-phenoxypropyl)-4-piperidinyl]-1,2-benzisoxazol;
1-[4-[2-[4-(6-chloro-1H-indazol-3-yl)-1-piperidinyl]-ethoxy]-3-methoxyphenyl]ethanone;
1-[4-[3-[4-(6-fluoro-1,2-benzisoxazol-3-yl)-1-piperidinyl] propoxy]-3-methylmercaptophenyl]ethanone;
1-[4-[4-[4-(1,2-benzisothiazol-3-yl)-1-piperadinyl]butoxy]-3-methoxyphenyl]ethanone;
1-[4-[3-[4-(6-fluoro-1,2-benzisoxazol-3-yl)-1-piperidinyl] propoxy]-3-methylmercaptophenyl]phenylmethanone;
1-[3-bromo-4-[3-[4-(6-fluoro-1,2-benzisoxazol-3-yl)-1-piperidinyl]propoxy]phenyl]ethanone;
3-[1-[3-[4-(1-ethoxyethyl)-2-methoxyphenoxy]propyl]-4-piperidinyl]-6-fluoro-1,2-benzisoxazole hydrochloride;
3-[1-3[-4-(1-acetoxyethyl)-2-methoxyphenoxy]propyl]-4-piperidinyl]-6-fluoro-1,2-benzisoxazole fumarate;
1-[4-[3-[4-(6-fluoro-1,2-benzisoxazol-3-yl)-1-piperidinyl) propoxy-3-methoxyphenyl]pentanone;
2-[3-[4-(6-fluoro-1,2-benzisoxazol-3-yl)-1-piperidinyl]-propoxy]-N-methylbenzamine hemifumarate;
3-[1-[3-(4-bromo-2-methoxyphenoxy)propyl]-4-piperidinyl]-6-fluoro-1,2-benzisoxazole;
1-[4-[3-[4-(6-fluoro-1,2-benzisoxazol-3-yl)-1-piperidinyl]-propoxy]-3-methoxyphenyl]propanone;
4-[3-[4-(6-fluoro-1,2-benzisoxazol-3-yl)-1-piperidinyl]-propoxy]-3-methoxybenzamide;
1-[4-[3-[4-(6-fluoro-1,2-benzisoxazol-3-yl)-1-piperidinyl] propoxy]-3-(methylamino)phenyl]ethanone;
1-[4-[3-[4-(6-fluoro-1,2-benzisoxazol-3-yl)-1-piperidinyl] propoxy[-3-ethoxyphenyl]ethanone;
N-[2-[3-[4-(6-fluoro-1,2-benzisoxazol-3-yl)-1-piperidinyl] propoxy]phenyl]acetamide;
1-[4-[3-[4-(6-fluoro-1,2-benzisoxazol-3-yl)-1-piperidinyl] propoxy]-3-dimethylaminophenyl]ethanone;
1-[4-[3-[4-(6-fluoro-1,2-benzisoxazol-3-yl)-1-piperidinyl] propoxy]-2-methoxyphenyl]ethanone hydrochloride;
1-[4-[3-[4-(6-fluoro-1,2-benzisoxazol-3-yl)-1-piperidinyl] propoxy]-3-methoxyphenyl]-2,2,2-trifluoroethanone;
4-[3-[4-(6-fluoro-1,2-benzisoxazol-3-yl)-1-piperidinyl]-propoxy]-3-hydroxy-α-methylbenzenemethanol;
2-[3-[4-(6-fluoro-1,2-benzisoxazol-3-yl)-1piperidinyl]-propoxy]aniline dihydrochloride;
N-[5-acetyl-2-[3-[4-(6-fluoro-1,2-benzisoxazol-3-yl)-1-piperidinyl)propoxy]phenyl]acetamide;
3-[1-[3-(4-ethyl-3methoxyphenoxy)propyl]-4-piperidinyl]-6-fluoro-1,2-benzisoxazole hydrochloride;
1-[3,5-dimethoxy-4-[3-[4-(6-fluoro-1,2-benzisoxazol-3-yl-1-piperidinyl]propoxy]phenyl]ethanone;
N-[3-[3-[4-(6-fluoro-1,2-benzisoxazol-3-yl)-1-piperidinyl] propoxy]phenyl]acetamide hemifumarate;
3-[3-[4-(6-fluoro-1,2-benzisoxazol-3-yl)-1piperidinyl]-propoxy]aniline;
3-[3-[4-(6-fluoro-1,2-benzisoxazol-3-yl)-1piperidinyl]-propoxy]-4-methoxyaniline;
1-[4-[3-[4-(6-fluoro-1,2-benzisoxazol-3-yl)-1piperidinyl] propoxy-3methoxyphenyl]ethanone fumarate;
N-[3-[3-[4-(6-fluoro-1,2-benzisoxazol-3-yl)-1-piperidinyl] propoxy]-4methoxyphenyl]acetamide;
1-[4-[3-(6-fluoro-1,2-benzisoxazol-3-yl)-1piperidinyl]-propoxy]-3methoxyphenyl]ethanone hydrochloride;
N,N-dimethyl-4-[3-[4-(6-fluoro-1,2-benzisoxazol-3-yl)-1-piperidinyl]propoxy]-3-methoxybenzamide;
1-[4-[3-[4-(6-fluoro-1,2-benzisoxazol-3-yl)-1-piperidinyl] propoxy]-3-methoxyphenyl]ethanone oxime;
1-[4-[3-[4-(6-fluoro-1,2-benzisoxazol-3-yl)-1-piperidinyl] propoxy]-methoxypenyl]ethanone oxime O-methyl ether;
1-[4-[3-[4-(6-fluoro-1,2-benzisoxazol-3-yl)-1-piperidinyl] propoxy]-3-methoxyphenyl]ethanone hydrazone;
6-fluoro-3-[1-[3-[2-methoxy-4-(1-methylethenyl)-phenoxy] propyl]-4-piperidinyl]-1,2-benzisoxazole hydrochloride;
(Z)-1-[4-[(4-chloro-2-butenyl)oxy]-3-methoxyphenyl] ethanone;

(Z)-1-[4-[[4-[4-(6-fluoro-1,2-benzisoxazol-3-yl)-1-piperidinyl]-2-butenyl]oxy]-3-methoxyphenyl]-ethanone;

(E)-1-[3-[[4-[4-(6-fluoro-1,2-benzisoxazol-3-yl)-1-piperidinyl]-2-butenyl]oxy]-4-hydroxyphenyl]ethanone hydrochloride;

(E)-1-[3-[[4-[4-(6-fluoro-1,2-benzisoxazol-3-yl)-1-piperidinyl]-2-butenyl]oxy]-4-benzyloxyphenyl] ethanone;

6-(3-chloropropoxy)-5-methoxy indole;

6-fluoro-3-[1-[3-[(5-methoxy-1H-indol-6-yl)oxy]-propyl]-4-piperidinyl]-1,2-benzisoxazole;

6-fluoro-3-[1-[3-[(1H-indol-7-yl)oxy]propyl]-4-piperidinyl] 01,2-benzisoxazole hemifumarate;

6-fluoro-3-[1-(3-hydroxypropyl]-4-piperidinyl]-1,2-benzisoxazole;

6-fluoro-3-[1-(2-pyrimidinoxy)propyl]-4-piperidinyl]-1,2-benzisoxazole fumarate;

6-aceto-2-[4-(6-fluoro-1,2-benzisoxazol-3-yl)-1-piperidinyl]methyl-1,4-benzodioxan;

2-[4-(6-fluoro-1,2-benzisoxazol-3-yl)-1-piperidinyl]-methyl-1,4-benzodioxan;

2-[4-(6-fluoro-1,2-benzisoxazol-3-yl)-1-piperidinyl]ethyl-1,4-benzodioxan;

6-(3-chloropropoxy)-7-methoxy-1-tetralone;

6-[3-[4-(6-fluoro-1,2-benzisoxazol-3-yl)-1-piperidinyl]-propoxy]-7-methoxy-1-tetralone;

N-(3-chloropropyl)-2-benzoxazolinone;

N-(3-chloropropyl)-6-acetyl-2-benzoxazolinone;

N-[3-[4-(6-fluoro-1,2-benzisoxazol-3-yl)-1-piperidinyl]-propyl-6-acetyl-2-benzoxazolinone;

N-[3-[4-(6-fluoro-1,2-benzisoxazol-3-yl)-1-piperidinyl]-propyl]phthalimide;

1-(3-aminopropyl)-4-(6-fluoro-1,2-benzisoxazol-3-yl) piperidine dihydrochloride;

cis-2-(3-(4(6-fluoro-1,2-benzisoxazol-3-yl)-1-piperidinyl) propyl-hexahydro-1H-isoindole-1,3-dione hydrochloride;

N-[4-[4-(6-fluoro-1,2-benzisoxazol-3-yl)-1-piperidinyl]-butyl]phthalimide;

1-(4-aminobutyl)-4-(6-fluoro-1,2-benzisoxazol-3-yl) piperidine dihydrochloride;

cis-(2-(4-(4-(6-fluoro-1,2-benzisoxazol-3-yl)-1-piperidinyl]-butyl)-hexahydro-1H-isoindole-1,3-dione hydrochloride;

1-[4-[[3-[4-(6-fluoro-1,2-benzisoxazol-3-yl)-1-piperidinyl] propyl]thio]-3-methoxypheyl]ethanone;

4-(6-fluoro-1,2-benzisoxazol-3-yl)-1-(2'-methoxyphenyl) butylpiperidine maleate;

4-(4-bromobutyl)-1-(1,2-dithian-2-yl)ethylbenzene;

1-[4-(1,3-dithian -2-yl)ethyl]phenyl-4-(6-fluoro-1,2-benzisoxazol-3-yl)butylpiperidine;

1-[4-(4'-acetophenyl)butyl]-4-(6-fluoro-1,2-benzisoxazol-3-yl)piperidine;

1-[4-[3-[4-(6-fluoro-1,2-benzisoxazol-3-yl)-1-piperidinyl] propylamino]-3-methoxyphenyl]ethanone;

(2,4-difluorophenyl)-[1-(phenylmethyl)-3-pyrrolidinyl]-methanone oxalate;

6-fluoro-3-[1-phenylmethyl)-3-pyrrolidinyl]-1,2-benzisoxazole fumarate;

(E)-1-[4-[(4-bromo-2-butenyl)oxy]-3-methoxyphenyl] ethanone;

4-(3-chloropropoxy)-3-methoxybenzaldehyde;

6-fluoro-3-(3-pyrrolidinyl)-1,2-benzisoxazole hydrochloride;

1-[4-[3-[4-(6-fluoro-1,2-benzisoxazol-3-yl)-1-piperidinyl] propylamino]-3-hydroxyphenyl]ethanone;

1-[3-acetylamino-4-(3-chloropropoxy)phenyl]ethanone;

N-[2-(3-hydroxypropoxy)phenyl]acetamide;

4-(3-chloropropoxy)-3-methoxybenzaldehyde;

(±)-1-[4-[3-[4-(6-fluoro-1,2-benzisoxazol-3-yl)-1-piperidinyl]-2-methylpropoxy]-3-methoxyphenyl] ethanone;

(S)-(+)-1-[4-[3-[4-(6-fluoro-1,2-benzisoxazol-3-yl)-1-piperidinyl]-2-methylpropoxy]-3-methoxyphenyl] ethanone;

(R)-(−)-1-[4-[3-[4-(6-fluoro-1,2-benzisoxazol-3-yl)-1-piperidinyl]-2-methylpropoxy]-3-methoxyphenyl] ethanone;

1-[4-[3-[4-[(6-fluoro-1,2-benzisoxazol-3-yl)-1-piperidinyl]-2,2-dimethylpropoxy]-3-methoxyphenyl-]ethanone;

(±)-1-[1-[3-[4-(6-fluoro-1,2-benzisoxazol-3-yl)-1-piperidinyl]-2-phenylpropoxy]-3-methoxyphenyl] ethanone;

(±)-1-[4-[3-[4-(6-fluoro-1,2-benzisoxazol-3-yl)-1-piperidinyl]-2-(3-chlorophenyl) propoxy]-3-methoxyphenyl]ethanone;

(±)-1-[4-[3-[4-(6-fluoro-1,2-benzisoxazol-3-yl)-1-piperidinyl]-2-(phenylmethyl)propoxy]-3-methoxyphenyl]ethanone;

(±)-1-[4-[3-[4-(6-fluoro-1,2-benzisoxazol-3-yl)-1-piperidinyl]-1-methylpropoxy]-3-methoxyphenyl] ethanone;

(±)-1-[4-[3-[4-(6-fluoro-1,2-benzisoxazol-3-yl)-1-piperidinyl]-3-methylpropoxy]-3-methoxyphenyl] ethanone;

(±)-1-[4-[4-[4-(1,2-benzisoxazol-3-yl)-1-piperidinyl]-3-methylbutoxy]-3-methoxyphenyl]ethanone;

(±)-1-[4-[4-[4-(1,2-benzisoxazol-3-yl)-1-piperidinyl]-3-phenylbutoxy]-3-methoxyphenyl]ethanone;

(±)-1-[4-[4-[4-(1,2-benzisoxazol-3-yl)-1-piperidinyl]-2-(2-phenylethyl)butoxy]-3-methoxyphenyl]ethanone;

(±)-[4-[2-[4-(6-fluoro-1,2-benzisoxazol-3-yl)-1-piperidinyl]-1-methylethoxy]-3-methoxyphenyl] ethanone;

(E)-1-[4-[[4-[4-(6-fluoro-1,2-benzisoxazol-3-yl)-1-piperidinyl]-1-methyl-2-butenyl]oxy]-3-methoxyphenyl] ethanone;

(Z)-1-[4-[[4-[4-(6-fluoro-1,2-benzisoxazol-3-yl)-1-piperidinyl]-3-methyl-2-butenyl]oxy]3-methoxyphenyl] ethanone;

(±)-1-[4-[[4-[4-(6-fluoro-1,2-benzisoxazol-3-yl)-1-piperidinyl]-1-propyl-2-butynyl]oxy]-3-methoxyphenyl] ethanone;

(S)-(+)-1-[4-[3-[4-(6-fluoro-1H-indazol-3-yl)-1-piperidinyl]-2-methylpropoxy]-3-methoxyphenyl] ethanone;

(R)-(−)-1-[4-[3-[4-(6-fluoro-1H-indazol-3-yl)-1-piperidinyl]-2-methylpropoxy]-3-methoxyphenyl] ethanone;

(±)-1-[4-[4-[4-(,2-benzisothiazol-3-yl)-1-piperidinyl]-3-methoxy]butoxy]-3-methoxyphenyl]ethanone;

(±)-1-[4-[3-[4-(6-fluoro-1,2-benzisoxazol-3-yl)-1-piperidinyl]-2-phenylpropoxy]-3-methoxyphenyl] ethanone; and (±)-6-fluoro-3-[1-[3-(2-methyl-(2-methoxyphenoxy)-propyl]-4-piperidinyl]-1,2-benzisoxazole.

The compounds of the present invention are useful for treating psychoses by virtue of their ability to elicit a antipsychotic response in mammals. Antipsychotic activity is determined in the climbing mice assay by a method similar to those described by P. Protais, et al., Psychopharmacol., 50:1 (1976) and B. Costall, Eur. J. Pharmacol., 50:39 (1978).

Subject CK-1 male mice (23–27 grams) are group-housed under standard laboratory conditions. The mice are individually placed in wire mesh stick cages (4"×10") and are allowed one hour for adaption and exploration of the new environment. Then apomorphine is injected subcutaneously at 1.5 mg/kg a dose causing climbing in all subjects for 30 minutes. Compounds to be tested for antipsychotic activity are injected intraperitoneally or given oral doses at various time intervals, e.g. 30 minutes, 60 minutes, etc. prior to the apomorphine challenge at 8 screening doses of 10–60 mg/kg.

For evaluation of climbing, 3 readings are taken at 10. 20, and 30 minutes after apomorphine administration according to the following scale:

| Climbing Behavior Mice with: | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging on to the cage walls, rather motionless, over long periods of time. By contrast, climbs due to mere motor stimulation usually only last a few seconds.

The climbing scores are individually totaled (maximal score: 6 per mouse over 3readings) and the total score of the control group (vehicle intraperitoneally-apomorphine subcutaneously) is set to 100%. $ED_{50}$ values with 95% confidence limits, calculated by a linear regression analysis, of some of the compounds of the, present invention as well as a standard antipsychotic agent are presented in Table 1.

TABLE 1

| COMPOUND | CLIMBING MOUSE ASSAY ($ED_{50}$ mg/kg, ip) |
|---|---|
| 1-[4-[3-[4-(1H-indazol-3-yl)-1-piperazinyl]propoxy]-3-methoxy-phenyl]ethanone | 0.98 |
| 1-[4-[3-[4-(1,2-benzisoxazol-3-yl)-1-piperidinyl]propoxy]-3-methoxy-phenyl]ethanone | 0.67 |
| 1-[4-[3-[4-(6-fluoro-1,2-benzisoxazol-3-yl)-1-piperidinyl]propoxy]-3-methoxy-phenyl]ethanone | 0.095 |
| 1-[4-[4-[4-(1,2-benzisoxazol-3-yl-1-piperidinyl]butoxy]-3-methoxyphenyl] ethanone | 1.6 |
| 1-[4-[4-[4-(6-fluoro-1,2-benzisoxazol-3-yl)-1-piperidinyl]butoxy]-3-methoxy-phenyl]ethanone | 0.68 |
| 1-[4-[3-[4-(6-fluoro-1,2-benzisothiazol-3-yl)-1-piperidinyl]propoxy]-3-methoxy-phenyl]ethanone hydrochloride | 0.16 |
| 2-[4-(6-fluoro-1,2-benzisoxazol-3-yl)-1-piperidinyl]ethyl]-1,4-benzodioxan | 0.29 |
| (Z)-1-[4-[[4-[4-(6-fluoro-1,2-benzisoxazol-3-yl)-1-piperidinyl]-2-butenyl]oxy]-3-methoxyphenyl]ethanone | 0.61 |
| 1-[4-(4'-acetophenyl)butyl]-4-(6-fluoro-1,2-benzisoxazol-3-yl)piperidine | 0.34 |
| 6-fluoro-3-[1-(3-hydroxypropyl)-4-piperidinyl]-1,2-benzisoxazole | 4.1 |
| 4-[4-(6-fluoro-1,2-benzisoxazol-3-yl)-1-piperidinyl]butyl decanoate fumarate | 3.31 |
| 1-(3-aminopropyl)-4-(6-fluoro-1,2-benzisoxazol-3-yl)piperidine dihydro-chloride | 22.6 |

TABLE 1-continued

| COMPOUND | CLIMBING MOUSE ASSAY ($ED_{50}$ mg/kg, ip) |
|---|---|
| N-[2-[4-(6-fluoro-1,2-benzisoxazol-3-yl)-1-piperidinyl]ethyl]phthalimide | 5.0 |
| 6-fluoro-3-[1-[3-[(isoquinol-5-yl)oxy] propyl]-4-piperidinyl]-1,2-benzisoxazole sesquifumarate | 0.172 |
| Chlorpromazine (standard) | 1.3 |

Antipsychotic response, is achieved when the compounds of the present invention are administered to a subject requiring such treatment as an effective oral, parenteral, or intravenous dose of from 0.01 to 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Some of the compounds of the present invention are also useful as analgetics due so their ability to alleviate pain in mammals. The analgetic utility is demonstrated in the phenyl p-quinone writhing assay in mice, a standard assay for analgesia: Proc. Soc. Exptl. Biol. Med., 95:729 (1937). Thus, for instance the subcutaneous dose effecting an approximately 50% inhibition of writhing ($ED_{50}$) in mice produced in this assay is as shown in Table 2.

TABLE 2

| COMPOUND | INHIBITION OF PHENYLQUINONE INDUCED WRITHING $ED_{50}$ mg/kg, sc |
|---|---|
| 1-[4-[3-[4-(1H-indazol-3-yl)-1-piperazinyl]propoxy]-3-methoxy-phenyl]ethanone | 0.06 |
| 1-[4-[3-[4-(1,2-benzisoxazol-3-yl)-1-piperidinyl]propoxy]-3-methoxyphenyl]ethanone | 0.17 |
| 1-[4-[3-[4-(6-fluoro-1,2-benzisoxazol-3-yl)-1-piperidinyl] propoxy]-3-methoxyphenyl]ethanone | 0.03 |
| Propoxyphene (standard) | 3.9 |
| Pentazocine (standard) | 1.3 |

Analgesia is achieved when the compounds of the present invention are administered to a subject requiring such treatment as an effective oral, parenteral, or intravenous dose of from 0.01 to 100 mg/kg of body weight per day. It is to be understood, however, that for any particular subject, dosage regimens should be adjusted according to the individual need and the professional judgment of the person administering or supervising the administration of the aforesaid compound. It is to be further understood that the damages set forth herein are exemplary only and that they do not, to any extent, limit the scope or practice of the invention.

Effective amounts of the compounds of the present invention can be administered to a subject by any one of several methods, for example, orally as in capsules or tablets, parenterally in the form of sterile solutions or suspensions, and in some cases intravenously in the form of sterile solutions.

The compounds of the present invention, while effective themselves, can be formulated and administered in the form of their pharmaceutically acceptable addition salts for purposes of stability, convenience of crystallization, increased solubility, and the like. Preferred pharmaceutically acceptable addition salts include salts include salts of mineral acids, for example, hydrochloric acid, sulfuric acid, nitric acid, and the like; salts of monobasic carboxylic acids, for example, acetic acid, propionic acid, and the like; salts of dibasic carboxylic acids, for example, maleic acid, fumaric acid, and the like; and salts of tribasic carboxylic acids, such as carboxysuccinic acid, citric acid, and the like.

Effective quantities of the compounds of the invention can be administered orally for example, with an inert diluent or with an edible carrier. They can be enclosed in gelatin capsules or compressed into tablets. For the purposes of oral therapeutic administration, compounds of the invention can be incorporated with an excipient and used in the form of tablets, troches, gums, and the like. These preparations should contain at least 0.5% of active compound of the invention, but can be varied depending upon the particular form and can conveniently be between 4% to about 70% of the weight of the unit. The amount of active compound in such a composition is such that a suitable dosage will be obtained. Preferred compositions and preparations according to the present invention are prepared so that an oral dosage unit form contains between 1.0–300 milligrams of the active compound of the invention.

Tablets, pills, capsules, troches, and the like can also contain the following ingredients: a binder, such as microcrystalline cellulose, gum tragacanth, or gelatin; an excipient, such as starch or lactose; a disintegrating agent such as alginic acid, primogel, corn starch, and the like; a glidant such as magnesium stearate or Sterores; a glidant such as colloidal silicon dioxide; and a sweetening agent such as sucrose; of saccharin, or a flavoring agent, such an peppermint, methyl salicylate, or orange flavoring. When the dosage unit form is a capsule, it can contain, in addition to materials of the above type, a liquid carrier such as a fatty oil. Other dosage unit forms can contain various materials that modify the physical form of the dosage unit, for example, as coatings. Thus, tablets or pills can be coated with sugar, shellac, or other enteric coating agent. A syrup can contain in addition to the active compounds, sucrose as a sweetening agent and certain preservatives, dyes colorings, and flavors. Materials used preparing these various compositions should be pharmaceutically pure and non-toxic in the amount, used.

For the purpose of parenteral therapeutic administration, the active compound of the invention can be incorporated into a solution or suspension. These preparations should contain at least 0.1% a active compound, but can be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5to 100 milligrams of active compound.

Solutions or suspensions can also include the following components: a sterile diluent, such as water for injection, saline solution, fixed oils, polyethylene glycols, glycerine, propylene glycol, or other synthetic solvents; agents such as benzyl alcohol or methyl parabens; antioxidants such as ascorbic acid, or sodium bisulfite; chelating agents such as ethylenediaminetetraacetic acid; buffers such at acetates, citrates, or phosphates, and agents for the adjustment of tonicity such as sodium chloride or dextrose. The parenteral preparation can be enclosed in ampules, disposable syringes, or multiple dose vials made of glass or plastic.

The following examples are for illustrative purposes only and are not to be construed as limiting the invention. All temperatures are given in degrees Centigrade (° C.) unless indicated otherwise.

EXAMPLE 1

Preparation of 1-[4-[3-[4-(1H-Indazol-3-yl)-1-piperazinyl]propoxy]-3-methoxyphenyl]ethanone

(A) Synthesis of 3-bromobenzoic acid 2-phenylsulfonylhydrazide

To a solution of 2-bromobenzoic acid, hydrazide (132 g) in pyridine (1.2 l) cooled to about 10° with an ice bath, was added benzenesulfonyl chloride (7.3 ml). After complete addition, the reaction was stirred at ambient temperature for four hours, and then poured into ice-hydrochloric acid to precipitate a yellow solid, 135 g. The material was recrystallized from isopropanol to yield 125 g of 2-bromobenzoic acid 2-phenylsulfonylhydrazide, m.p.=154°–156° C.

(B) Synthesis of α-chloro-2-bromobenzaldehyde phenylsulfonylhydrazone

A mixture of 2-bromobenzoic acid phenylsulfonylhydrazide (125 g, (1.35 mol) and thionyl chloride (265 ml) was stirred and refluxed for 2hours. After about 15 minutes of reflux, the solid went into solution. The reaction was permitted to cool, and then it was poured into hexane. The resultant white solid was collected to afford 124 g of α-chloro-2-bromobenzaldehyde phenylsulfonylhydrazone, m.p.=120°–122° C.

(C) Synthesis of 1-[[(phenylsulfonyl)hydroaono]-2-bromophenyl)methyl]-4-methylpiperazine To a stirred solution, under nitrogen, of α-chloro-2-bromobenzaldehyde phenylsulfonylhydrazone (271.1 g; 0.72 mol) in tetrahydrofuran (THF; 2liters), was added dropwise N-methylpiperazine (159.7 g; 1.6 mol). The reaction was stirred at ambient temperature for three hours, and then permitted to stand at ambient temperature for 16 hours. The reaction was chilled in an ice bath, and then filtered to remove the piperazine hydrochloride that was formed. The filtrate was concentrated to yield a brown gum. The gum was triturated with hot acetonitrile, the mixture was cooled in an ice bath, and when cold, was filtered to remove unwanted side product. The filtrate was then concentrated to afford 392.9 g of a brown gum of crude 1-[[(phenylsulfonyl) hydrazono]-(2-bromophenyrmethyl]-4-methylpiperazine.

(D) Synthesis of 3-(4-Methyl-1-piperazinyl)-1-phenylsulfonyl-1-indazole

A mixture of 1-[[(phenylsulfonyl)hydrazone]-(2-bromo phenyl)methyl]-4-methylpiperazine (31.0 g, 0.08 mol), copper bronze (3.1 g), $K_2CO_3$ (11.5 g), and dimethylformamide (500 ml), was stirred and refluxed for 1.5 hours. The reaction was poured into water and the aqueous suspension was stirred vigorously with ethyl acetate. The biphasic mixture was filtered through celite, and subsequently the layers were separated. The aqueous portion was extracted with another portion of ethyl acetate, and the combined extracts were washed ($H_2O$) and dried ($MgSO_4$). Concentration of the extract afforded a solid, which upon trituration with ether gave 19.7 g of solid. The solid was recrystallized from isopropanol afford 17.7 g (60%) of product, m.p. 158°–161° C. An analytical sample was obtained by another recrystallization from isopropanol (with charcoal treatment) to afford colorless crystals of the indazole, 3-(4-methyl-1-piperazinyl)-1-phenylsulfonyl-1H-indazole, m.p.=160°–161° C.

ANALYSIS

Calculated for $C_1H_{20}N_4O_2S$: 60.66% C 5.66% H 15.72% N.

Found: 60.45% C 5.62% H 15.61% N.

(E) Synthesis of 4-[1-(Phenylsulfonyl)-1H-indazol-3-yl]-1-piperazinecarbonitrile To a stirred mixture of 3-(4-methyl-1-piperazinyl)-1-phenylsulfonyl-1H-indazole (237 g, 0.67 mol), $K_2CO_3$ (102 g, 0.74 mol) and dimethylsulfoxide (DMSO, 2000 ml), under nitrogen, was added cyanogen bromide (72 g, 0.68 mol) dissolved in DMSO (25 ml). The reaction was stirred at ambient temperature for 5.5 hours and was then poured into $H_2O$ (7 l). The solid, which precipitated from solution, was collected by filtration, and was washed well with $H_2O$ affording 168 g (68%) of product. A 5.2 g sample was recrystallized twice from ethanol-$H_2O$ yielding 4.0 g of 4-[1-(phenylsulfonyl)-1H-indazol-3-yl]-1-piperazinecarbonitrile, m.p.=178°–180° C.

ANALYSIS

Calculated for $C_1H_{17}N_5O_2S$: 58.85% C 4.66% H 19.06% N.

Found: 59.01% C 4.63% H 19.09% N.

(F) Synthesis of 3-(1-Piperazinyl)]-1H-indazole

To a stirred mixture of 4-[1-(phenylsulfonyl)-1H-indazol-3-yl]1-piperazinecarbonitrile (163 g, 0.44 mol) in tetrahydrofuran (2.01) was added, dropwise, lithium aluminum hydride (880 ml, 0.88 mol of a 1M lithium aluminum hydride solution in tetrahydrofuran). After complete addition, the reaction was heated to reflux and stirred for 6hours, stirred at ambient temperature for one hour and allowed to sit at room temperature overnight. The reaction war quenched by the careful dropwise addition of water. After no more hydrogen could be observed to evolve, the reaction was filtered and the lithium salt filter cake was washed well with tetrahydrofuran. The filtrate was combined with the filtrate of another run (all together the starting material totaled 300 g, i.e. 0.82 mol) and the combined filtrates were concentrated to afford 372 g of a yellow solid suspended in water. An attempt was made to partition the product between water and dichloromethane, but the product proved to be only slightly soluble in dichloromethane. Therefore, the biphasic product suspension was filtered through a course sintered funnel and the white product which was collected was dried afford 121 g. The two phases of the filtrate were separated and the water was extracted again with dichloromethane. All of the dichloromethane phases were combined, washed twice with water, dried with magnesium sulfate, and concentrated to afford 41 g of a brown residue. The residue was triturated with diethyl ether and filtered to afford 10 g of a beige solid, m.p.=139°–150° C. The NMR and MS spectra were consistent with the structure. Recrystallization of 10 g from toluene afforded 7.3 g of 3-(1-piperazinyl)-1H-indazole, m.p.=153°–155° C.

(G) 3-4-Methyl-1-piperazinyl)-1H-indazole

A stirred mixture of 3-(-4methyl-1-piperazinyl)-1-phenylsulfonyl-1H-indazole (13.5 g, 0.038 mol), methanol (50 ml) and 25% $CH_3ONa$ in methanol (15.3 ml) was stirred and refluxed for 2.5 h. The reaction was concentrated to about one-tenth its volume, and water was added to the mixture, resulting in a red solution. The solution was extracted with dichloromethane, the extract washed ($H_2O$), dried ($MgSO_4$), and the solvent was concentrated to afford 6.6 g of a rose-colored solid. Two recrystallizations from toluene-hexane afforded 4.3 g (52%) of 3-(4-methyl-1-piperazinyl)-1H-indazole as an off-white solid, m.p.=111°–113° C.

ANALYSIS

Calculated for $C_{12}H_{16}N4$: 66.64% C 7.46% H 25–91% N.

Found: 66.83% C 7.42% H 25.69% N.

(H) 4-1H-indazol-3yl)-1-piperazinecarbonitrile

To a stirred mixture of cyanogen bromide (.3 g, 0.05 mol), $K_2CO_3$ (7.1 g) and dimethylsulfoxide (40ml) was added, dropwise, 3-(-4-methyl1-piperazinyl)-1H-indazole (11.0 g, 0.051 mol) dissolved in dimethylsulfoxide (60). The reaction was stirred at ambient temperature for 1 h, and then it was poured into water. The aqueous suspension was extracted with ethyl acetate, the ethyl acetate was washed ($H_2O$), dried ($MgSO_4$), and concentrated to afford 7.8 g (67%) of a yellow solid. This sample was combined with another and recrystallized twice from toluene to afford analytically pure 4-(1H-indazol-3-yl)-1-piperazinecarbonitrile as a white solid, m.p.=120°–122° C.

ANALYSIS

Calculated for $C_{12}H_{13}N_5$: 63.42% C 5.76% H.

Found: 63.04% C 5.84% H.

(I) Synthesis of 3-(1-Piperazinyl-1H-indazole

A mixture of 4 (1H-indazol-3-yl)-1-piperazinecarbonitrile (8.0 g, 0.04 mol) and 25% $H_2SO_4$ (100 ml) was stirred at reflux for 4.5 hours. The reaction was cooled in an ice bath and made basic by the dropwise addition of 50% NaOH. The basic solution was extracted with ethyl acetate. The ethyl acetate was washed with $H_2O$, dried with $MgSO_4$, and concentrated to afford 5.2 g (73%) of the desired compound, as a solid. The solid was recrystallized twice from toluene to afford 3.0 g of 3-(1-piperazinyl)-1H-indazole, m.p.=153–158° C.

ANALYSIS

Calculated for $C_{11}H_{14}N_4$: 65.32% C 6.98% H 27.70% N.

Found: 65.21% C 6.99% H 27.70% N.

(J) Synthesis of 1-[4-[3-[4(1H-indazole-3-yl)-1-piperazinyl]propoxy]-3-methoxyphenyl]ethanone A mixture of 3-(1-piperazinyl)-1H-indazole (4.0 g, 0.02 mol), $K_2CO_3$(3 g, 0.022 mol 1-[4-(3-chloropropoxy)-3-methoxypbenyl]ethanone (5.3 g, 0.022 mol), a few crystals of KI, and dimethylformamide (60 ml) was stirred at 90° C. for 5 hours. The reaction was poured into water, and the aqueous mixture was extracted with ethyl acetate. The extract was washed (brine), dried ($MgSO_4$), and the solvent was concentrated to afford a white solid, which was triturated with diethyl ether and collected to yield 7.0 g, of product. Two recrystallizatons from absolute ethyl alcohol yielded 5.3 g (64%) of analytically pure 1-[4-[3-(4-(1H-indazol-3-yl)-1-piperazinyl propoxy]-3-methoxyphenyl] ethanone, m.p.=155°–157° C.

ANALYSIS

Calculated for $C_{23}H_{28}N_8O_3$: 67.62% C 6.91% H 13.72% N.

Found: 67.45% C 6.74% H 13.56% N.

EXAMPLE 2

1-[4-[3-[4-(1,2-Benzisoxazol-3-yl)-1-piperadinyl] propoxyl]-3-methoxyphenyl]ethanone A mixture of 3-(4-piperidinyl)-1,2-benzisoxazole hydrochloride (4.8 g, 0.02 mol), $K_2CO_3$ (5.2 g, 0.04 mol), 1-[4-

(3-chloropropoxy)-3-methoxyphenyl]ethanone (5.3 g, 0.022 mol), a few crystals of KI and dimethylformamide (60 ml) was stirred at 90° C. for 16 hours. The reaction was poured into water and the aqueous mixture was extracted with ethyl acetate. The extract was washed (water), dried ($MgSO_4$) and concentrated to afford a brown oil. The oil was chromatographed on a Waters Prep 500 utilizing silica gel columns and ethyl acetatediethylamine (2%), eluent. Concentration of the appropriate fractions afforded 3.9 g of product as an off-white solid. Recrystallization from absolute ethyl alcohol afforded 26 g (33%) of 1-[4-[3-[4-(1,2-benzisoxazol-3-yl)-1-piperidinyl]propoxy]-3-methoxy-phenyl]ethanone, m.p.=102°101° C., as colorless needles.

ANALYSIS

Calculated for $C_{24}H_{28}N_2O_4$: 70.56% C 6.91% H 6.86% N.

Found: 70.73% C 6.93% H 6.85% N.

EXAMPLE 3

1-[4-[3-[4-(6-Fluoro-1,2-benzisoxazol-3-yl)-1-piperadinyl]propoxy]-3-methoxyphenyl]ethanone A stirred mixture of 6-fluoro-3-(4-piperidinyl)-1,2-benzisoxazole hydrochloride (5.1 g, 0.02 mol), $K_2CO_3$ (5.2 g. 0.04 g, mol), 1-(4-(3-chloropropoxy-3-methoxyphenyl] ethanone (5.3 g, 0.022 mol), and dimethylformamide (60 ml) was heated at 90° C. for 16 hour. The reaction was poured into water, and the aqueous mixture was extracted with ethyl acetate. The ethyl acetate was washed (water), dried ($MgSO_4$) and concentrated to afford a moist solid. Recrystallization (twice) from ethyl alcohol afforded 5.0 (58%) of 1-[4-[3-[4-(6-fluoro-1,2-benzisoxazol-3-yl)-1-piperidinyl]propoxy]-3methoxyphenyl]ethanone as a beige solid, m.p.=118°–120° C.

ANALYSIS

Calculated for $C_{24}H_{27}FN_2O_4$: 67.60% C 6.38% H 6.57% N.

Found: 67.47% C 6.40% H 6.53% N.

EXAMPLE 4

1-[4-[4-[4-(1,2-Benzisoxazol-3-yl)-1-piperidinyl] butoxy]-3-methoxyphenyl]ethanol A mixture of 3-(4-piperidinyl)-1,2-benzisoxazole hydrochloride (4.3 g, 0.018 mol), $K_2CO_3$ (5.5 g, 0.04 mol), and 1-[4-(4-bromobutoxy)-3-methoxyphenyl]ethanone (5.5 g, 0.018 mol), and dimethylformamide (60 ml) was stirred and heated at 75° C. for 16 hours. The reaction was poured into water and was extracted with ethyl acetate. The ethyl acetate was washed (water), dried ($MgSO_4$), and the solvent concentrated to afford 7.2 g of a beige solid. Recrystallization (twice) from ethyl alcohol yielded 3.3 g (43%) of 1-[4-[4-[4-(1,2-benzisoxazol-3-yl)-1-piperidinyl]butoxy]3-methoxyphenyl]ethanone, m.p.=99°–101° C.

ANALYSIS

Calculated for $C_{25}H_{30}N_2O_4$: 71.11% C 7.16% H 6.63% N.

Found: 70.76% C 7.24% H 6.58% N.

EXAMPLE 5

1-[4-[4-[4-(6-Fluoro-1,2-benzisoxazol-3-yl)-1-piperidinyl)butoxy]-3-methoxyohenylethanone A stirred mixture of 6-fluoro-3-piperidinyl)-1,2-benzisoxazole hydrochloride (5.1 g, 0.02 mol), $K_2CO_3$ (5.2 g, 0.04 mol), 1-(4-(4-bromobutoxy)-3-methoxyphenyl] ethanone (6.6 g, 0.022 mol), and dimethylformamide (60 ml) was heated at 75° C. for 5 hours. The reaction was poured into water, and the aqueous mixture was extracted with ethyl acetate. The ethyl acetate was washed (water), dried ($MgSO_4$), and the solvent was concentrated to yield initially an oil, which solidified upon standing. The solid was triturated with hexane and collected to afford 7.7 g of the product as a waxy solid. The compound was chromatographed on a Waters Prep 300 utilizing silica gel columns and eluting with dichloromethane/methanol (5%). Concentration of the appropriate fractions yielded 5.1 g of off-white solid 1-[4-[4-[4-(6-fluoro-1,2-benzisoxazol-3-yl)-1-piperidinyl]butoxy]-3-methoxyphenyl]ethanone, which when recrystallized from ethyl alcohol yielded 3.2 g (36%) of feathery-white needles, m.p.=88°–90° C.

ANALYSIS

Calculated for $C_{25}H_{29}FN_2O_4$: 68.16% C 6.64% H 6.36% N. Found: 6796% C 6.49% H 6.29% N.

EXAMPLE 6

1-[4-[2-[4-(1,2-Benzisoxazole-3-yl)-1-piperidinyl] ethoxy]-3-methoxyphenyl]ethanone fumarate A mixture of 3-(-4-piperidinyl)-1,2-benzisoxazole hydride (4.8 g, 0.02 mol), $K_2CO_3$ (5.2 g, 0.04 mol), 1-[4-(2-chloroethoxy)-3-methoxyphenyl]ethanone (5.0 g, 0.022 mol), and dimethylformamide (90 ml) was heated at 90° C. for 16 hours. The reaction was poured into water and the aqueous mixture was extracted with ethyl acetate. The ethyl acetate was washed (water), dried ($MgSO_3$), and the solvent was concentrated to afford an oil. Upon standing, the oil solidified to afford a beige solid. The crude solid was recrystallized twice from ethyl alcohol to afford 3.9 g of an off-white solid. The solid was dissolved is ethyl acetate, and fumaric acid (.2 g. 1.1 equiv.) was added. The mixture was heated briefly on a steam bath, and then stirred at ambient temperature for 2hours. An initial green oil settled out and the supernatant solutions was decanted. Ether was added to the decantate and 4.0 g of a white fumarate salt was collected. The salt was recrystallized twice from ethanol-ether to yield 1.7 g (17%) of 1-[4-[2-[4-(1,2-benzisoxazol-3-yl)-1-piperidinyl]ethoxy]-3-methoxyphenyl]ethanone fumarate, m.p.=127°–129° C.

ANALYSIS

Calculated for $C_{23}H_{26}N_2O_4C_4H_4O_4$: 63.52% C 5.92% H 5.49% N.

Found: 63.00% C 5.87% H 5.42% N.

EXAMPLE 7

1-[4-[4-[4-(1H-indazol-3-yl)-1-piperizinyl]butoxy]-3-methoxyphenyl]ethanone fumarate A stirred mixture of 3-(1-piperazinyl)-1H-indazole (4.0 g, 0.02 mol). $K_2CO_3$ (5.3 g, 0.04 mol), 1-[4-(4-bromobutoxy)-3methoxyphenyl]ethanone (6.6 g, 0.022 mol), and dimethylformamide (60 ml) was heated at 75° C. for 6hours. The reaction was poured into water, and a white solid precipitated from solution. The solid was collected and dried to afford 7.2 g of the crude product. The crude solid was recrystallized twice from ethyl alcohol to yield 4.1 g of the free base, which was converted to its fumarate salt by the addition of fumaric acid (1.1 g) to the compound dissolved in refluxing acetone. The resulting fumarate salt (5.0 g) was recrystallized from ethyl alcohol to afford 3.8 g (35%) of 1-[4-[4-[4-(1H-indazol-3-yl)-1-piperizinyl]butoxy)-3-methoxy phenyl]ethanone fumarate, as a white solid, m.p.= 163°–165° C.

ANALYSIS

Calculated for $C_{24}H_{30}N_4O_3.C_4H_4O_4$: 62.44% C 6.36% H 10.40% N. Found: 62.28% C 6.62% H 10.34% N.

EXAMPLE 8

1-[4-[2-[4-(-6-Fluoro-1,2-benzisoxazol-3-yl)-1-piperidinyl]ethoxy]-3-methoxyphenyl]ethanone A stirred mixture of 6-fluoro-3-(4-piperidinyl)-1,2 benzisoxazole hydrochloride (5.1 g, 0.02 mol), $K_2CO_3$ (5.2), 1-[4-(2-chloroethoxy)-3-methoxypbenyl]ethanone (5.0 g, 1.022 mol), and dimethylformamide (90 ml) was heated at 90° C. For 16 hours. The reaction was poured into water, and the aqueous mixture was extracted with ethyl acetate. The ethyl acetate was washed (water), dried ($MgSO_4$), and concentrated to afford 7.4 g of a yellow solid. The solid was chromatographed on a Waters Prep LC 500 utilizing dichloromethane/methanol (4%) as eluent, and subsequent concentration of the appropriate fraction afforded 4.0 g of a yellow solid. The solid was recrystallized from ethyl alcohol to yield 3.1 g (38%) of 1-[4-[2-[4-(-6-fluoro-1,2-benzisoxazol-3-yl)-1-piperidinyl]ethoxy]-3-methoxyphenyl]ethanone, as slightly yellow flakes m.p.=132°–134° C.

ANALYSIS

Calculated for $C_{23}H_{25}FN_2O_4$: 66.98% C 6.11% H 6.79% N.

Found: 66.90% C 6.20% H 6.74% N

EXAMPLE 9

4-[3-[4-(6-Fluoro-1,2-benzisoxazol-3-yl)-1-piperidinyl]-propoxy]-3-methoxy-α-methylbenzenemethanol To a stirred mixture of 1-[4-[3-[4-(6-fluoro-1,2-benzisoxazol-3-yl)-3-yl)-1-piperidinyl]propoxy-3-methoxyphenyl]ethanone (4.0 g 0.0094 mol) in methanol/tetrahydrofuran (60ml, 1:1), was added sodium borohydride (0.4 g, 0.01 mol). After an initial evolution of gas, all insolubles went into solution. The reaction was stirred at ambient temperature for 3hours and TLC at this time showed a very slight amount of starting ketone. Therefore, another 0.1 g of sodium borohydride was added, and stirring was continued for an additional 0.5 hour. TLC now showed complete disappearance of starting material The reaction was concentrated to an off white residue, which was diluted with water and collected to yield 3.4 g of alcohol. This was recrystallized from toluene (twice, with a charcoal treatment) to yield 2.7 g (67%) of 4-[3-[4-(6-fluoro-1,2-benzisoxazol-3-yl)-1-piperidinyl]-3-methoxy-α-methylbenzene-methanol as a white solid, m.p.=136°–138° C.

ANALYSIS

Calculated for $C_{24}H_{29}FN_2O_4$: 67.27% C 6.82% H 6.45% N.

Found: 67.59% C 6.89% H 6.47% N.

EXAMPLE 10

1-[4-[3-[4-(1,2-Benzisothiazol-3-yl)-1-piperidinyl]-propoxy]-3-methoxyphenyl]ethanone A mixture of 3-(4-piperidinyl)-1,2-benzisothiazole (3.0 g. 0.0137 mol), potassium carbonate (2.3 g, 0.0165 mol), 1-[4-(3-chloropropoxy)-3-methoxyphenyl]ethanone (4.0 g, 0.0165 mol), potassium iodide (200 mg) and acetonitrile (100 ml) was stirred at reflux under $N_2$ for 24 hours. The cooled reaction was filtered and the cake was washed well with acetonitrile. The filtrate was concentrated to an oily residue, which was partitioned between water and ethyl acetate. The ethyl acetate extract was washed well with water, dried with $MgSO_4$ and concentrated to yield 6.1 g of a beige oil upon solidified on standing. The product was triturated with diethyl ether and filtered to give 42 g of a beige solid. The compound was recrystallized from ethyl alcohol to afford 3.5 g, and another recrystallization from ethyl alcohol (utilizing decolorizing carbon) provided 2.4 g (41%) of 1-[4-[3-[4-(1,2 benzisothiazol-3-yl)-1-piperidinyl]propoxy]-3-methoxyphenyl]ethanone, m.p.=93°–96° C.

ANALYSIS

Calculated for $C_{24}H_{28}N_2O_3S$: 67.90% C 6.65% H 6.60% N.

Found: 67.89% C 6.61% H 6.39% N.

EXAMPLE 11

1-[4-[3-[4-(6-Fluoro-1,2-benzisoxazol-3-yl)-1-piperdinynl]propoxy]-3-hydroxyphenyl]ethanone (A) Synthesis of 1-[4-(3-hydroxyphenyl]ethanone To a stirred solution of 1-[4-(3-chloropropoxy)-3 methoxyphenyl]ethanone (10.0 g, 0.041 mol) in methylene chloride (120 ml) cooled to −50° C. (dry ice-methanol) was added, dropwise, 1M boron tribromide in methylene chloride (123 ml, 0.12 mol). The temperature was kept between −40° C. and −50° C. After compete addition, the reaction was permitted to reach −30° C., and the TLC checked (ca. 15 min. after final boron tribromide was added). Saturated $NaHCO_3$ was added, dropwise, never allowing the temperature to go above 0° C. during most of the addition. When sufficient $NaHCO_3$ had been added to make the solution basic, the organic layer was collected. The layer was washed with brine, dried ($MgSO_4$), and concentrated to yield 8.1 g of dark brown oil, which solidified on standing. This was chromatographed an a Waters Prop 500 LC (2silica columns, 2% methanol methylene chloride as eluent). Upon concentration of the appropriate factions, 5.8 g of a brown tacky solid were obtained. This was recrystallized from isopropyl other (with decanting of the yellow isopropyl ether supernatant from the dark brown oily residue) to give initially 2.5 g of a yellow solid. Concentration off the mother liquor gave as additional 0.5 g, m.p.=110°–113° C.

(B) Synthesis of 1-[4-[3-[4-(6-Fluoro-1,2-benzisoxazol-3-yl)-1-piperidinyl]propoxy]-3hydroxyphenyl]ethanone A stirred mixture of 6-fluoro-3-(4-piperidinyl)-1,2-benzisoxazole (2.8g, 0.013 mol) $NaHCO_3$ (1.1 g), several crystal of KI, 1-[4-(3-chloropropoxy)-3-hydroxyphenyl]ethanone, and acetonitrile (100 ml) was refluxed for 16 hours. The reaction was poured into water, and the aqueous mixture was extracted with ethyl acetate. The organic extract was washed (water), dried ($MgSO_4$), and the solvent was concentrated to afford 5.7 g of a thick yellow oil. The oil was chromatographed on a Waters Prep 500 LC on silica gel, eluting with 7% methanol/methylene chloride. Concentration of the appropriate fraction afforded a yellow oil, which upon standing yielded 3.5 g of the compound as a pale, yellow solid. The solid was recrystallized from ethyl alcohol to afford 2.7 g (50%) of 1-[4-[3-[4-(6-fluoro-1,2-benzisoxazole-3-yl)-1-piperidinyl[propoxy]-3-hydroxyphenyl]ethanone as a pale Yellow solid, m.p.=122°–124° C.

ANALYSIS

Calculated for $C_{23}H_{25}FN_2O_4$: 66.98% C 6.11% H 6.79% N.

Found: 66.97% C 6.20% H 6.69% N.

EXAMPLE 12

1-[4-[3-[4-(6-Fluoro-1H-indazol-3-yl)-1-piperazinyl]-propoxy]-3-methoxyphenyl]ethanone A stirred mixture of 6-fluoro-3-(1-piperazinyl)-1H-indazole (2.3 g, 0.01 mol), $K_2CO_3$(1.5 g), 1-[4-(3-chloropropoxy)-3-methoxyphenyl]ethanone (2.8 g, 0,011 mol), several crystals of KI and dimethylformamide (60ml) was heated at 90° C. for 16 hours. The reaction was poured into $H_2O$, and the aqueous suspension was extracted with ethyl acetate. The ethyl acetate was washed ($H_2O$), dried ($MgSO_4$) and concentrated to afford 5.0 g of a yellow oil. The oil was chromatographed on a Waters Prep 500 utilizing silica gel columns and eluting with methylene chloride/methanol (7%). Concentration of the desired fractions yielded 2.0 g (46%) of an off-white solid. This sample was combined with 1.0 g of a previous sample, and this was recrystallized from toluene to afford 2.6 g of 1-[4-[3-[4-(6-fluoro-1H-indazol-3-yl)-1-piperazinyl]propoxy]-3-methoxyphenyl)ethanone as a white solid, m.p.=135°–137° C.

ANALYSIS

Calculated for $C_{23}H_{27}FN_4O_3$: 64.77% C 6.38% H 13.14% N.

Found: 64.66% C 6.21% H 13.02% N.

EXAMPLE 13

1-[4-[4-[4-(6-Fluoro-1H-indazol-1-piperazinyl]-butoxy]-3-methoxyphenyl)ethanone

A stirred mixture of 6-fluoro-3-(-1-piperazinyl)-1H-indazole hydrochloride (5.0 g, 0.019 ml), $K_2CO_3$ (5.8 g) and 1-[4-(4-bromobutoxy)-3-methoxyphenyl]ethanone (6.3g, 0.021 mol) and dimethylformamide (80ml) was heated at 73° C. for 6hours. The reaction was poured into water and an off-white solid formed from solution. The solid was collected and dried to yield 4.5 g of crude product. The compound was recrystallized from ethanol (3times) to afford 3.0 g of an off-white solid. The solid was chromatographed on a Waters Prep 500 utilizing silica gel columns and eluting with methylene chloride/methanol (7%). Concentration of the appropriate fractions afford 2.3 g of an off-white solid, which when recrystallized from ethanol yielded 1.9 g (26%) of analytically pure 1-[4-[4-[4-(6-fluoro-1H-indazol-3-yl)-1-piperazinyl]butoxy]-3-methoxyphenyl]ethanone, m.p.=156°–138° C.

ANALYSIS

Calculated for $C_{24}H_{29}FN_4O_3$: 63.44% C 65.44% H 12.72% N.

Found: 65.38% C 6.49% H 12.60% N.

EXAMPLE 14

1-[4-[3-[4-(1H-Indazol-3-yl)-1-piperidinyl] propoxy]-3-methoxyphenyl]ethanone

A mixture of 3-(-4-piperidinyl)-1H-indazole (3.0 g, 0.015 mol), $K_2CO_3$ (1.6), 1-]4-(-3-chloropropoxy)-3-methoxyphenyl]ethanone (5.3 g; 0.022 mol), a few crystals or KI and acetonitrile (100 ml) was stirred and refluxed for 16 hours. The reaction was poured into water and a white solid separated from solution. The solid was collected, dried and afforded 5.1 g of product. Recrystallization from ethanol yielded 3.6 g of the compound, which upon chromatography (preparative HPLC on silica gel, eluting with methylene chloride/-methanol-9:1) gave 3.0 g (49%) of an off-white solid. Recrystallization from ethanol afforded the analytically pure 1[4-[3-[4-(1H-indazol-3-yl)-1-piperidinyl] propoxy]-3-methoxyphenyl]ethanone as a white solid, m.p.=171°–173° C.

ANALYSIS

Calculated for $C_{24}H_{29}N_3O_3$: 70.74% C 7.17% H 10.31% N. Found: 70.52% C 7.27% H 10.42% N.

EXAMPLE 15

1-[4-[3-[4-(6-Chloro-1,2-benzisoxazol-3-yl)-1-piperidinyl]propoxy]-methoxyphenyl]ethanone A stirred mixture of 6-chloro-3-(4-piperidinyl)-1,2-benzisoxazole (4.7 g, 0.02 mol), 1-[4-(3-chloropropoxy)-3-methoxyphenyl] ethanone (4.8 g, 0.02 mol, $K_2CO_3$ (2.8), several crystals of KI and acetonitrile (120 ml) was refluxed for 16 hours. The reaction was filtered and the filtrate was concentrated to yield a solid-oil mixture. The residue was chromatographed on a Waters Prep 500 utilizing silica columns and eluting with methylene chloride/methanol (5%). Concentration of the desired fractions yielded 3.2 g of a beige solid, which upon recrystallization from ethanol afforded 2.7 (31%) of 1-[4-[3-[4-(6-chloro-1,2-benzisoxazol-3-yl)-1-piperdinyl]propoxy]-3-methoxyphenyl]ethanone as a beige solid, m.p.=116°–118° C.

ANALYSIS

Calculated for $C_{24}H_{27}ClN_2O_4$: 65.08% C 6.14% H 6.32% N.

Found: 65.35% C 6.22% H 6.28% N

EXAMPLE 16

1-[4-[4-[4-(6-Chloro-1,2-benzisoxazol-3-yl)-1-piperidinyl]butoxy]-3-methoxyphenyl]ethanone fumarate A stirred mixture of 6-chloro-3-(4-piperidinyl-1,2-benzisoxazole (4.7 g, 0.02 mol), 1-[4-[4(4-bromobutoxy)-3methoxyphenyl]ethanone (6.0 g, 0.02 mol), $K_2CO_3$(2.8) and acetonitrile (120 ml) was refluxed for 16 hours. The reaction was allowed to cool, filtered, and the filtrate was concentrated to 9.9 g of a brown oil. The oil was chromatographed on a Waters Prep 500 utilizing silica gel columns and eluting with methylene chloride/methanol (5%). Concentration of the appropriate fractions afforded 2.3 g of an off-white solid. The solid was dissolved in ethanol and fumaric acid (0.62 g, 1.1 eq) was added. Upon concentration of the ethanol, a crude, brown solid was collected, which was taken up in refluxing acetone. Upon cooling a white solid crystallized from solution yielding 2.2 g (19%) of 1-[4-[4-[4-(6-chloro-1,2-benzisoxazol-3-yl)-1-piperidinyl] butoxy]-3-methoxyphenyl]ethanone fumarate as a white solid, m.p.=139°–141° C.

ANALYSIS

Calculated for $C_{25}H_{29}ClN_2O_4$: $C_4H_4O_4$: 60.78% C 5.80% H 4.89% N.

Found: 60.69% C 5.74% H 4.85% N.

EXAMPLE 17

1-[4-[3-[4-(5-Fluoro-1,2-benzisoxazol-3-yl)-1-piperidinyl]propoxy]-3-methoxyphenyl]ethanone A mixture of 5-fluoro-3-(-4-piperidinyl)-1,2benzisoxazole (2.2 g, 0.01 mole), 1-[4-(3-chloropropoxy)-

3-methoxyphenyl]ethanone (24g, 0.01 mole), $K_2CO_3$ (1.4 g), a few crystals of KI and acetonitrile (100 ml) was stirred and refluxed for 8hours. The reaction was poured into water and the aqueous mixture was extracted with ethyl acetate . The ethyl acetate extract was washed (brine), dried ($MgSO_4$) and concentrated to afford 4.0 g of a white solid. The solid was chromatographed on a Waters Prep 500 HPLC utilizing silica gel columns and eluting with methylene chloride/ methanol (5%). Concentration of the appropriate fractions afforded 2.0 g (47%) of 1-[4-[3-[4-(5-fluoro-1,2-benzisoxazol-[3-yl)-1-piperidinyl]propoxy]-3-methoxyphenyl]ethanone as a white crystalline solid, m.p.= 103°–105° C.

ANALYSIS

Calculated for $C_{24}H_{27}FN_2O$: 67,59% C 6.38% H 6.57% N.

Found with ): 67.50% C 6.47% H 6.53% H.

EXAMPLE 18

6-Fluoro-3-[1-[3-(-2-methoxyphenoxy)propyl]-4-piperidinyl]-1,2-benzisoxazole fumarate A stirred mixture of 6-fluoro-3-(-4-piperidinyl)-1,2-benzisoxazole (2.45 g; 11.1 mmoles), $K_2CO_3$ (2.0) and 3-(2-methoxyphenoxy)propyl chloride (3.5 g, 17.4 moles) is acetonitrile (40ml) was heated at 90° C. for 4hr. At the and of the reaction, the advent was removed, and the solids were dissolved into dichloromethane (100 ml). The solution was washed with water and brine, then dried over $MgSO_4$. The craft material from the solution was combined with 1.2 g of crude material, prepared in the same fashion (using 0.5 g of starting material). The combined material was purified by flash chromatography on a silica gel column (49g, eluted with 0.5% diethylamine: 1% methanol: 98.5% dichloromethane, 1 l). The fractions containing the pure product were pooled and concentrated down to a light oil (3.68). This oil was treated with fumaric acid (1.14 g, 9.8 mmoles) in ethanol (13ml). The 6-fluoro-3-[1-[3-(2-methoxyphenoxy)propyl]-4piperidinyl]1.2-benzisoxazole fumarate crystals obtained weighed 4.01 g (60%), m.p.= 169°–170° C.

ANALYSIS

Calculated for $C_{22}H_{25}FN_2O_3.C_4H_4O_4$: 62.39% C 5.84% H 5.60% N.

Found: 62.37% C 5.88% H 5.60% N.

EXAMPLE 19

1-[3-[3-[4-(-6-Fluoro-1,2-benzisoxazol-3-yl)-1-piperidinyl]propoxy]-4-methoxyphenyl] phenylmethanone A stirred mixture of 6-fluoro-3-(4-piperidinyl)-1,2 benzisoxazole (2.01 g; 9.13 moles), $K_2CO_3$ (2.0 g), and 1-[3-(3-chloropropoxy)-4-methoxyphenyl]phenylmethanone (3.93 g; 11.3 moles) and acetonitrile (50ml) was heated at reflex for 4hr. At the and of the reaction, the solvent was evaporated and the residue was partitioned between water (150 ml) and dichloromethane (400 ml). The dichloromethane solution was washed with water and brine (100 ml), dried over $MgSO_4$, then concentrated to an oil. The purification was done by flash chromatography over a silica gel column ($SiO_2$, 40 g; eluted with dichloromethane, 300 ml; 1% methanol in dichloromethane, 850 ml). The material thus obtained as a colorless oil solidified on standing. Recrystallization from ethanol (150 ml) gave 1-[4-[4-[4-(6-fluoro-1,2-benzisoxazol-3-yl)-1-piperidinyl]propoxy]-4-methoxyphenyl]phenylmethanone as white crystals, 3.07 g (63%, m.p.=140°–141° C.

ANALYSIS

Calculated for $C_{29}H_{29}FN_2O4$: 71.30% C 5.98% H 5.73% N.

Found: 71.09% C 5.98% H 5.73% N.

EXAMPLE 20

1-[4-[4-[4(1H-indazol-3-yl)-1-piperidinyl]butoxy]-3-methoxyphenyl]ethanone

A mixture of 3-(4-piperidinyl)-1H indazole (3.2 g, 0.016 mol), 1-[4-(4-bromobutoxy)-3-methoxyphenyl]ethanone (5.0 g, 0.016 mol) $K_2CO_3$ (2.2) and acetonitrile (100 ml) was stirred and refluxed for 6hours. The reaction was poured into water and the resulting yellow solid that formed was collected to afford 5.3 g of product. The compound was recrystallized from acetonitrile and then from ethyl acetate to yield 3.0 g (45%) of a slightly yellow solid of 1-[4-[4-[4-(1H-indazol-3-yl)-1-piperidiyl]butoxy]-3-methoxyphenyl]ethanone, m.p.=133°–135° C.

ANALYSIS

Calculated for $C_{25}H_{31}N_3O3$: 71.23% C 7.41% H 9.97% N.

Found: 70.85% C 7.61% H 9.81% N.

EXAMPLE 21

1-[4-[2-[4-(6-Chloro-1,2-benzisoxazol-3-yl)-1-piperidinyl]ethoxy]-3methoxyphenyl]ethanone A stirred mixture of 6-chloro-3-(4-piperidinyl)-1,2 benzisoxazole (4.6 g. 0.019 mol) 1-[4-(2-chloroethoxy)-3methoxyphenyl]ethanone (4.3 g. 0.019 mol), $K_2CO_3$ (2.8), a few crystals of KI and acetonitrile (120 ml) was refluxed for 16 hours. The reaction was filtered and the filtrate was concentrated to yield 8.0 g of yellow solid. The solid was chromatographed on a Waters Prep 500 LC (silica columns, eluting with methylene chloride/-methanol, 5%). Concentration of the appropriate fractions yielded 3.2 g of a light yellow solid, which upon recrystallization from ethyl acetate afforded 2.3 g (28%) of 1-[4-[2-[4-(6-chloro-1.2-benzisoxazol-3-yl)-1-piperidinyl]ethoxy]-3-methoxyphenyl]ethanone as a pale yellow solid, m.p.= 133°–135° C.

ANALYSIS

Calculated for $C_{23}H_{25}ClN_2O4$: 64.41% C 5.88% H 6.33% N.

Found: 64.351% C 5.87% H 6.41% N

EXAMPLE 22

3-(3-Bromopropoxy-4-methoxyphenyl) phenylmethanone

A solution of 3-hydroxy-4-methoxybenzophenone (4.6 g, 20 mmoles) in dimethylformamide (35ml) was treated with sodium hydride (600 mg, 25 mmoles) at 0° C. for 20 minutes, then 1,3-dibromopropane (5g, 24.7 moles was added in one portion. The mixture was heated at 90° C. for 1hr, and then stirred at room temperature for 2hr. At the end of the reaction, the mixture was poured into water (500 ml) and extracted with ethyl acetate (400 ml). The ethyl acetate solution was washed with water, brine and dried over anhydrous $MgSO_4$. The solvent was removed and the crude oil was purified by flash chromatography over a silica gel column ($SiO_2$, 85 g; eluted with 3l hexane:dichloromethane, 1.6; 3:7 hexane:dichloromethane, 1.41). The pure product thus obtained weighed 4.67 g, (66%) as an oil. Recrystallization twice from isopropyl ether (500 ml) gave analytically pure 3-(3-bromopropoxy-4methoxyphenyl)-phenylmethanone (2.42 g). m.p.=81°–83° C.

ANALYSIS

Calculated for $C_{17}H_{17}BrO_3$: 58.47% C 4.91% H

Found: 58.63% C 4.82% H.

EXAMPLE 23

1-[3-[3-[4-(6-Fluoro-1,2-benzisoxazol-3-yl)-1-piperidinyl]propoxy]phenyl]ethanone fumarate A mixture of 6-fluoro-3-(-4-piperidinyl)-1.2-benzisoxazole hydrochloride (4.53 in, 20.5 moles), $K_2CO_3$ (4.5 m), 1-[3-(3-chloropropoxy)phenyl]ethanone (6.4 g. 29 moles) in acetonitrile (60ml) was heated at reflux for 5hr. At the end of the reaction, the solvent was removed and the residue was extracted into dichloromethane (300 ml). The inorganic insolubles were filtered off. The dichloromethane solution was concentrated to a small volume (10 ml) and purified on a flash chromatographic column ($SiO_2$. 75 g, eluted with dichloromethane, 900 ml; and 2% methanol in dichloromethane, 800 ml). The fractions containing the pure product were combined and concentrated to an oil (2.87 g, 35%). The oil was dissolved into ethanol and treated with a solution of fumaric acid (841 mg). Recrystallization (twice) from ethanol afforded 2.53 g of 1-[3-[3-[4-(6-fluoro-1,2-benzisoxazol-3-yl)-1-piperidinyl]propoxy]phenyl)ethanone fumarate as white crystals, m.p.=172°–174° C.

ANALYSIS

Calculated for $C_{22}H_{25}FN_2O_3.C_4H_4O_4$63.27% C 5.70% H 5.47% N.

Found: 63.04% C 5.63% H 5.43% N.

EXAMPLE 24

1-[4-[3-[-4-(6-Fluoro-1,2-benzisoxazol-3-yl)-1-piperidinyl]propoxy]-2-methyphenyl]ethanone A stirred mature of 6-fluoro-3-(-4-piperidinyl)-1,2 benzisoxazole hydrochloride (5.5 g, 21.6 mmoles), $K_2CO_3$ (3.6 gm), 1-[4-(3-bromopropoxy)-2-methylphenyl]ethanone (4.83 g, 17.8 mmoles),in dimethylformamide (25ml) and acetonitrile (75ml) was heated at 120° C. for 5 hr. At the and of the reaction, the solvent was removed and the residue was extracted into dichloromethane (300 ml) and the solution was washed with water and brine. The organic solution was dried and evaporated to a crude oil. The purification was done by flash chromatography over a silica gel column (80g, eluted with dichloromethane, 1 l; 1% methanol:dichloromethane, 1.2 l; 2% methanol:dichloromethane, 1.2 l). The purest fractions were combined and afforded 2.91 g of solid. Recrystallization from dichloromethane and ethanol gave 1-[4-[3-[4-(6-fluoro-1,2-benzisoxazol-3-yl)-1-piperidinyl]propoxy]-2methylphenyl]ethanone as off-white crystals: 2.42 g, m.p.=113°–114° C.

Calculated for $C_{24}H_{27}FN_2O3$: 70.22% C 6.63% H 6.82% N.

Found: 70.13% C 6.63% H 6.77% N.

EXAMPLE 25

1-[2-[3-[4-(6-Fluoro-1,2-benzisoxazol-3-yl)-1-piperidinyl]propoxy]-5-methylphenyl]ethanone A mixture of 6-fluoro-3-(-4-piperidinyl)-1,2-benzisoxazole hydrochloride (2.87 g, 11.23 moles), $K_2CO_3$ (2.5), 1-[2-(3-bromopropoxy)-5-methylphenyl]ethanone (3.74 g. 13.8 mmoles) in dimethylformamide (10 ml) and acetonitrile (50 ml) was heated at 95° C. for 6hr. At the end of the reaction, the solvent was concentrated and the mixture was extracted into dichloromethane (300 ml). The organic solution was washed with water and brine, dried over ($MgSO_4$) then concentrated down to a crude oil. The purification was done by flash chromatography over a silica gel column ($SiO_2$, 60 g, eluted with 1% $CH_3OH$:dichloromethane: 1.2 l; 3% $CH_3OH$:dichloromethane: 600 ml). The material thus obtained was crystallized from a small volume of ether and hexane to provide 2.13 gm (46%) of off-white 1-[2-[3-[4-(6-fluoro-1,2-benzisoxazol-3-yl)-1-piperidinyl]lpropoxy]-5-methylphenyl]ethanone, m.p.=92°–93° C.

ANALYSIS

Calculated for $C_{24}H_{27}FN_2O_3$: 70.22% C 6.63% H 6.82% N.

Found: 70.21% C 6.69% H 6.81% N.

EXAMPLE 26

N-[3-[3-]4(6-Fluoro-1,2-benzisoxazol-3-yl)-1-piperidinyl]propoxy]-4methoxyphenyl]acetamide hemifumarate A mixture of 6-fluoro 3-(4-piperidinyl)-1,2-benzisoxazole hydrochloride (3.94 g, 15.4 moles), $K_2CO_3$ (3.67 g, 26.6 mmoles), N-[3-(3-bromopropoxy)-4-methoxyphenyl] acetamide (5.56 g: 18.6 mmoles) in dimethylformamide (75 ml) and acetonitrile (100 ml) was heated at 100° C. for 3hr. At the end of the reaction, the solvent was concentrated and the mixture was extracted into dichloromethane (500 ml). The organic solution was washed with water (500 ml) and brine (400 ml), dried, then concentrated to a crude oil. The purification was effected by flash chromatography over a silica gel column ($SiO_2$, 65 g, eluted with 1% $CH_3OH$:dichloromethane, 1.2 l; and 3% $CH_3OH$:dichloromethane, 500 ml). The material thus obtained weighed 2.33 g (34.3%) as an oil. This material was dissolved in ethanol treated with a solution of fumaric acid (661 mg) in ethanol. The N-[3-[3-[4-(5-fluoro-1,2 benzisoxazol-3-yl)-1-piperidinyl]propoxy]-4methoxyphenyl]acetamide hemifumarate was obtained as off-white crystals weighing 2.17 g, m.p.=205°–206° C.

ANALYSIS

Calculated for $C_{24}H_{28}FN_3O_4.0.5\ C_4H_4O_4$: 62.50% C 6.05% H 8.41% N.

Found: 62.30% C 6.03% H 8.32% N.

EXAMPLE 27

6-Chloro-3-(1-piperazinyl]-H-indazole

To a stirred suspension of 4-(-6-chloro-1-phenylsulphonyl-1H-indazol-3-yl)-1-piperazinecarbonitrile (192.5 g, 0.479 mol) in dry tetrahydrofuran (3.5 l) under $N_2$ was added, dropwise, $LiAlH_4$(958 ml of a 1.0M solution of lithium aluminum hydride in tetrahydrofuran; 0.958 mol. After complete addition, the reaction was heated to reflux and stirred under $N_2$ for 4hours. The reaction was cooled to 4° in an ice-salt bath and the excess lithium aluminum hydride was destroyed by the careful, dropwise addition of $H_2O$. The mixture was stirred vigorously for an additional 30 minutes and was then filtered through a coarse sintered glass funnel. The filter cake was washed well with tetrahydrofuran (3×500 ml) and then with methanol (2×500 ml) and the filtrate was concentrated to yield 1531.0 g of a beige gum. Trituration with diethyl ether afforded a solid, which was collected and dried to give 75.0 g (66%) of the desired indazole. A 4.0 g sample was recrystallized from toluene to yield 3.2 g, which was recrystallized again from toluene (utilizing decolorizing carbon) to provide 21 g (35%) of a beige, 6-chloro-3-(1-piperazinyl)-1H-indazole solid, m.p.=135°–137° C.

ANALYSIS

Calculated for $C_{11}H_{13}ClN_4$: 55.82% C 5.54% H 23.67% N.

Found: 55.91% C 5.54% H 23.41% N.

EXAMPLE 28

1-[4-[3-[4-(6-Fluoro-1H-indazol-3-yl)-1-piperidinyl]-propoxy]-3-methoxyphenyl]ethanone A stirred mixture of 6-fluoro-3-(-4-piperidinyl)-1H indazole (3.5 g, 0.016 mol) $K_2CO_3$ (2.2 g) 1-[4-(3-chloropropoxy)-3-methoxyphenyl]ethanone (3.8 g, 0.016mol) and acetonitrile (90ml) was refluxed for 16 hours. The reaction was poured into water and the resulting white solid, which precipitated from solution, was collected to afford 5.5 g of the desired product. The compound was recrystallized from dimethylformamide (twice) to afford 3.0 g (44%) of 1-[4-[3-[4-(6-fluoro-1H-indazol-3-yl)-1-piperidinyl]propoxy]-3-methoxyphenyl]ethanone as a white solid, m.p.=202°–204° C.

ANALYSIS

Calculated for $C_{24}H_{28}FN_3O3$: 67.75% C 6.63% H 9.88% N.

Found: 67.59% C 6.61% H 9.96% N.

EXAMPLE 29

1-[4-[3-[4-(6-Fluoro-1.2-benzisoxazol-3-yl)-1-piperidinyl]propoxy-3-methylphenyl]ethanone hemifumarate A stirred mixture of 6-fluoro-3-(4-piperidinyl)-1,2-benzisoxazole hydrochloride (3.0 g; 11.7 moles), $K_2CO_3$ (3.0 g), 1-[4-(3-bromopropoxy)-3-methylphenyl]ethanone (3.19 g) in dimethylformamide (20ml) acetonitrile (50ml) was heated at 95° C. for 4 hr. At the end of the reaction, the solvent was concentrated down to about 30 ml, then partitioned between water (200 ml) and dichloromethane (300 ml). The dichloromethane solution was separated and washed with water and brine then dried over $MgSO_4$. The crude product from the evaporated solution was purified by flash chromatography over a silica gel column ($SiO_2$, 60 g, eluted with 1% methanol in ethane, 600 ml; 2% methanol in dichloromethane, 600 ml). The material thus obtained was a light yellow oil, weight: 2.07 g (43%). The oil was dissolved in ethanol and treated with a solution of fumaric acid (585 mg) in ethanol. The 1-[4-[3-[4-(6-fluoro-1,2-benzisoxazol-3-yl)-1-piperidinyl]propoxy]-3-methylphenyl]ethanone hemifumarate crystals formed on cooling at 0° C. This was collected and weighed 1.5 g, m.p,=185°–187° C.

ANALYSIS

Calculated for $C_{24}H_{27}FN_2O_3.0.5\ C_4H_4$: 66.65% C 6.24% H 5.98% N.

Found 66.69% C 6.23% H 5.95% N.

EXAMPLE 30

1-[4-[3-[4-(6-Fluoro-1,2-benzisoxazol-3-yl)-1-piperidinyl]propoxy]phenyl]ethanone A mixture of 6-fluoro-3-(4-piperidinyl)-1,2-benzisoxazole (3.27 g, 14.8 mmoles), $K_2CO_3$(3 g), 1-[4-(3-bromopropoxy)phenyl]ethanone (4.5 g, 17.5 mmoles) in acetonitrile (60 ml) was heated at reflux for 4 hr. The solvent was removed. The residue was dissolved in dichloromethane (300 ml) and washed with water and brine, then dried over $MgSO_4$. The crude product from the evaporated solution was purified by flash chromatography ($SiO_2$. 60 g; eluted with 1% methanol in dichloromethane, methane 1liter). The purest fractions were combined and gave 2.8 g, 48% of 1-[4-[3-[4-(6-fluoro-1,2benzisoxazol-3-yl)-1-piperidinyl]propoxy)phenyl]ethanone, m.p.=111°–112° C.

ANALYSIS

Calculated for $C_{23}H_{25}FN_2O_3$: 69.68% C 6.36% H 7.07% N.

Found: 69.80% C 6.38% H 7.07% N.

EXAMPLE 31

1-[4-[3-[4(6-Chloro-1H-indazol-3-yl)-1-piperidinyl]-propoxy]-3-methoxyphenyl]ethanone A mixture of 6-chloro-3-(-1-piperazinyl)-1H-indazole (3.4 g, 0.014 mol), $K_2CO_3$ (2.5 g, 0.018 mol), 1-[4-(3-chloropropoxy)-3-methoxyphenyl]ethanone (3.8 g, 0.016 mol), KI (200 mg), and acetonitrile (125 ml) was stirred at reflux under $N_2$ for 30 hours. Alter standing at room temperature for 40 hours, the reaction was filtered and the filter cake was washed well with acetonitrile. The filtrate was concentrated to an oily solid, which was partitioned between water and ethyl acetate. The ethyl acetate extract was washed with water, dried with $MgSO_4$, and concentrated to yield 6.9 g of a dark oil, which solidified after 2days under vacuum. The product was purified by preparative HPLC (Waters Associates Prep LC/system 500 utilizing 2silica gel columns and 6% methanol/methylene chloride as eluent) to yield 4.2 g. The material was recrystallized from ethanol to yield 3.4 g of glistening, beige, 1-[4-[3-[4-(6-chloro-1H-indazol-3-yl)-1-piperazinyl]propoxy)-3-methoxyphenyl]ethanone crystals, m.p.=132°–134° C.

ANALYSIS

Calculated for $C_{23}H_{27}ClN_4O_3$: 62.37% C 6.14% H 12.65% N.

Found: 62.49% C 6.16% H 12.60% N.

EXAMPLE 32

1-[4-[4-[4-(1,2-Benzisothiazol-3-yl-1-piperazinyl]butoxy]-3-methoxyphenyl]ethanone A mixture of 3-(1-piperazinyl)-1.2-benzisothiazole (4.0 g, 0.0182 mol), 1-[4-(4-bromobutoxy)-3-methoxyphenyl]ethanone (6.0 g. 0.0218 mol). KI (200 mg), and acetonitrile (125 ml) was stirred at reflux under $N_2$ for 5hours. Most of the solvent was removed in vacuo and the resultant gummy residue was partitioned between ethyl acetate and-water. The organic extract was washed with water, dried with $MgSO_4$, and concentrated to yield 7.8 g. Purification by preparative HPLC (Waters Associates Prep LC/System 500, utilizing 2silica gel columns and 4% methanol-methylene chloride an eluent) afforded 6.5 g of a damp, off-white solid. The product was recrystallized twice from toluene to provide 3.1 g (39%) of 1-[4-[4-[4-(1,2-benzisothiazol-3-yl)-1-piperazinyl]-butoxy]-3methoxyphenyl ethanone as a white solid. m.p.=114°–116° C.

ANALYSIS

Calculated for $C_{24}H_{29}N_3O_3S$: 65.58% C 6.65% H 9.36% N.

Found: 65.74% C 6.66% H 9.54% N.

EXAMPLE 33

4-[3-[4-(-6-Fluoro-1,2-benzisoxazol-3-yl)-1-piperidinyl]-propoxy]-3-methoxybenzonitrile A mixture of 6-fluoro-3-(4-piperidinyl)-1,2-benzisoxazole (3.0 g, 13.6 mmoles), $K_2CO_3$ (2.8 g)-4-(3-bromopropoxy)-3-methoxybenzonitrile (4.0 gm, 14.8 mmoles) is acetonitrile (70ml) was heated at reflex for 3hr. At the end of the reaction, the solvent wet removed on a rotary evaporator. The organic material was extracted into dichloromethane (50 ml) and the inorganics were filtered off. The dichloromethane solution was concentrated to a crude oil. The purification was done by flash chromatography over a silica gel column ($SiO_2$, 55 gm; eluted with dichloromethane, 600 ml; 1% methanol in dichloromethane, 600 ml). The material thus obtained was crystallized from a small amount of dichloromethane. Recrystallization from ethanol (25ml) provided 3.8 m (68%) of 4-[3-[4-(-6-fluoro-1,2-benzisoxazol-3-yl)-1-piperidinyl]propoxy]-3-methoxybenzonitrile as white crystals. m.p.=107°–108° C.

ANALYSIS

Calculated for $C_{23}H_{24}FN_3O_3$: 67.47% C 5.91% H 10.26% N.

Found: 67.32% C 5.90% H 10.24% N.

EXAMPLE 34

1-[4-[4-[4-(6-Fluoro-1H-indazol-3-yl)-1-piperidinyl]-butoxy]-3-methoxyphenyl]ethanone A stirred of mixture of 6-fluoro-3-(4-piperidinyl)-1H-indazole (1.9 g, 0.0086 mol), 1-[4-(4-bromobutoxy)-3-methoxyphenyl]ethanone 2.6 g, 0.0086 mol), $K_2CO_3$ (1.2 g), and acetonitrile (7.5 ml) was refluxed for 6 hr. The reaction was poured into water and a white solid settled from solution. This was collected, dried and afforded 3.2 g of product. The product was recrystallized from ethanol to yield 2.7 g (71%) of 1-[4-[4-[4-(6-fluoro-1H-indazol-3-yl)-1-piperidinyl]butoxy-3-methoxyphenyl]ethanone as glistening white flakes, m.p.=158°–160° C.

ANALYSIS

Calculated for $C_{23}H_{25}FN_2O_3$: 68.32% C 6.88% H 9.56% N.

Found: 68.00% C 6.93% H 9.51% N.

EXAMPLE 35

1-[4-[3-[4-(1-Benzoyl-6-fluoro-1H-indazol-3-yl)-1-piperizinyl]propoxy]-3-methoxyphenyl]ethanone sesquifumarate A mixture of 1-[4-[3-[4-(6-fluoro-1H-indazol-3-yl)-1-piperazinyl]propoxy]-3-methoxyphenyl]ethanone (3.2 g, 0.0073 mol) and benzoyl chloride (15ml) was heated on a steam bath for 15 min. The reaction was allowed to cool and ether was added. The insoluble off white compound was harvested to yield 4.4 g of the product as a hydrochloride salt. The salt was converted to free base with aqueous ammonium hydroxide, and after extractive workup with methylene chloride, 3.0 g of the free base was isolated as a white solid. The free base was dissolved in ethyl acetate and fumaric acid (0.72 g, 1.1 eq) was added and the mixture heated on the steam bath for 15 min. After standing at ambient temperature for 4days, 2.0 g of an off-white fumarate salt was collected, while concentration of the filtrate afforded an additional 1.0 g of the salt. Recrystallization, first from ethyl acetate, and then from ethanol yielded 1.4 g (26%) of 1-[4-[3-[4(1-benzoyl-6-fluoro-1H-indazol-3-yl)-1-piperazinyl)-propoxy)-3-methoxyphenyl]ethanone sesquifumarate, m.p.=138°–140° C.

ANALYSIS

Calculated for $C_{30}H_{31}FN_4O_4.1.5C_4H_4O_4$: 61.35% C 5.29% H 7.95% N.

Found: 61.68% C 5.31% H 8.25% N.

EXAMPLE 36

1-[4-[4-[4-(6-Chloro-1H-indazol-3-yl)-1-piperazinyl]butoxy]-3-methoxyphenyl]ethanone A mixture of 6-chloro-[3-(1-piperazinyl)]-1H-indazole (4.0 g, 0.017 mol), $K_2CO_3$ (2.8 g, 0.0020 mol), 1-[4-(4-bromobutoxy)-3-methoxyphenyl]ethanone (5.7 g, 0.019 mol), KI (100 mg) and acetonitrile (125 ml) was stirred at reflux under nitrogen for 18 hrs. The cooled reaction was poured into water and the resultant off-white solid was collected by filtration and dried to yield 7.0 g. The compound was recrystallized twice from toluene to yield 6.2 g. Further, purification by preparative HPLC (Waters Associates Prep LC/System 500, utilizing 5% methanol/methylene chloride as eluent and 2 silica gel columns) afforded 5.3 g of glistening, beige crystals, which were recrystallized four times from toluene to yield 3.1 g of a white solid. Analytically pure material was obtained by a subsequent recrystallization from dimethylformamide to afford 2.5 g (32%) of 1-[4-[4-[4-(6-chloro-1H-indazol-3-yl)-1-piperazinyl]butoxy]-3-methoxyphenyl]ethanone as an off-white powder, m.p.=189°–191° C.

ANALYSIS:

Calculated for $C_{24}H_{29}ClN_4O_3$: 63.08% C 6.40% H 12.26% N.

Found: 62.86% C 6.57% H 12.49% N.

EXAMPLE 37

1-[4-[3-[4-(1,2-Benzisothiazol-3-yl)-1-piperazinyl]propoxy]-3-methoxyphenyl]ethanone hemifumarate A mixture of 3-(1-piperazinyl)-1,2-benziothiazole (4.0 g, 0.0182 mol), $K_2CO_3$ (3.0 g, 0.0218 mol), KI (200 mg), 1-[4-(3-chloropropoxy)-3-methoxyphenyl]ethanone (5.3 g, 0.0200 mol), and acetonitrile (125 ml) was stirred at reflux under $N_2$ for 26 hours. The cooled reaction was filtered and the filter cake was washed well with acetonitrile. The filtrate was concentrated to afford 10.7 g of an oily residue, which was extracted with ethyl acetate. The ethyl acetate extract was washed with water, dried with $MgSO_4$ and concentrated to yield 8.0 g of a dark oil. The oil was purified by preparative HPLC (Waters Associates Prep LC/System 500, utilizing 2 silica gel columns and 3% methanol/methylene chloride as eluent). Concentration of appropriate fractions provided 4.6 g of a red oil, which solidified upon standing. A 3.4 g sample was taken up in ethyl acetate (100 ml) and fumaric acid (0.95 g) was added. The mixture was stirred at a mild reflux for 1 hour and then at ambient for 1.5 hours. The resultant beige solid was collected by filtration and dried to yield 4.0 g. The product was recrystallized twice from ethanol to provide 2.7 g (27%) of 1-[4-[3-[4-(1-benzisothiazol-3-yl)-1-piperazinyl]propoxy]-3-methoxyphenyl]ethanone hemifumarate as a beige powder, m.p.=186°–188° C.

ANALYSIS

Calculated for $C_{23}H_{27}N_3O_3S.0.5\ C_4H_4O_4$: 62.09% C 6.06% H 8.69% N.

Found: 62.01% C 6.06% H 8.68% N.

EXAMPLE 38

1-[3,5-Dibromo-4-[3-[4-(6-fluoro-1,2-benzisoxazol-3-yl)-1-piperidinyl]propoxyphenyl]ethanone A stirred mixture of 6-fluoro-3-(4-piperidinyl)-1,2-benzisoxazole (2.0 g, 9.0 mmoles), $K_2CO_3$ (1.3 ), and 1-[4-(3-bromopropoxy)-3,5-dibromophenyl]ethanone (2.65 g, 9.0 mmoles) and acetonitrile (50 ml) was heated at reflux for 3 hr. At the end of the reaction, the solvent was evaporated and the residue was extracted into dichloromethane (150 ml). The insolubles were filtered off. The dichloromethane solution was concentrated down to an oil. The purification was done by flash chromatography on a silica gel column ($SiO_2$, 47 g; eluted with dichloromethane, 300 ml; 1% methanol in dichloromethane, 600 ml). The material thus purified as a colorless oil, solidified on standing. Recrystallization from ethanol gave 1-[3,5-dibromo-4-[3-[4-(6-fluoro-1,2-benzoisoxazol-3-yl)-1-piperidinyl) propoxy]phenyl]ethanone as white crystals (2.93 g, 57%), m.p. 102°–103° C.

ANALYSIS

Calculated for $C_{23}H_{23}Br_2FN_2O_3$; 49.84% C 4.18% H 5.05% N.

Found: 49.91% C4.11% H 4.98% N.

EXAMPLE 39

1-[4-[2-[4-(1,2-Benzisothiazol-3-yl)-1-piperazinyl] ethoxy]-3-methoxyphenyl]ethanone A mixture of 3-(1-piperazinyl)-1,2-benzisothiazole (4.0 g, 0.0182 mol), 1-[4-(2-chloroethoxy)-3-methoxyphenyl] ethanone (4.3 g, 0.0200 mol), $K_2CO_3$ (3.0 g, 0.0218 mol), acetonitrile (125 ml) and a catalytic amount of KI was heated to reflux and stirred under nitrogen for 24 hours. At this point, an additional amount of $K_2CO_3$ (1.0 g, 0.0072 mmol) and alkylating agent (0.4 g, 0.0017 mol) was added to the reaction mixture and heating at reflux was resumed for 24 hours. The reaction was cooled to ambient temperature and filtered. The filter cake was washed with acetonitrile and the filtrate was concentrated to afford a dark oil. The oil was extracted with methylene chloride, and the organic extract was washed with water, dried with $MgSO_4$ and concentrated to yield 9.2 g of an oil. Purification by preparative HPLC (Waters Associates Prep LC/System 500 utilizing 2 silica gel columns and 3% methanol/methylene chloride as eluent) provided 3.8 g of a soft, beige gum, which readily solidified. The compound was recrystallized twice from ethanol to give 2.1 g (28%) of 1-[4-[2-[4-(1,2-benzoisothiazol-3-yl)-1-piperazinyl]ethoxy]-3-methoxyphenyl]ethanone as a beige solid, m.p.=98°–100° C.

ANALYSIS

Calculated for $C_{22}H_{25}N_3O_3S$: 64.21% C 6.12% H 10.21% N.

Found: 64.05% C 6.09% H 10°–12% N.

EXAMPLE 40

6-Fluoro-3-[1-(3-phenoxypropyl)-4-piperidinyl]-1,2-benzisoxazole

A mixture of 6-fluoro-3-(4-piperidinyl)-1,2-benzoisoxazole (4.0 g, 0.0182 mol), $K_2CO_3$ (3.0 g, 0.0218 mol), KI (100 mg), 3-chloropropoxybenzene (3.4 g, 0.0200 mol), and acetonitrile was stirred at reflux under nitrogen for 30 hours. The reaction was poured into water and the aqueous mixture was extracted with ethyl acetate. The ethyl acetate extract was washed with brine, dried with $MgSO_4$ and concentrated to afford 6.2 g of a damp, beige solid. The compound was recrystallized twice from ethanol to yield (47%) of 6-fluoro-3-[1-(3-phenoxypropyl)-4-piperidinyl]-1,2-benzisoxazole as a light beige solid, m.p.=78°–80° C.

ANALYSIS

Calculated for $C_{21}H_{23}FN_2O_2$: 71.17% C 6.54% H 7.90% N.

Found: 71.00% C 6.52% H 7.81% N.

EXAMPLE 41

1-[4-[2-[4-(6-Chloro-1H-indazol-3-yl)-1-piperazinyl]ethoxy]-3-methoxyphenyl]ethanone A mixture of 6-chloro-[3-(1-piperazinyl)-1H-indazole (2.1 g, 0.0089 mol), $K_2$ $_{CO3}$ (1.5 g, 0.0107 mol), KI (100 mg), 1-[4-(2-chloroethoxy)-3-methoxyphenyl]ethanone (2.2 g, 0.0098 mol) and acetonitrile (70 ml) was stirred at reflux for 48 hours under $N_2$. The cooled reaction was poured into water and the aqueous mixture was extracted with ethyl acetate. The organic extract was washed with water, dried with $MgSO_4$ and concentrated to yield 6.0 g of a light yellow oil. The oil was purified by preparative HPLC (Waters Associates prep LC/System 500, employing 2 silica gel columns and 5.5% methanol/methylene chloride as eluent). Concentration of later fractions provided 1.6 g of an off-white solid. This was combined with an additional sample (3.4 g total) and two consecutive recrystallizations from ethanol yielded 2.1 g (23%) of 1-[4-[2-[4-(6-chloro-1H-indazol-3-yl)-1-piperazinyl]ethoxy]-3-methoxyphenyl] ethanone an off-white solid, m.p.=154°–156° C.

ANALYSIS

Calculated for $C_{22}H_{25}ClN_4O_3$: 61.61% C 5.88% H 13.06% N.

Found: 61.66% C 5.87% H 13.06% N.

EXAMPLE 42

1-[4-[3-[4-(6-Fluoro-1,2-benzisoxazol-3-yl)-1-piperidinyl]propoxy]-3-methoxyhenyl]-2,2,2-trifluoroethanone A mixture of 6-fluoro-3-(4-piperidinyl)-1,2-benzisoxazole (1.5 g, 0.0067 mol), 1-[4-(3-chloropropoxy)-3-methoxyphenyl]-2,2,2-trifluoroethanone (2.0 g, 0.0067 mol), $K_2CO_3$ (0.88 ), KI (0.1 ) and acetonitrile (50 ml) was stirred and refluxed for 16 h. After cooling, the reaction was poured into water and the aqueous mixture extracted with ethyl acetate. The extract was washed ($H_2O$), dried ($MgSO_4$), and the solvent was concentrated to an oil, which upon evacuation at high vacuum afforded 3.2 g of a waxy solid. The solid was chromatographed on a Waters preparative LC (silica columns, eluting with 3% methanol-dichloromethane). Concentration of the appropriate fractions gave 1.8 g (56%) of 1-[4-[3-[4-(6-fluoro-1,2-benzisoxazol-3-yl)-1-piperidinyl]propoxy]-3-methoxyphenyl]-2,2,2-trifluoroethanone solid, m.p.= 94°–96° C.

ANALYSIS

Calculated for $C_{24}H_{24}F_4N_2O_4$: 60.00% C 5.03% H 5.83% N.

Found: 60.01% C 5.06% H 5.68% N.

EXAMPLE 43

1-[4-8 3-[4-(6-Fluoro-1,2-benzisoxazol-3-yl]-1-piperidinyl]propoxy]-3-methylmercaptophenyl] ethanone A stirred mixture of 6-fluoro-3-(4-piperidinyl)-1,2-benzisoxazole (1.88 g, 8.5 mmoles), $K_2CO_3$ (1.8 g) and 1-[4-(3-bromopropoxy)-3-methylmercaptophenyl]ethanone (2.3 g, 7.6 mmole) in acetonitrile (100 ml) was heated at reflux for 4 hr. At the end of the reaction, the solvent was concentrated, then diluted with dichloromethane (250 ml). The insolubles were filtered off. The dichloromethane solution was concentrated to dryness as an oil. Purification was effected by flash chromatography on a silica gel column ($SiO_2$, 54 g, eluted with dichloromethane, 500 ml; 1% methanol:dichloromethane, 1.1 l). The purest fractions were combined to give a colorless oil which solidified to an off-white solid (2.4 g). Recrystallization from ethanol (100 ml) yielded 1-[4-[3-[4-(6-fluoro-1,2-benzoisoxazol-3-yl]-1-piperidinyl]propoxy]-3-methylmercaptophenyl]ethanone as off-white needle crystals, 2.15 g, m.p.=150°–152° C.

ANALYSIS

Calculated for $C_{24}H_{27}FN_2O_3S$: 65.14% C 6.15% H 6.33% N.

Found: 65.09% C 6.10% H 6.25% N.

EXAMPLE 44

1-[4-(3-Bromopropoxy)-3-bromophenyl]ethanone

A stirred mixture of 3-bromo-4-hydroxyacetophenone (4.5 g, 21.2 mmoles), $K_2CO_3$ (4 g) and 1,3-dibromopropane (7.6 g) in acetonitrile (200 ml) was heated at reflux for 2 hr. At the end of the reaction, the solvent was removed and the residue was dissolved in dichloromethane (400 ml) and filtered. The dichloromethane solution was concentrated to an oil. The oil was added to isopropyl ether and stirred to cause crystallization (4.1 g; 58%). The solid was recrystallized from isopropyl ether to give 3.5 g of 1-[4-(3-bromopropoxy)-3-bromophenyl]ethanone as glistening crystals, m.p.=83°–84° C.

ANALYSIS

Calculated for $C_{11}H_{12}Br_2O_2$: 39.31% C 3.60% H.

Found: 39.80% C 3.55% H.

EXAMPLE 45

1-[4-(3-Bromopropoxy)-3,5-dibromophenyl] ethanone

A stirred mixture of 3,5-dibromo-4-hydroxyacetophenone (3.0 g, 10.1 mmole), $K_2CO_3$ (2.8 g, 20.3 mmoles), 1,3-dibromopropane (4.0 g, 19.8 moles) in acetonitrile (100 ml) was heated at reflux for 5 hr. The solvent was removed. The crude product was extracted into dichloromethane (150 ml) and the insoluble inorganics were filtered off. The solution was concentrated to dryness again. Purification was carried out by flash chromatography on silica gel (45 g, $SiO_2$; eluted with 1:1 hexane:dichloromethane). The material thus obtained (2.8 g) was recrystallized twice from isopropyl ether to give analytically pure 1-[4-(3-bromopropoxy)-3,5-dibromophenyl]ethanone, m.p.=87°–88° C.

ANALYSIS

Calculated for $C_{11}H_{11}Br_3O_2$: 31.84% C 2.67% H.

Found: 31.97% C 2.63% H.

EXAMPLE 46

1-[4-[4-[4-(1,2-Benzisothiazol-3-yl)-1-piperidinyl] butoxy]-3-methoxyphenyl]ethanone A stirred mixture of 3-(4-piperidinyl)-1,2-benzisothiazole (2.6 g, 0.0119 mol), 1-[4-(4-bromobutoxy)-3-methoxyphenyl]ethanone (3.9 g, 0.0131 mol), $K_2CO_3$ (2.0 g, 0.0143 mol), KI (200 mg) and acetonitrile (125 ml) was stirred at reflux under nitrogen for 18 hours. The reaction was cooled to ambient temperature and filtered. The filter cake was washed well with fresh acetonitrile and the filtrate was concentrated to yield a wet, brown solid. The residue was diluted with water and the aqueous suspension was extracted with methylene chloride. The organic extract was washed with water, dried with $MgSO_4$ and concentrated to afford 6.5 g of a dark oil. The oil was purified by preparative HPLC (Waters Associates prep LC/System 500, utilizing 2 silica gel columns and 5% methanol/methylene chloride) to give 4.5 g of a beige solid. A 3.1 g (0.0071 mol) sample was taken up in absolute ethanol (80 ml) and oxalic acid (1.67 g, 0.0074 mol) was added. The solution was refluxed mildly on a stream bath for 45 minutes and was then stirred at ambient temperature for 1 hour. The resultant suspension was diluted with anhydrous ether (150 ml) and stirred for 5 minutes. The solid was collected and dried to afford 3.1 g of a light, beige solid. The salt was recrystallized from ethanol to yield 2.8 g. The compound was converted back to the free base with 50% NaOH to give 2.4 g, which was immediately recrystallized from ethanol to provide 1.5 g (29%) of 1-[4-[4-[4-(1,2-benzisothiazol-3-yl)-1-piperidinyl]butoxy]-3-methoxyphenyl]ethanone as a beige powder, m.p.=78°–80° C.

ANALYSIS

Calculated for $C_{25}H_{30}N_2O_3S$: 68.46% C 6.91% H 6.39% N.

Found: 68.34% C 6.85% H 6.33% N.

EXAMPLE 47

1-[4-[3-[4-(6-Fluoro-1,2-benzisoxazol-3-yl)-1-piperidinyl]propoxy]-3-methoxyphenyl] phenylmethanone A mixture of 6-fluoro-3-(4-piperidinyl)-1,2-benzisoxazole (2.2 g, 10 mmoles), $K_2CO_3$ (2.3 g) and 1-[4-(3-bromopropoxy)-3-methoxyphenyl] phenylmethanone (3.47 g, 10 mmoles) in acetonitrile (100 ml) was heated at reflux for 3 hours. At the end of reaction, the acetonitrile was concentrated and the mixture was extracted into dichloromethane (200 ml). The insolubles were filtered off and the solvent was evaporated to an oil. Purification was carried out by flash chromatography over a silica gel column ($SiO_2$, 50 g; eluted with dichloromethane, 600 ml; 1% methanol:dichloromethane, 600 ml; 2% methanol: 98% dichloromethane, 600 ml). The fractions containing the pure product were combined and concentrated to give 4.24 g (87%) of an off-white solid. Recrystallization from ethanol (75 ml) gave 3.9 g of 1-[4-[3-[4-(6-fluoro-1,2-benzoisoxazol-3-yl)-1-piperidinyl]propoxy]-3-methyoxyphenyl]phenylmethanone as off-white crystals, m.p.=128°–130° C.

ANALYSIS

Calculated for $C_{29}H_{29}FN_2O_4$: 71.30% C 5.98% H 5.73% N.

Found: 71.31% C 5.99% H 5.75% N.

EXAMPLE 48

1-[4-[3-[4-(6-Fluoro-1,2-benziosoxazol-3-yl)-1-piperidinyl]propoxy]-3-bromophenyl]ethanone A mixture of 6-fluoro-3-(4-piperidinyl)-1,2-benzisoxazole (2.1 g, 9.5 mmole), $K_2CO_3$ (2.0 g) 1-[3-bromo-4-(3-bromopropoxy)phenyl]ethanone (3.1 g, 9.2 mmoles) in acetonitrile (100 ml) was heated at reflux for 3 hours. At the end of reaction, the solvent was concentrated and the mixture was extracted into dichloromethane (200 ml). The insolubles were filtered off. The dichloromethane was concentrated again. The crude residue was purified by flash chromatography over a silica gel column ($SiO_2$, 49 g; eluted with dichloromethane, 500 ml; 1% methanol:dichloromethane, 600 ml; 3% methanol: 97% dichloromethane, 600 ml). The material thus obtained (3.26 g, 72%) was recrystallized from ethanol (40 ml) to give 1-[4-[3-[4-(6-fluoro-1,2-benzisoxazol-3-yl)-1-piperidinyl] propoxy]-3-bromophenyl]ethanone as light yellow crystals (3.0 ), m.p.=126°–128° C.

ANALYSIS

Calculated for $C_{23}H_{24}BrFN_2O_3$: 58.12% C 5.09% H 5.89% N.

Found: 57.64% C 5.35% H 5.55% N.

EXAMPLE 49

3-[1-[3-[4-(1-Ethoxyethyl)-2-methoxyphenoxy] propyl]-4-piperidinyl]-6-fluoro-1,2-benzisoxazole hydrochloride To a mixture of 4-[3-[4-(6-fluoro-1,2-benzisoxazole-3-yl)-1-piperidinyl]propoxy]-3-methoxy-α-methylbenzenemethanol (3.8 g, 0.089 mol) in pyridine (25 ml) was added acetic anhydride (5 ml). The mixture was warmed briefly on the steam bath to effect solution, and then the reaction was allowed to stand at ambient temperature for 16 hours. Most of the pyridine was evaporated under reduced pressure and the resultant oil was diluted with water. The aqueous solution was made basic with dilute NaOH, and subsequently extracted with ethyl acetate. The organic extract was washed (water), dried ($MgSO_4$), and the solvent concentrated to give 3.7 g of the O-acetyl derivative as a colorless oil. The compound was dissolved in diethyl ether and ethereal HCl was added to precipitate a gum-like hydrochloride salt, which upon treatment with refluxing ethyl acetate afforded 3.4 g of a crystalline salt, m.p. 143°–145° C. Attempting to recrystallize the salt from ethanol:diethyl ether resulted in displacement of the acetate to afford the ethyl ether. The salt of this product (2.8 g) was recrystallized from ethanol:diethyl ether to yield 2.1 g (48%) of 3-[1-[3-[4-(1-ethoxyethyl)-2-methoxyphenoxy]propyl]-4-piperidinyl]-6-fluoro-1,2-benzisoxazole hydrochloride, m.p.=139°–141° C.

ANALYSIS

Calculated for $C_{26}H_{33}FN_2O_4$.HCl: 63 . 34% C 6.95% H 5.68% N.

Found: 63.06% C 6.80% H 5.63% N.

EXAMPLE 50

3-[1-[3-[4-(1-Acetoxyethyl)-2-methoxyphenoxy]propyl]-4-piperidinyl]-6-fluoro-1,2-benzisoxazole fumarate A mixture of 4-[3-[4-(6-fluoro-1,2-benzisoxaol-3-yl)-1-piperidinyl]-3-methoxy-α-methylbenzenemethanol (4.8 g, 0.011 mol) in pyridine (45 ml) was warmed briefly to effect solution and then acetic anhydride (6.3 ml) was added. The reaction stood at ambient temperature for 16 hours, was concentrated in vacuo, and the colorless oil that remained was dissolved in water. The aqueous solution was made basic with saturated $K_2CO_3$ solution, and the mixture was extracted with diethyl ether. The extract was washed (water), dried ($MgSO_4$) and concentrated to afford 5.2 g of a thick, colorless oil. The oil (4.8 g) was dissolved in anhydrous diethyl ether and fumaric acid (1.2 g, 0.01 mol) was added. The mixture was stirred at ambient temperature for 4 hours, and then was permitted to stand at ambient temperature for 16 hours. The resultant white, 3-[1-[3-[4-(1-acetoxyethyl)-2-methoxyphenoxy]propyl]-4-piperidinyl]-6-fluoro-1,2benzisoxazole fumarate was collected and afforded 3.0 g of material. The filtrate was treated with an additional amount of fumaric acid (0.3 ) and 0.9 g more of 3-[1-[3-[4-(1-acetoxyethyl)-2-methoxyphenoxy]propyl]-4-piperidinyl]-6-fluoro-1,2-benzisoxazole fumarate was harvested. The two batches were combined and recrystallized from acetonitrile (twice) to yield 2.3 g (43%) of the acetate, m.p.=150°–152° C.

ANALYSIS

Calculated for $C_{26}H_{31}FN_2O_3.C_4H_4O_4$: 61.43% C 6.01% H 4.78% N.

Found: 61.06% C 5.87% H 4.73% N.

EXAMPLE 51

1-[4-[3-[4-(6-Fluoro-1,2-benzisoxazol-3-yl)-1-piperidinyl]propoxy]-3-methoxyphenyl]pentanone A mixture of 6-fluoro-3-(4-piperidinyl)-1,2-benzisoxazole (2.2 g, 0.01 mole), $K_2CO_3$ (3 g), 1-[4-(3-bromopropoxy)-3-methoxyphenyl]pentanone (3.7 g, 0.0113 mole) in acetonitrile (140 ml) was heated at reflux for 4 hours. At the end of the reaction, the mixture was cooled and filtered. The filtrate was concentrated to an oil. Purification was performed by flash chromatography over a silica gel column ($SiO_2$, 55 g; eluted with 1% methanol in dichloromethane, 600 ml; 3% methanol: 97% dichloromethane, 400 ml). The fractions containing pure product were pooled and concentrated to a solid (4.3 g, 91%). Recrystallization from ethanol (10 ml) gave a powdery solid of 1-[4-[3-[4-(6-fluoro-1,2-benzisoxazol-3-yl)-1-piperidinyl]propoxy]-3-methoxyphenyl]pentanone (3.22 ), m.p.=79°–80° C.

ANALYSIS

Calculated for $C_{27}H_{33}FN_2O_4$: 69.21% C 7.10% H 5.98% N.

Found: 69.00% C 6.94% H 6.39% N.

EXAMPLE 52

2-[3-[4-(6-Fluoro-1,2-benzisoxazol-3-yl)-1-piperidinyl]propoxy]-N-methylbenzenamine hemifumarate A mixture of 6-fluoro-3-(4-piperidinyl)-1,2-benzisoxazole (2.5 g, 0.0114 mol), $K_2CO_3$ (1.8 g, 0.0130 mol), 4-(3-chloropropoxy)-2-methylaminobenzene (2.4 g, 0.0120 mol) and acetonitrile (100 ml) was stirred at reflux for 18 hours. The reaction was cooled to ambient temperature and was poured into water. The aqueous mixture was extracted with ethyl acetate and the ethyl acetate extract was washed with water, dried with $MgSO_4$, and concentrated to yield 4.1 g of a brown oil. The oil was purified by preparative HPLC (Waters Associates prep LC/System 500, utilizing 2 silica gel columns and eluting with 4% methanol-methylene chloride). Concentration of appropriate fractions yielded 2.45 g of a beige oil. The product was taken up in ethyl acetate (50 ml) and fumaric acid (0.78 g) was added. The mixture was stirred at mild reflux for 45 minutes and then at ambient temperature for 1.5 hours. The product was isolated by vacuum filtration to provide 2.5 g of a pale yellow solid. Recrystallization from ethanol afforded 2.0 g (40%) of 2-[3-[4-(6-fluoro-1,2-benzisoxazol-3-yl)-1-piperidinyl]propoxy]-N-methylbenzenamine hemifumarate as beige crystals, m.p.=180°–182° C.

ANALYSIS

Calculated for $C_{22}H_{26}FN_3O_2.0.5C_4H_4O_4$: 65.28% C 6.40% H 9.52% N.

Found: 65.08% C 6.35% H 9.45% N.

EXAMPLE 53

1-[4-[3-[4-(6-Fluoro-1,2-benzisoxazol-3-yl)-1-piperidinyl]propoxy]-3-methoxyphenyl]propanone A mixture of 6-fluoro-3-(4-piperidinyl)-1,2-benzisoxazole (2.8 g, 15.2 mmoles), $K_2CO_3$ (3 ), 1-[4-(3-bromopropoxy)-3-methoxyphenyl]propanone (4.6 g, 18.2 mmoles) in acetonitrile (100 ml) was heated at reflux for 2 hours. At the end of the reaction, the mixture was filtered and the solvent was concentrated and the residue was extracted into dichloromethane (300 ml). The dichloromethane was filtered and concentrated again. The crude material (6.4 ) was purified by flash chromatography over a silica gel column ($SiO_2$, 50 g; eluted with dichloromethane, 700 ml; 1% methanol in dichloromethane, 1.4 l). The material thus purified (weight: 2.87 g, 51%) was recrystallized from ethanol (25 ml) to give 2.13 g of 1-[4-[3-[4-(6-fluoro-1,2-benzisoxazol-3-yl)-1-piperidinyl]propoxy]-3-methoxyphenyl]propanone as beige colored crystals, m.p.= 118°–119° C.

ANALYSIS

Calculated for $C_{25}H_{29}FNO_2O_4$: 68.16% C 6.64% H 6.36% N.

Found: 68.32% C 6.63% H 6.29% N.

EXAMPLE 54

4-[3-[4-(6-Fluoro-1,2-benzisoxazol-3-yl)-1-piperidinyl]-propoxy]-3-methoxybenzamide A mixture of 6-fluoro-3-(4-piperidinyl)-1,2-benzisoxazole (2.2 g, 10.0 mmoles), $K_2CO_3$ (2.0 g) and 4-(3-bromopropoxy)-3-methoxybenzamide (2.32 g, 8.0 moles) in acetonitrile (80 ml) was heated at reflux for 5 hours. At the end of the reaction the solvent was evaporated. The residue was extracted into dichloromethane. The inorganic insolubles were filtered off. The dichloromethane was concentrated again. The crude residue was purified by flash chromatography over a silica gel column (55 g, $SiO_2$; eluent with 1% methanol in dichloromethane, 1 l; 2% methanol in dichloromethane, 1 l). The material thus obtained weighed 2.93 g (84%) as white crystals. Recrystallization from the hot ethanol (60 ml) gave 2.2 g of 4-[3-[4-(6-fluoro-1,2-benzisoxazol-3-yl)-1-piperidinyl]propoxy]-3-methoxybenzamide as white crystals, m.p.=163°–164° C.

ANALYSIS

Calculated for $C_{23}H_{26}FN_3O_4$: 64.62% C 6.13% H 9.83% N.

Found: 64.20% C 6.06% H 9.71% N.

EXAMPLE 55

1-[4-[3-[4-(6-Fluoro-1,2-benzisoxazol-3-yl)-1-piperidinyl]propoxy-]-3-(methylamino)phenyl] ethanone A mixture of 6-fluoro-3-(4-piperidinyl)-1,2-benzisoxazole (2.3 g, 0.0103 mol), $K_2CO_3$ (1.4 g, 0.0103 mol), 1-[4-(3-chloropropoxy)-3-(methylamino)phenyl] ethanone (2.5 g, 0.0103 mol), KI(0.10), and acetonitrile (100 ml) was stirred at reflux under nitrogen for 23 hours. The reaction was cooled to ambient temperature, poured into water, and the aqueous mixture was extracted with ethyl acetate. The ethyl acetate extract was washed twice with water, dried with $MgSO_4$ and was concentrated to yield 4.8 g of a damp, brown solid. The compound was isolated by preparative HPLC (Waters Associates prep LC/System 500, utilizing 2 silica gel column and 4% methanol-methylene chloride as eluent). Concentration of appropriate fractions afforded 2.4 g. Recrystallization from ethanol gave 2.1 g of 1-[4-[3-[4-(6-fluoro-1,2-benzisoxazol-3-yl)-1-piperidinyl] propoxy]-3-(methylamino)phenyl]ethanone as a beige solid, m.p.=151°–153° C.

ANALYSIS

Calculated for $C_{24}H_{28}FN_3O_3$: 67.75% C 6.63% H 9.88% N.

Found: 67.83% C 6.76% H 9.90% N.

EXAMPLE 56

1-[4-[3-[4-(6-Fluoro-1,2-benzisoxazol-3-yl)-1-piperidinyl]propoxy]-3-ethoxyphenyl]ethanone A suspension of NaH (0.28 g of a 50% oil dispersion, 0.0059 mol) in dimethylformamide (20 ml) was cooled to 4° C. in an ice bath. To this was added, dropwise, 1-[4-[3-[4-(6-fluoro-1,2-benzisoxazol-3-yl)-1-piperidinyl]propoxy]-3-hydroxyphenyl]ethanone (2.3 g, 0.0056 mol) dissolved in dimethylformamide (40 ml). After total addition, the mixture was stirred under nitrogen for 1 hr. keeping the temperature below 10° C. A solution of bromoethane (1.3 g, 0.0118 mol) dissolved in dimethylformamide (15 ml) was then added, dropwise, to the reaction mixture. Stirring under nitrogen was continued for 3 hours allowing the temperature to slowly rise to ambient temperature. The reaction was cooled in an ice bath, water was added and the aqueous mixture was extracted with ethyl acetate. The ethyl acetate extract was washed with water, dried with $MgSO_4$, and was concentrated to yield 3.9 g of a damp, beige solid. The solid was triturated with diethyl ether and filtered to yield 1.5 g. This was combined with an additional sample (3.5 g total), and recrystallization from ethanol provided 3.0 g (57%) of glistening, beige crystals of 1-[4-[3-[4-(6-fluoro-1,2-benzisoxazol-3-yl)-1-piperidinyl]propoxy]-3-ethoxyphenyl] ethanone, m.p.=112°–114° C.

ANALYSIS

Calculated for $C_{25}H_{29}FN_2O_4$: 68.16% C 6.64% H 6.36% N.

Found: 68.10% C 7.03% H 6.35% N.

EXAMPLE 57

1-[4-(3-Bromopropoxy)-3-(methylmercapto)phenyl] ethanone

A mixture of 1-[4-hydroxy-3-(methylmercapto)phenyl] ethanone (5.4 g; 0.03 mole), $K_2COO_3$ (4.2 g), 1,3-dibromopropane (8 g, 0.039 mole) in acetonitrile (150 ml) was heated at reflux for 3 hours and stirred at room temperature overnight. Acetonitrile was removed at reduced pressure and the residue was extracted into dichloromethane (250 ml). Insolubles were filtered off. The dichloromethane solution was concentrated. The crude product was purified on a silica gel columns ($SiO_2$, 100 g; eluted with 3:2 hexane:dichloromethane, 1.6 l). The compound crystallized upon concentration, and the product (3.5 g, 39%) was recrystallized from ethanol (40 ml) to yield 1-[4-(3-bromopropoxy)-3-(methylmercapto)phenyl]ethanone as white needles, 2.0 g; m.p.=120°–122° C.

ANALYSIS

Calculated for $C_{12}H_{15}BrO_2S$: 47.53% C 4.99% H.

Found: 47.74% C 4.91% H.

EXAMPLE 58

4-(3-Bromopropoxy)-3-methoxybenzonitrile

A mixture of 4-hydroxy-3-methoxybenzonitrile (7.5 g, 50 mmoles), $K_2CO_3$ (12.5 ), and 1,3-dibromopropane (15 g, 75 moles) in acetonitrile (100 ml) was heated at reflux for 3 hours and left standing at room temperature overnight. The solvent of the reaction was removed on a rotary evaporator, and the crude solid was extracted into methylene chloride (500 ml). The insolubles were filtered off. The dichloromethane solution was concentrated and the material was purified on a flash chromatography columns ($SiO_2$, 105 g; eluted with 2:3 dichloromethane:hexane, and then with dichloromethane). The desired product thus purified weighed 7.74 g (52%). Recrystallization twice from ethanol gave analytically pure 4-(3-bromopropoxy)-3-methoxybenzonitrile, m.p.=99°–101° C.

ANALYSIS

Calculated for $C_{11}H_{12}BrNO_2$: 48.91% C 4.88% H 5.19% N.

Found: 49.49% C 4.47% H 5.21% N.

EXAMPLE 59

1-[4-(3-Bromopropoxy)-3-methylphenyl]ethanone

A mixture of 4-hydroxy-3-methylacetophenone (14.5 g, 96 moles), $K_2CO_3$ (17.5 g, 144 mmoles), and 1,3-dibromopropane (30 g, 144 mmoles) in acetonitrile ) 400 ml) was heated at reflux for 6 hours. At the end of the reaction, the solvent was removed on a rotary evaporator, and the crude solid was extracted into dichloromethane (750 ml). The insoluble inorganics were filtered off. The dichloromethane solution was concentrated again to a crude oil (34.5 g). Purification was effected by flash chromatography over a silica gel column ($SiO_2$, 150 g; eluted with 7:3 hexanes:dichloromethane, 2 l; and dichloromethane 2 l). The material thus purified weighted 14.6 g (56%) and was recrystallized from ethanol. Recrystallization again from ethanol gave analytically pure 1-[4-(3-bromopropoxy)-3-methylphenyl]ethanone, m.p.=59°–61° C.

ANALYSIS

Calculated for $C_{12}H_{15}BrO_2$: 53.15% C 5.58% H.

Found: 53.35% C 5.52% H.

EXAMPLE 60

1-[4-(3-Bromopropoxy)-3-methoxyphenyl] phenylmethanone

A mixture of 1-(4-hydroxy-3-methoxyphenyl) phenylmethanone (14 g, 61.4 mmoles), $K_2CO_3$ (13 g, 92.1 mmoles), and 1,3-dibromopropane (28 g, 86 moles) in acetonitrile (400 ml) was heated at reflux for 4 hours. The reaction was followed by thin layer chromatography. At the end of the reaction, the inorganics were filtered off and the solvent was removed on a rotary evaporator. The residue was purified on a flash chromatographic column ($SiO_2$, 140 g, eluted with 4:1 hexane:dichloromethane, 1.2 l) to give a partially solidified material: 15.44 g (72%). Recrystallization twice from ethanol gave 2.84 g of 1-[4-(3-bromopropoxy)-3-methoxyphenyl]phenylmethanone as white crystals, m.p.=88°–89° C.

ANALYSIS

Calculated for $C_{17}H_{17}BrO_3$: 58.74% C 4.91% H.

Found: 59.03% C 4.87% H.

EXAMPLE 61

N-[2-[3-[4-(6-fluoro-1,2-benzoisoxazol-3-yl)-1-piperidinyl]propoxy]phenyl]acetamide (A) N-[2-(3-phenylsulfonyloxypropxoy)phenyl] acetamide To a solution of N-2-[2-(3-hydroxypropoxy)phenyl] acetamide (Example 113) (7.5 g, 0,036 mol) in pyridine (90 ml), cooled to 0° C., was added p-toluenesulfonyl chloride (13.6 g, 0.056 mol). After the tosyl chloride went into solution, the reaction was then allowed to stand at 5° C. for 16 hours. The reaction was poured onto ice, and a brown oil settled. The aqueous supernatant was decanted from the oil, and the residual oil taken up in diethyl ether. The diethyl ether was washed with cold (5° C.) 3N HCl and then with brine. The organic layer was dried ($MgSO_4$), and concentrated to afford a thick, brown oil, 5.3 g.

(B) N-[2-[3-[4-(6-fluoro-1,2-benzisoxazol-3-yl)-1-piperidinyl]propoxy]phenyl]acetamide A mixture of 6-fluoro-3-(4-piperidinyl)-1,2-benzisoxazole (3.4 g, 0.016 mol), N-[2-(3-phenylsulfonyloxypropoxy)phenyl]acetamide (5.3 g, 0.016 mol), $K_2CO_3$ (2.2 g), and acetonitrile (50 ml) was stirred and refluxed for 5 hours. The reaction was poured into water, and the aqueous suspension was extracted with ethyl acetate. The ethyl acetate was washed (water and brine), dried ($MgSO_4$) and the solvent was concentrated to afford 6.0 g of a thick, brown oil. The oil was chromatographed on a Waters Prep 500 LC on silica gel. Concentration of the appropriate fractions afforded 3.0 g of a beige solid. This was recrystallized from ethyl acetate to yield (with concentration of the mother liquors) 2.2 g (33%) of N-[2-[3-[4-(6-fluoro-1,2-benzisoxazol-3-yl)-1-piperidinyl]propoxy]phenyl] acetamide as a beige solid, m.p.=118°–120° C.

ANALYSIS

Calculated for $C_{23}H_{26}FN_3O_3$: 67.14% C 6.37% H 10.21% N.

Found: 67.06% C 6.43% H 10.23% N.

EXAMPLE 62

1-[4-[3-[4-(6-Fluoro-1,2-benzisoxazol-3-yl)-1-piperidinyl]propoxy]-3-dimethylaminophenyl] ethanone (A) 1-[4-(3-Chloropropoxy)-3-dimethylaminophenyl]ethanone To a suspension of sodium hydride (2.3 g, 0.0485 mol of 50% oil dispersion) with dimethylformamide (75 ml), and cooled to 3° in an ice-salt bath and under a stream of nitrogen was added, dropwise, 1-(4-hydroxy-3-dimethylaminophenyl)ethanone (8.7 g, 0.0485 mol) dissolved in dimethylformamide (150 ml) so that the temperature did not go over 7°. After the addition was over, the bath was removed and the reaction was stirred at ambient temperature for 45 minutes. The ice bath was reapplied and a solution of 1-bromo-3-chloropropane (8.4 g, 0.0534 mol) in dimethylformamide (25 ml) was added dropwise. After the addition was complete, the reaction was stirred for 18 hours at ambient temperature under nitrogen. The reaction was chilled to 7° in an ice bath and water (200 ml) was carefully added. After stirring for 5 minutes, the aqueous mixture was extracted with ethyl acetate (5×200 ml). The ethyl acetate extract was washed with water (2×50 ml), dried with $MgSO_4$, and concentrated to yield 22.2 g of a black oily liquid. The compound was purified by prep HPLC, and combination of appropriate fractions gave 5.0 g of brown oil.

(B) 1-[4-[3-[4-(6-fluoro-1,2-benzisoxazol-3-yl>-1-piperidinyl]propoxy]-3-dimethylaminophenyl] ethanone A mixture of 1-[4-(3-chloropropoxy)-3-dimethylaminophenyl]ethanone (2.9 g, 0.0113 mol), 6-fluoro-3-(4-piperidinyl)-1,2-benzisoxazole (2.5 g, 0.0113 mol), $K_2CO_3$ (1.7 g, 0.0122 mol), KI (200 mg) and acetonitrile (125 ml) was stirred at reflux for 18 hours. The cooled reaction was poured into water and the aqueous mixture was extracted with ethyl acetate. The ethyl acetate extract was washed with water, dried with magnesium sulfate and concentrated to yield 5.3 g of an amber oil. The compound was purified by preparative HPLC (Waters Associates prep LC/System 500 utilizing 2 silica gel columns) and concentration of appropriate fractions provided 1.65 g (33%). After combining with two additional samples, the compound (3.4 g, 7.74 mmol total) was taken up in ethyl acetate and fumaric acid (0.90 g, 7.75 mmol) was added. The mixture was stirred at a mild reflux for 30 minutes and then for 1 hour at ambient temperature. The reaction was left to stand overnight and was then filtered to give 3.6 g. The compound was recrystallized twice from ethanol to provide 2.3 g and once from acetonitrile to yield 1.9 g of the compound as a fumarate salt.

The compound was converted to the free base by suspending it in dilute NaOH and extracting with dichloromethane. After washing the dichloromethane extract with water and drying with $MgSO_4$, the solvent was removed in vacuo to give 1.4 g (14%) of 1-[4-[3-[4-(6-fluoro-1,2-benzisoxazol-3-yl)-1-piperidinyl)propoxy]-3-dimethylaminophenyl] ethanone as a beige solid, m.p.=94°–96° C.

ANALYSIS

Calculated for $C_{25}H_{30}FN_3O_3$: 68.32% C 6.88% H 9.56% N.

Found: 67.74% C 6.74% H 9.40% N.

EXAMPLE 63

1-[4-[3-[4-(6-Fluoro-1,3-benzisoxazol-3-yl)-1-piperidinyl]propoxy]-2-methoxyphenyl]ethanone hydrochloride A mixture of 6-fluoro-3-(4-piperidinyl)-1,2-benzisoxazole (4.4 g, 0.02 mol), 1-[4-(3-chloropropoxy)-2-methoxyphenyl]ethanone (4.8 g, 0.02 mol), $K_2CO_3$ (2.8 ), KI (200 mg) and acetonitrile (110 ml) was stirred and refluxed for 16 hours. The reaction was filtered and the filtrate concentrated to afford 9.0 g of a brown oil. The oil was taken up in acetone and fumaric acid (2.5 g, 0.022 mol) was added. The mixture was heated to reflux and then it was stirred at ambient temperature for 1 hour. The resultant fumarate salt (7.0 g) was collected and then reversed to the free base with aqueous sodium hydroxide to afford 4.6 g of a soft solid. The solid was flash chromatographed on silica gel with dichloromethane-methanol (10%) as eluent, and after concentration of the appropriate fractions afforded 3.6 g of an off-white solid. The solid was dissolved in anhydrous ether and ethereal HCl was added to precipitate 3.3 g of the hydrochloride salt. The salt was recrystallized from ethanol to afford 3.3 g of product. Occluded alcohol was removed to yield 2.8 g (29%) of 1-[4-[3-[4-(6-fluoro-1,2-benzisoxazol-3-yl)-1-piperidinyl]propoxy]-2-methoxyphenyl]ethanone hydrochloride, m.p.=193°–195° C.

ANALYSIS

Calculated for $C_{24}H_{28}ClFN_2O_4$: 62.27% C 6.10% H 6.05% N.

Found: 61.88% C 5.90% H 5.96% N.

EXAMPLE 64

1-[4-(3-Chloropropoxy)-3-methoxyphenyl]-2,2,2-trifluoroethanone (A) 4-(3-Chloropropoxy]-3-methoxybenzoic acid To a stirred suspension under nitrogen of sodium hydride (6.4 g, 0.13 mol, of about 50% oil dispersion-ether washed) in tetrahydrofuran (220 ml) was added pyrazole (4.4 g, 0.06 mol) in tetrahydrofuran (60 ml), dropwise. After complete addition, the reaction was stirred for about 15 minutes, and then 4-(3-chloropropoxy)-3-methoxybenzaldehyde (24.5 g, 0.107 mol) was added. The nitrogen was stopped and air was sparged into the reactor for about 3 hours. The reaction was then allowed to stir at ambient temperature open to the atmosphere for 16 hours. Water was added, the reaction was cooled in an ice bath, and concentrated hydrochloric acid (25 ml) was added dropwise. More water was added and the yellow solid that separated was collected to afford 16.2 g of product. The filtrate was then extracted with ethyl acetate to afford an additional 9.3. The samples were combined and recrystallized from acetonitrile to yield 12.6 g of a light, yellow solid, m.p.=154°–156° C. A 4.0 g sample was recrystallized from acetonitrile to yield 2.6 g of a yellow solid. This was combined with 0.4 g from another sample and recrystallized again from acetonitrile with charcoal treatment to afford 2.0 g of 4-(3-chloropropoxy)-3-methoxy) benzoic acid as a yellow solid, m.p.=157°–159° C.

ANALYSIS

Calculated for $C_{11}H_{13}ClO_4$: 54.00% C 5.35% H.

Found: 54.65% C 5.34% H.

(B) 4-(3-Chloropropoxy)-3-methoxybenzoyl chloride

To a mixture of 4-(3-chloropropoxy)-3-methoxybenzoic acid (2.4 g, 0.01 mol) in dichloromethane (5 ml) was added thionyl chloride (0.9 ml, 0.012 mol) dissolved in dichloromethane (5 ml). The reaction was stirred and refluxed for 1 hour, and then the dichloromethane was removed in vacuo to leave a dark oil. The oil was triturated with hexane and the solid that formed while scratching with a glass rod was collected to afford 1.6 g of 4-(3-chloropropoxy)-3-methoxybenzoyl chloride, m.p.=60°–63° C.

(C) 1-[4-(3-Chloropropoxy)-3-methoxyphenyl]-2,2,2-trifluoroethanone

To a stirred mixture of 4-(3-chloropropoxy)-3-methoxybenzoyl chloride (10.0 g, 0.038 mol) in methylene chloride (55 ml) cooled to −70° C., there was condensed into a reactor bromotrifluoromethane (70 g, 0.047 mol). There was then added to the reactor hexamethylphosphoroustriamide (9.4 g, 0.041 mol) dissolved in dichloromethane (7 ml). The first 90% was added quite rapidly, and the remainder at a slower rate. After complete addition, the reaction was stirred at −70° C. to −65° C. for an additional hour. The reaction mixture was allowed to come to room temperature. An equal volume of hexane was added and the layers were separated. The lower layer was extracted with hexane and then with diethylether. The extracts were combined and concentrated to yield 5.6 g of a thick, colorless oil. The oil was chromatographed on a Waters Prep 500 LC utilizing two silica gel columns and eluting with 20% ethyl acetate-hexane. Concentration of appropriate fractions gave 2.7 g of a light oil, which after evacuation at high vacuum solidified to a waxy, white solid (2.4 ) of 1-[4-(3-chloropropoxy)-3-methoxyphenyl]-2,2,2-trifluoroethanone.

EXAMPLE 65

4-[3-[4-(6-Fluoro-1,2-benzisoxazol-3-yl)-1-piperidinyl]propoxy]-3-hydroxy-α-methylbenzene methanol (A) 1-[4-(3-chloropropoxy-3-hydroxyphenyl] ethanone A mixture of 1-[4-(3-chloropropoxy)-3-methoxyphenyl] ethanone (10.0 g, 0.0412 mol) and concentrated $H_2SO_4$ (50 ml) was stirred at 65° for 23 hours. The cooled reaction was poured into 250 g of ice and was stirred vigorously for 10 minutes. The aqueous mixture was extracted with dichloromethane ($CH_2Cl_2$) and the resultant dichloromethane extract was washed well with 5% sodium hydroxide. The basic phases were combined and washed with dichloromethane. The aqueous mixture was cooled in an ice bath and concentrated hydrochloric acid was added until a precipitate formed. The product was isolated by filtration and dried to yield 3.1 g of a light brown solid. This was combined with an additional sample (5.0 g total) and two consecutive recrystallizations from toluene provided 3.4 g (22%) of 1-[4-(3-chloropropoxy)-3-hydroxyphenyl] ethanone as a beige solid, m.p.=101°–103° C.

ANALYSIS

Calculated for $C_{11}H_{13}ClO_3$: 57.78% C 5.73% H.

Found: 58.17% C 5.66% H.

(B) 4-(3-chloropropoxy)-3-hydroxy-α-methylbenzene methanol

To a flask charged with sodium borohydride (1.5 g, 0.0394 mol) under nitrogen and chilled to 10° was added, slowly, a solution of 1-[4-(3-chloropropoxy)-3-hydroxyphenyl]ethanone (6.0 g, 0.0262 mol) dissolved in ethanol-tetrahydrofuran (120 ml, 2:1). After total addition, the ice bath was removed and the reaction was stirred at ambient temperature for 3 hours. An additional amount of sodium borohydride (0.2 g, 0.053 mol) was carefully added. After stirring at ambient temperature for one hour, the solvent was removed in vacuo. The resultant solid residue was diluted with water (100 ml) and left overnight. The product was isolated by vacuum filtration yielding 3.8 g. Two consecutive recrystallizations from toluene provided 3.3 g (55%) of 4-(3-chloropropoxy)-3-hydroxy-α-methylbenzene methanol as a light brown solid, m.p.=107°–109° C.

ANALYSIS

Calculated for $C_{11}H_{15}ClO_3$: 57.27% C 6.55% H.

Found: 57.60% C 6.43% H.

(C) 4-[3-[4-(6-fluoro-1,2-benzisoxazol-3-yl)-1-piperidinyl]propoxy]-3-hydroxy-α-methylenebenzene methanol A mixture of 6-fluoro-3-(4-piperidinyl)-1,2-benzisoxazole (4.3 g, 0.0195 mol), 4-(3-chloropropoxy)-3-hydroxy-α-methylbenzenemethanol (4.5 g, 0.0195 mol), KI (200 mg), $NaHCO_3$ (1.8 g, 0.0215 mol) and $CH_3CN$ (125 ml) was stirred at reflux under nitrogen for 24 hours. The cooled reaction was filtered and the filter cake was washed with $CH_3CN$. The filtrate was concentrated to afford an oily residue, which was partitioned between water and ethyl acetate. The ethyl acetate extract was washed with water, dried with $MgSO_4$, and concentrated to yield 8.6 g of a dark oil. The oil was purified by preparative HPLC (Waters Associates prep LC/system 500) to yield 5.0 g. The compound was recrystallized twice from ethanol to provide 3.9 g (49%) of 4-[3-[4-(6-fluoro-1,2-benzisoxazol-3-yl)-1-piperidinyl]propoxy]-3-hydroxy-α-methylbenzene methanol as a light beige solid, m.p.=142°–144° C.

ANALYSIS

Calculated for $C_{23}H_{27}FN_2O_4$: 66.65% C 6.57% H 6.76% N.

Found: 66.68% C 6.35% H 6.72% N.

EXAMPLE 66

2-[3-[4-(6-Fluoro-1,2-benzisoxazol-3-yl)-1-piperidinyl]propoxy]aniline dihydrochloride (A) 2-(3-chloropropoxy) aniline To a stirred suspension of sodium hydride (11.0 g, 0.23 mol of a 50% oil dispersion) in dimethylformamide (250 ml), under nitrogen, was added, dropwise, 2-aminophenol (25.0 g, 0.23 mol) dissolved in dimethylformamide (125 ml). After complete addition, the reaction was stirred at ambient temperature for 1 hour, and then it was cooled to 5° C. (ice bath). 3-Chloro-1-bromopropane (36.2 g, 0.23 mol) in dimethylformamide (50 ml) was added, dropwise, so that the temperature did not go above 8° C. The reaction was stirred for 4 hours and then permitted to stand at ambient temperature for 16 hours. The reaction was poured into water and extracted with ethyl acetate. The ethyl acetate was washed (water), dried ($MgSO_4$), and the solvent concentrated to afford 25.4 g of a reddish, dark oil. About 12.0 g of the oil was chromatographed on HPLC columns. Concentration of the largest fractions gave 5.4 g of 2-(3-chloropropoxy) aniline as an oil.

(B) 2-[3-[4-(6-fluoro-1,2-benzisoxazol-3-yl)-1-piperidinyl)propoxy]aniline dihydrochloride A mixture of 6-fluoro-3-(4-piperidinyl)-1,2-benzisoxazole (4.8 g, 0.022 mol), 2-(3-chloropropoxy) aniline (4.0 g, 0,022 mol), $K_2CO_3$ (4.1 g, 0,022 mol), KI (0.2 g), and acetonitrile (100 ml) was stirred and refluxed for 10 hours. The reaction was poured into water and the aqueous mixture was extracted with ethyl acetate. The extract was washed (water), dried ($MgSO_4$), and the solvent was concentrated to afford 9.0 g of a red solid. The solid was triturated with diethyl ether to yield 3.0 g of a beige solid. This sample was combined with a sample (1.1 g) from another run, and a hydrochloride salt was prepared by dissolving the free base in ethanol and then adding ethereal HCl. The resultant salt (3.5 g) was recrystallized twice from methanol-diethyl ether to afford 2.6 g (22%) of 2-[3-[4-(6-fluoro-1,2-benzisoxazol-3-yl)-1-piperidinyl)propoxy] aniline dihydrochloride as a brown solid, m.p.=253°–255° C.

ANALYSIS

Calculated for $C_{21}H_{24}FN_3O_2.2HCl$: 57.02% C 5.92% H 9.50% N.

Found: 56.68% C 5.71% H 9.53% N.

EXAMPLE 67

N-[5-Acetyl-2-[3-[4-(6-fluoro-1,2-benzisoxazol-3-yl)-1-piperidinyl]propoxy-]phenyl acetamide (A) Preparation of 1-[3-acetylamino-4-(3-chloropropoxyphenyl]ethanone A stirred mixture of 1-[3-acetylamino-4-hydroxyphenyl] ethanone (7.7 g, 0.04 mol), $K_2CO_3$ (5.7 ), 3-chloro-1-bromopropane (8.9 g, 0,056 mol) and acetone (100 ml) was refluxed for 16 h. The reaction was allowed to cool to ambient temperature and filtered. Concentration of the filtrate yielded 8.5 g of a white solid. The solid was recrystallized from toluene and then from ethanol to afford 6.5 g of an off-white solid. A 3.3 g sample of this material was flash chromatographed on silica gel with ethyl acetate as eluent. Concentration of the appropriate fractions afforded 2.8 g of a solid. The solid was recrystallized from toluene and then from ethanol-water to yield 2.2 g (51%) of a solid, m.p.=124°–126° C.

ANALYSIS

Calculated for $C_{13}H_{16}ClNO_3$: 57.89% C 5.98% H 5.19% N.

Found: 57.08% C 5.85% H 5.13% N.

(B) N-[5-acetyl-2-[3-[4-(6-fluoro-1,2-benzisoxazol-3-yl)-1-piperidinyl]propoxy]phenyl]acetamide A mixture of 6-fluoro-3-(4-piperidinyl)-1,2-benzisoxazole (4.4 g, 0.02 mol), 1-[3-acetylamino-4-(3chloropropoxy)phenyl]ethanone (5.5 g, 0.0205 mol), $K_2CO_3$(2.8 g), and acetonitrile (70 ml) was stirred and refluxed for 16 hours. The reaction was poured into water and the aqueous mixture was extracted with ethyl acetate.

The extract was washed (water), dried ($MgSO_4$), and then it was concentrated to afford9.5 g of a brown oil. The oil was taken up in ethyl acetate and ethereal HCl was added until the reaction was acidic. The crude, brown, hydrochloride salt, was collected (8.4 g), and was immediately converted to the free base with $NH_4OH$, to afford 5.4 g of the compound as a brown oil. The oil was chromatographed on a Waters Preparative HPLC utilizing silica gel columns Concentration of the appropriate fractions yielded 3.5 g of N-[5-acetyl-2-[3-[4-(6-fluoro-1,2-benzisoxazol-3-yl)-1-piperidinyl]propoxy]phenyl]acetamide as a white solid, m.p.=108°–110° C.

ANALYSIS

Calculated for $C_{25}H_{28}FN_3O_4$: 66.21% C 6.22% H 9.27% N.

Found: 66.12% C 6.25% H 9.27% N.

EXAMPLE 68

3-[1-[3-(4-Ethyl-3-methoxyphenoxy)propyl]-4-piperidinyl]6-fluoro-1,2-benzisoxazole hydrochloride (A) 4-ethyl-2-methoxyphenol Acetovanillone (Aldrich, 11.0 g, 0.066 mol) was dissolved in absolute ethanol (200 ml) and added to 1.5 g of 5% palladium on carbon. A few drops of concentrated hydrochloric acid were added and the mixture hydrogenated on a shaker at 42 psi. The reaction mixture was filtered through celite, and the filtrate was concentrated to afford 10.3 g of a golden liquid. This was diluted with water, extracted with diethyl ether and the organic phase was washed with water and sodium bicarbonate. The solvent was dried ($MgSO_4$) and concentrated to afford 9.3 g of a slightly yellow liquid.

(B) 4-ethyl-2-methoxy-4-(3-chloropropoxy)benzene

A mixture of 4-ethyl-2-methoxyphenyl (9.0 g, 0.059 mol), 3-chloro-1-bromopropane (13.0 g, 0.083 mol), $K_2CO_3$ (6.2 g) and acetone (200 ml) was stirred and refluxed for 16 hours. The reaction was allowed to cool, and then it was filtered. The filtrate was concentrated to a clear liquid. The liquid was diluted with dilute aqueous NaOH, and the basic mixture was extracted with diethyl ether. The diethyl ether was washed (water), dried ($MgSO_4$), and the solvent was concentrated to afford 11.9 g of a golden liquid. The liquid was flash chromatographed. This gave a colorless liquid, 9.9 g of 4-ethyl-2-methoxy-4-(3-chloropropoxy)benzene.

(C) 3-[1-[3-(4-ethyl-2-methoxyphenoxy)propyl]-4-piperidinyl-6-fluoro-1,2-benzisoxazole hydrochloride A stirred mixture of 6-fluoro-3-(4-piperidinyl)-1,2-benzisoxazole (4.0 g, 0.018 mol), KI (0.4), $K_2CO_3$ (2.5 ), 4-ethyl-2-methoxy-4-(3-chloropropoxy)benzene (4.4 g, 0.018 mol) and acetonitrile was refluxed for 8 hours. The reaction was poured into water, and the aqueous suspension was extracted with ethyl acetate. The ethyl acetate extract was washed (water) dried ($MgSO_4$) and the solvent concentrated to afford 7.0 g of a brown oil. The oil was combined with 2.0 g from another sample, and the combined sample was flash chromatographed on silica gel. Concentration of the appropriate fractions yielded 4.4 g of a thick oil, which solidified on standing. The solid was dissolved in ethyl acetate and ethereal HCl was added to precipitate 4.5 g of a white hydrochloride salt. Recrystallization from acetone afforded 3.0 g (29%) of 3-[1-[3-(4-ethyl-2-methoxyphenoxy)propyl-]4-piperidinyl-6-fluoro-1,2-benzisoxazole hydrochloride as a white solid, m.p.=150°–152° C.

ANALYSIS

Calculated for $C_{24}H_{29}FN_2O_3$.HCl: 64.21% C 6.74% H 6.24% N.

Found: 64.38% C 6.84% H 6.14% N.

EXAMPLE 69

1-[3,5-Dimethoxy-4-[3-[4-(6-fluoro-1,2-benzisoxazol-3-yl)-1-piperidinyl]propoxy]phenyl] ethanone (A) 3,5-dimethoxy-4-(3-bromopropoxy) acetophenone To 3,5-dimethoxy-4-hydroxyacetophenone (5.2 ) in dimethylformamide (50 ml) at 0° C. under nitrogen, was added sodium hydride (700 mg, 1.1 eq, 98%). The resulting mixture was stirred for ten minutes until evolution of gas ceased. Potassium carbonate (4 g) was added, and then 1,3-dibromopropane was added. The mixture was heated at 60° C. for one hour. When the reaction was complete, the mixture was poured into a water/ice mixture and the resulting solution was extracted with ethyl acetate (600 ml). The ethyl acetate was washed with water, brine, and then concentrated to an oil (9 g). The product was purified by chromatography on silica gel to yield 3,5-dimethoxy-4-(3-bromopropoxy)acetophenone as a liquid oil, 7.6 g.

(B) 1-[3,5-dimethoxy-4-[3-[4-(6-fluoro-1,2-benzisoxazol-3-yl)-1-piperidinyl]propoxy]phenyl] ethanone A stirred mixture of 6-fluoro-3-(4-piperidinyl)-1,2-benzisoxazole (3.0 g, 13.6 moles), $K_2CO_3$ (2.1 g, 15 mmoles), and 3,5-dimethoxy-4-(3-bromopropoxy) acetophenone (4.4 g, 13.8 moles) in acetonitrile (50 ml) was heated at reflux for 3 hr. At the end of the reaction, the mixture was diluted with dichloromethane (200 ml). The insolubles were filtered. The solution was concentrated to an oil (~10). The purification was done by flash chromatography on a silica gel column. The product was obtained as a colorless oil (3.85 g, 61%), which crystallized from ethanol (400 ml) to give 2.94 g of 1-[3,5-dimethoxy-4-[3-[4-(6-fluoro-1,2-benzoisoxazol-3-yl)-1-piperidinyl]propoxy] phenyl]ethanone as off-white crystals, m.p.=107°–108° C.

ANALYSIS

Calculated for $C_{25}H_{29}FN_2O_5$: 65.78% C 6.40% H 6.14% N.

Found: 65.84% C 6.44% H 6.15% N.

EXAMPLE 70

N-[3-[3-[4-(6-Fluoro-1,2benzisoxazol-3-yl)-1-piperidinyl]propoxy]phenyl]acetamide hemifumarate (A) 3-(3-acetamidophenoxy)propyl bromide To 3-acetamidophenol (15.1 g) in dichloromethane (500 ml, dry) was added potassium carbonate (20 g) and then 1,3-dibromopropane (30 g). The resulting mixture was heated at reflux for 6 hours and then overnight at room temperature. After an additional 24 hours, the reaction was complete. Solids were filtered from the reaction mixture, and the solution was concentrated to an oil, which was purified to yield 3-(3-acetamidophenoxy)propyl bromide, 13.2 g.

(B) N-[3-[3-[4-(6-fluoro-1,2-benzisoxazol-3-yl)-1-piperidinyl]propoxy]phenyl]acetamide hemifumarate A stirred mixture of 6-fluoro-3-(4-piperidinyl)-1,2-benzisoxazol (9.25 g, 42 moles), $K_2CO_3$ (8 g, 58 moles) and 3-(3-acetamidophenoxy)propyl bromide (11.4 g, 42 mmoles) in acetonitrile (350 ml) was heated at reflux for 3 hours. At the end of the reaction, the reaction was cooled, filtered and the solids washed with dichloromethane (100 ml). The organic solvent was removed on a rotary evaporator to leave a crude oil ([18] 18 g). Purification was by flash chromatography on a silica gel column. The product thus purified was an oil, 12.2 g, 70%. Analytically pure sample was prepared by dissolving 3 g of free base in ethanol and treating with fumaric acid solution in ethanol (850 mg:5 ml). The N-[3-[3-[4-(6-fluoro-1,2-benzisoxazol-3-yl)-1-piperidinyl]propoxy]phenyl]acetamide hemifumarate crystals obtained weighed 2.73 g, m.p.=184°–186° C.

ANALYSIS

Calculated for $C_{23}H_{26}FN_3O_2.0.5C_4H_4O_4$: 63.95% C 6.01% H 8.94% N.

Found: 63.47% C 5.94% H 8.78% N.

EXAMPLE 71

3-[3-[4-(6-Fluoro-1,2-benzisoxazol-3-yl)-1-piperidinyl]propoxy]aniline

A stirred mixture of N-[3-[3-[4-(6-fluoro-1,2-benzisoxazol-3-yl)-1-piperidinyl]propoxyl]phenyl] acetamide (9.2 g, 22 moles), prepared as described in the previous example, in 15% hydrochloric acid (110 ml) was heated at 100° C. for 2.5 hours until a homogeneous solution resulted. The reaction was cooled to 0° C. in an ice bath and basified with 50% NaOH. The product was extracted with ethyl acetate (3×200 ml). The ethyl acetate solution was washed with water, brine, then dried over $Na_2SO_4$. The solvent was removed. The crude product was purified on a flash chromatography column. The product thus obtained was a solid: 6.6 g (80%). Recrystallization from hot ethanol (50 ml) gave 3-[3-[4-(6-fluoro-1,2-benzisoxazol-3-yl)-1-piperidinyl]propoxy]aniline as off-white crystals: 3.46 g, m.p.=115°–117° C.

ANALYSIS

Calculated for $C_{21}H_{24}FN_3O_2$: 68.27% C 6.55% H 11.37% N.

Found: 68.34% C 6.53% H 11.31% N.

EXAMPLE 72

3-[3-[4-(6-Fluoro-1,2-benzisoxazol-3-yl)-1-piperidinyl]propoxy]-4-methoxyaniline A mixture of 3-[3-[4-(6-fluoro-1,2-benzisoxazol-3-yl)-1-piperidinyl]propoxy]-4-methoxyphenylacetamide (4.2 g, 9.5 mmoles), prepared as in Example 26 above, in 15% hydrochloric acid (60 ml) was heated at reflux (~110° C.) for 2 hours. At the end of the reaction, the solution was cooled to 0° C. then basified with 25% NaOH to pH of 10. The product was extracted into ethyl acetate (300 ml). The ethyl acetate solution was washed with water and brine, then dried over $Na_2SO_4$. The solvent was removed at reduced pressure. The crude oil was purified by flash chromatography on a silica gel column. The product thus purified was an oil, 2.6 g. Crystallization from ethanol (5 ml) and petroleum ether (3 ml) yielded 3-[3-[4-(6-fluoro-1,2-benzisoxazol-3-yl)-1-piperidinyl]propoxy]-4-methoxyaniline as fine crystals: 1.2 g; m.p.=94°–95° C.

ANALYSIS

Calculated for $C_{22}H_{26}FN_3O_3$: 66.15% C 6.56% H 10.52% N.

Found: 66.16% C 6.54% H 10.44% N.

EXAMPLE 73

1-[3-[4-(6-Fluoro-1,2-benzisothiazol-3-yl)-1-piperidinyl]propoxy]-3-methylaminophenyl] ethanone fumarate (A) 1-[(3-N-acetyl-N-methylamino)-4-hydroxyphenyl]ethanone A solution of 2-methoxy(methylamino)benzene (26.0 g, 0.19 mol) and 1,2-dichloroethane was cooled to 10°–15° and a solution of acetyl chloride (33.8 g, 0.43 mol) dissolved in dichloroethane (50 ml) was dripped in slowly. Following this addition, an additional 100 ml dichloroethane was added. The reaction was cooled to 0° and aluminum chloride (72.3 g, 0.54 mol) was added over the course of 45 minutes so that the temperature did not exceed 10°. After complete addition, the reaction was heated to reflux and was stirred for 18 hours under nitrogen. The reaction was cooled and was poured into ice. The resulting aqueous phase was extracted further with dichloromethane and the combined extracts were washed with $H_2O$, dried with $MgSO_4$, and concentrated to yield 32.0 g of 1-[(3-N-acetyl-N-methylamino)-4-hydroxyphenyl]ethanone as a brown solid, m.p.=168°–171° C.

(B) 1-(4-hydroxy-3-methylaminophenyl]ethanone

A mixture of 1-((3-N-acetyl-N-methylamino)-4-hydroxyphenyl]ethanone (15.0 g, 0.0724 mol) and concentrated HCl (150 ml) was stirred at reflux for 3 hours. The heat was terminated and the reaction stood overnight. The reaction mixture was transferred to a 1 l beaker and was chilled in an ice-salt bath. Solid sodium bicarbonate was added cautiously until the pH was about 2, and the aqueous mixture was allowed to stand overnight. The reaction mixture was continued to be made basic by the addition of solid sodium bicarbonate. After pH 8 was achieved, the reaction mixture was extracted with ethyl acetate. The ethyl acetate extract was washed with a 200 ml aliquot of water and this was then fed through a bed of celite. After washing the cake with fresh ethyl acetate the phases were separated. The ethyl acetate extract was washed several more times with water, dried with $MgSO_4$ and concentrated to yield 10.5 g of a dark solid of 1-(4-hydroxy-3-methylaminophenyl)ethanone.

(C) 1-[4-(3-chloropropoxy)-3-methylaminophenyl] ethanone

To a stirred suspension of sodium hydride (0.87 g, 0.0182 mol of a 50% oil dispersion) in dimethylformamide (25 ml) under nitrogen and cooled to 0° in an ice-salt bath was added, dropwise, a solution of 1-(4-hydroxy-3-methylaminophenyl)ethanone (3.0 g, 0.0182 mol) dissolved in dimethylformamide (55 ml) so that the temperature did not rise above 3°. After the addition was complete, the reaction was stirred for 80 minutes at ambient temperature. The reaction was cooled to 5° and a solution of 1-bromo-3-chloropropane (3.1 g, 0.0120 mol) in dimethylformamide (20 ml) was added dropwise. After this addition was complete, the ice bath was removed and the reaction was stirred at ambient temperature for 2.5 hours. Water (75 ml) was carefully added and after stirring vigorously for 5 minutes, the reaction was left to stand overnight. The aqueous mixture was extracted with ethyl acetate and the ethyl acetate extract was washed with water, dried with $MgSO_4$, and concentrated to yield 3.9 g of a dark solid. The compound was purified by preparative HPLC to afford 2.4 g of a beige solid. This was combined with an additional sample (3.8 g total) and two consecutive recrystallizations from ethanol gave 2.1 g (31%) of 1-[4-(3-chloropropoxy)-3-methylaminophenyl]ethanone as a fluffy, beige solid, m.p.=115°–117° C.

ANALYSIS

Calculated for $C_{12}H_{16}C_{16}ClNO_2$: 59.63% C 6.67% H 5.79% N.

Found: 59.49% C 6.64% H 5.79% N.

(D) 1-[4-[3-[4-(6-fluoro-1,2-benzisothiazol-3-yl)-1-piperidinyl]propoxy-3-methylaminophenyl]ethanone fumarate A stirred mixture of 6-fluoro-3-(4-piperidinyl)-1,2-benzisothiazole (1.9 g, 0.079 mol), 1-[4-(3-chloropropoxy)-3methylaminophenyl]ethanone (1.9 g, 0.079 mol), $K_2CO_3$ (1.1 g), KI (0.1 g), and acetonitrile (95 ml) was refluxed for 16 hours. The reaction was poured into water and the aqueous suspension extracted with ethyl acetate. The extract was washed (water and brine), dried ($MgSO_4$), and then the solvent was concentrated to afford 3.2 g of a thick, brown oil. The oil was chromatographed on a Waters Prep 500 LC on silica gel columns, and concentration of the appropriate fractions afforded 1.5 g of a brown oil. The oil was dissolved in acetone and fumaric acid (0.4 g, 0.003 mol) was added, and 1.9 g of a white fumaric salt was collected. The salt was recrystallized from dimethylformamide to yield 1.1 g (25%) of 1-[4-[3-[4-(6-fluoro-1,2-benzisothiazol-3-yl)-1-piperidinyl]propoxy-3-methylaminophenyl]ethanone fumarate as a white solid, m.p.=98°–200° C.

ANALYSIS

Calculated for $C_{28}H_{32}FN_3O_6S$: 60.31% C 5.78% H 7.54% N.

Found: 60.02% C 5.88% H 7.68% N.

EXAMPLE 74

N-[3-[3-[4-(6-Fluoro-1,2-benzisothiazol-3-yl)-1-piperidinyl]propoxy]-4-methoxyphenyl]acetamide (A) N-[3-(3-chloropropoxy)-4-methoxyphenyl] acetamide To a stirred suspension, under nitrogen, of sodium hydride (1.8 g, 0.038 mol) in dimethylformamide (60 ml) was added dropwise, N-(3-hydroxy-4-methoxy)acetamide (6.1 g, 0.034 mol) dissolved in dimethylformamide (23 ml). After complete addition, the reaction was stirred at ambient temperature for 0.5 hour, and then 3-chloro-1-bromopropane (5.2 g, 0.033 mol) in dimethylformamide (10 ml) was added, dropwise. The reaction was stirred at ambient temperature for 16 hours, and then it was poured into water, and the aqueous mixture was extracted with ethyl acetate. The extract was washed (water), dried ($MgSO_4$) and the solvent concentrated to afford a purple solid. The solid was triturated with diethyl ether and collected to afford 2.8 g of a purple solid. This sample was combined with a sample (1.2 g) from another run and was recrystallized from toluene twice to yield 2.9 g of an off-white solid. The solid was flash chromatographed on a 200 g of silica gel, eluting the column with ethyl acetate, and subsequent concentration of the appropriate fractions afforded 2.4 g of a white solid. Recrystallized of the compound from toluene yielded 2.3 g (17%) of N-[3-(3-chloropropoxy-4-methoxyphenyl]acetamide, m.p.=112°–114° C.

ANALYSIS

Calculated for $C_{12}H_{16}ClN_3$; 55.93% C 6.26% H 5.44% N.

Found: 56.25% C 6.29% H 5.44% N.

(B) N-[3-[3-[4-(6-fluoro-1,2-benzisothiazol-3-yl)-1-piperidinyl]propoxy]-4-methoxyphenyl]acetamide A stirred mixture of 6-fluoro-3-(4-piperidinyl)-1,2-benzisothiazole (4.0 g, 0,017 mol), N-[3-(3-chloropropoxy)-4-methoxyphenyl]acetamide (4.3 g, 0.017 mol), $K_2CO_3$ (2.3 g), KI (0.2 g) and acetonitrile (200 ml) was refluxed for 10 hours. The cooled reaction mixture was filtered and the filtrate was concentrated to yield a dark oil. The oil was dissolved in acetone, and ethereal HCl was added to yield 5.7 g of a yellow hydrochloride salt. The salt was reversed to the free base and the resultant oil (5.2 g) was chromatographed on a Waters Associates Prep LC utilizing silica gel columns. Concentration of the appropriate fractions yielded 4.7 g of an oil, which was converted to a hydrochloride salt. The salt was converted to its free base yielding 2.8 g of a brown oil. The oil was stirred vigorously with ether to yield 1.4 g (18%) of N-[3-[3-[4-(6-fluoro-1,2-benzoisothiazol-3-yl)-1-piperidinyl]propoxy]-4-methoxyphenyl]acetamide as a white solid, 1.4 g, m.p.=109°–111° C.

ANALYSIS

Calculated for $C_{24}H_{28}FN_3O_3S$: 63.00% C 6.17% H 9.18% N.

Found: 62.80% C 6.17% H 8.86% N.

EXAMPLE 75

1-[4-[3-[4-(6-Fluoro-1,2-benzisothiazol-3-yl)-1-piperidinyl]propoxy]-3-methoxyphenyl]ethanone hydrochloride A stirred mixture of 6-fluoro-3-(4-piperidinyl)-1,2-benzisothiazole (4.0 g, 0.017 mol), 1-[4-(3-chloropropoxy)-3-methoxyphenyl]ethanone (4.1 g, 0,017 mol), $K_2CO_3$ (2.3 g), KI (0.2 g), and acetonitrile (100 ml) was refluxed for 9 hours. The reaction was poured into water, and the aqueous mixture was extracted with ethyl acetate. The extract was washed (water), dried ($MgSO_4$), and the solvent was concentrated to afford 8.0 g of a brown oil. The oil was chromatographed on a Waters Prep 500 HPLC on silica gel columns. Concentration of the appropriate fractions afforded a gum-like residue, which upon triburation with isopropyl ether afforded 1.9 g of a white solid. The solid was dissolved in absolute ethanol, and ethereal HCl was added to precipitate 1.7 g of a hydrochloride salt. Concentration of the isopropyl ether filtrate, and similar treatment of the residue, afforded an additional 0.5 g of the salt. The samples were combined and recrystallized from absolute ethanol to yield 1.7 g (21%) of 1-[4-[3-[4-(6-fluoro-1,2-benzisothiazol-3-yl)-1-piperidinyl]propoxy]-3-methoxyphenyl]ethanone hydrochloride as a white solid, m.p.=221°–223° C.

ANALYSIS

Calculated for $C_{24}H_{27}FN_2O_3S.HCl$: 60.18% C 5.89% H 5.85% N.

Found: 60.01% C 5.97% H 5.79% N.

EXAMPLE 76

N,N-Dimethyl-4-[3-[4-(6-fluoro-1,2-benzoisoxazol-3-yl)-1-piperidinyl]propoxy]-3-methoxybenzamide (A) N,N-dimethyl-4-bromopropoxy-3-methoxybenzamide To N,N-dimethyl-4-hydroxy-3-methoxybenzamide (5.64 g, 28.7 mmol) in acetonitrile (450 ml) was added potassium carbonate (7.9 g) followed by 1,3-dibromopropane (11.6 g). The resulting reaction mixture was refluxed for 3 hours and stirred at room temperature for 12 hours. The mixture was filtered and concentrated to an oil. Following purification by column chromatography, N,N-dimethyl-4-bromopropoxy-3-methoxybenzamide as a colorless oil (7.6 g) was obtained.

(B) N,N-dimethyl-4-[3-[4-(6-fluoro-1,2-benzisoxazol-3-yl)-1-piperidinyl]propoxy]-3-methoxybenzamide A stirred mixture of 6-fluoro-3-(4-piperidinyl)-1,2-benzoisoxazole (3.9 g, 17.7 moles), N,N-dimethyl-4-bromopropoxy-3-methoxybenzamide (5.54 g, 17.5 mmoles) and $K_2CO_3$ (3 g) in acetonitrile (250 ml) was heated at reflux for one hour. At the end of the reaction, the insolubles were filtered and washed with dichloromethane. The solvent was removed on a rotary evaporator. The residue was purified by flash chromatography over a silica gel column. The product thus obtained as an oil weighted 7 . Crystallization from hot ethanol (45 ml) afforded analytically pure N,N-dimethyl-4-[3-[4-(6-fluoro-1,2-benzisoxazol-3-yl)-1-piperidinyl]-propoxy]-3-methoxybenzamide, 3.95 g, 50%, as light yellow crystals, m.p.=126°–127° C.

ANALYSIS

Calculated for $C_{25}H_{30}FN_3O_4$: 65.92% C 6.64% H 9.22% N.

Found: 65.76% C 6.64% H 9.14% N.

EXAMPLE 77

1-[4-[3-[4-(6-Fluoro-1,2-benzoisoxazol-3-yl)-1-piperidinyl]propoxy]-3-methoxyphenyl]ethanone oxime A mixture of 1-[4-[3-[4-(6-fluoro-1,2-benzoisoxazol-3yl)-1-piperidinyl]propoxy]-3-methoxyphenyl]ethanone (4.3 g, 0.01 mol), prepared as in Example 3 above, hydroxylamine hydrochloride (1.3 g, 0.018 mol), ammonium acetate (1.7 g, 0.022 mol) and ethanol-$H_2O$ was stirred and refluxed for 16 hours. The reaction was poured into water, and the mixture was cooled in an ice bath for 2 hours. The resultant, whether solid was collected, washed with water and dried to yield 4.6 g of hydrochloride salt of the oxime, m.p. 216°–218° C. The compound was dispersed in water and ammonium hydroxide was added until the suspension was decidedly basic. The basic suspension was then extracted with dichloromethane, and after washing with water, drying ($MgSO_4$), and concentrating the extract, 3.0 g of white solid melting at 168°–170° C. were harvested. The compound was recrystallized from dimethylformamide to yield 2.3 g (52%) of 1-[4-[3-[4-(6-fluoro-1,2-benzisoxazol-3-yl)-1-piperidinyl]propoxy]-3-methoxyphenyl]ethanone oxime as a white solid, m.p.=168°–170° C.

ANALYSIS

Calculated for $C_{24}H_{28}FN_3O_4$: 65.29% C 6.39% H 9.52% N.

Found: 65.27% C 6.44% H 9.46% N.

EXAMPLE 78

1-[4-[3-[4-(6-Fluoro-1,2-benzisoxazol-3-yl)-1-piperidinyl]propoxy]methoxyphenyl]ethanone oxime O-methyl ether A solution of 1-[4-[3-[4-(6-fluoro-1,2-benzisoxazol-3-yl)-1-piperidinyl]propoxy]methoxyphenyl]ethanone (4.3 g, 0.01 mol), prepared as in Example 3 above, methoxylamine hydrochloride (0.93 g, 0.01 mol) in pyridine (75 ml)/ethanol (75 mg) was refluxed for 16 hours. Most of the solvent was evaporated under reduced pressure, and the residue was diluted with water to precipitate 1.6 g of a white solid, m.p. 200°–201° C. The aqueous filtrate upon standing deposited another crop of white crystals, which yielded 1.2 g of a pale, yellow solid with a m.p. of 70°–72° C. The initial crop of crystals was converted to its free base with aqueous NaOH. After extractive workup with ethyl acetate, 1.2 g of the free base was obtained. The two samples were combined and recrystallized from isopropyl ether to afford 2.0 g (44%) of 1-[4-[3-[4-(6-fluoro-1,2-benzisoxazol-3-yl)-1-piperidinyl]propoxy]methoxyphenyl]ethanone oxime O-methyl ether as colorless crystals, m.p.=97°–99° C.

ANALYSIS

Calculated for $C_{25}H_{30}FN_3O_4$: 65.92% C 6.64% H 9.22% N.

Found: 65.89% C 6.86% H 9.15% N.

EXAMPLE 79

1-[4-[3-[4-(6-Fluoro-1,2-benzisoxazol-3-yl)-1-piperidinyl]propoxy]-3-methoxyphenyl]ethanone hydrazone A stirred mixture of 1-[4-[3-[4-(6-fluoro-1,2-benzisoxazol-3-yl)-1-piperidinyl]propoxy]-3-methoxyphenyl]ethanone (4.3 g, 0.01 mol), prepared as in Example 3 above, hydrazine (0.8 g, 0.0025 mol), and ethanol (40 ml) was refluxed for 16 hours. The cooled solution was concentrated to yield an oily residue. The residue was triturated with water and the resultant solid was collected to afford 4.2 g of 1-[4-[3-[4-(6-fluoro-1,2-benzisoxazol-3-yl)-1-piperidinyl]propoxy]-3-methoxyphenyl]ethanone hydrazone as a yellow solid. The compound was recrystallized from isopropanol and then from toluene to afford 1.7 g (39%), m.p.=106°–108° C.

ANALYSIS

Calculated for $C_{24}H_{29}FN_4O_3$: 65.44% C 6.64% H 12.72% N.

Found: 65.38% C 6.55% H12.55% N.

EXAMPLE 80

6-Fluoro]-3-[1-[3-[2-methoxy-4-(1-methylethenyl) phenoxy]propyl]-4-piperidinyl]-1,2-benzisoxazole hydrochloride A solution of butyllithium (4.7 ml of a 2.3 M solution in hexanes, 0.0107 mol) in tetrahydrofuran (65 ml) was stirred under nitrogen and cooled to −70° to an isopropyl alcohol-dry ice bath. Methyltriphenylphosphonium bromide (3.8 g, 0.0106 mol) wa added portionwise over the course of 10 minutes. After complete addition, the reaction was stirred at −65° C. for one hour and was then allowed to gradually warm up to ambient temperature, where it was stirred for an additional 3.5 hours. The reaction was cooled to 0° C., and a solution of 1-[4-[3-[4-(6-fluoro-1,2-benzisoxazol-3-yl)-1-piperidinyl]propoxy]-3-methoxyphenyl]ethanone prepared as in Example 3 above (4.7 g, 0.0110 mol) dissolved in tetrahydrofuran (50 ml) was added, dropwise, over the course of 30 mixtures. After the addition was complete, the reaction was stirred at ambient temperature for 19 hours. The reaction was poured into water and the aqueous mixture was extracted with diethyl ether. The diethyl ether extract was washed several times with water, dried with $MgSO_4$ and concentrated to yield 7.0 g of a light orange solid. Recrystallization from toluene-hexane provided 1.4 g of triphenylphosphine oxide and concentration of the filtrate afforded 5.5 g of a glassy, beige solid. This was combined with an additional sample (6.5 g total) and purification by preparative HPLC (Water's Associates prep LC/System 500) gave 5.2 g of a beige solid, which remained contaminated by triphenylphosphine oxide. The compound was taken up in anhydrous ethanol (300 ml) and methanol (5 drops) and ethereal HCl was added to precipitate 4.0 g of a pale, white solid, m.p.=192°–194° C.

ANALYSIS

Calculated for $C_{25}H_{30}ClFN_2O_3$: 65.14% C 6.56% H 6.08% N.

Found: 64.95% C 6.62% H 6.04% N.

EXAMPLE 81

(E)-1-[4-[[4-[4-(6-Fluoro-1,2-benzisoxazol-3-yl)-1-piperidinyl]-2-butenyl]oxy]-3-methoxyphenyl] ethanone A mixture of 6-fluoro-3-(4-piperidinyl)-1,2-benzisoxazole (2.2 g, 10 mmoles), $K_2CO_3$ (2 g), (E)-4-[(4-bromo-2-butenyl)oxy-3-methoxyacetophenone (4.0 g, 1.3 eq) in acetonitrile (100 ml) was heated at reflux for 2 hours. At the end of the reaction, the solvent was removed on the rotary evaporator. The residue was extracted into dichloromethane (300 ml). The insolubles were filtered off. The dichloromethane was concentrated. The crude product was purified on a flash chromatography column. The product eluted as an oil, weight 2.87 g (64%). Recrystallization from ethanol:hexane (200 ml:5 ml) gave (E)-1-[4-[[4-[4-(6-fluoro-1,2-benzisoxazol-3-yl)-1-piperidinyl]-2-butenyl] oxy]-3-methoxyphenyl]ethanone as off-white crystals: 2.46 g; m.p.=91°–93° C.

ANALYSIS

Calculated for $C_{25}H_{27}FN_2O_4$: 68.48% C 6.21% H 6.39% N.

Found: 68.28% C 6.12% H 6.27% N.

EXAMPLE 82

(Z)-1-[4-[(4-Chloro-2-butenyl)oxy]-3-methoxyphenyl]ethanone

A stirred mixture of 4-hydroxy-3-methoxyacetophenone (16.6 g, 0.1 mole), $K_2CO_3$ (14 g, 0.10 mole) and cis-1,4-dichloro-2-butene (Aldrich, 15 g, 0.12 mole) in acetonitrile (250 ml) was heated at reflux for 2.5 hr. The mixture was filtered and concentrated to an oil. Purification was by flash chromatography. The fractions containing the purest product were combined and concentrated to give white crystals, 7.7 g, 30%. This was recrystallized from ether to give analytical pure (Z)-1-[4-[(4-chloro-2-butenyl)oxy]-3-methoxyphenyl] ethanone (2.72 g), m.p.=64°–66° C.

ANALYSIS

Calculated for $C_{13}H_{15}ClO_3$: 61.30% C 5.94% H.

Found: 61.28% C 5.94% H.

EXAMPLE 83

(Z)-1-[4-[[4-[4-(6-Fluoro-1,2-benzisoxazol-3-yl)-1-piperidinyl]-2-butenyl]oxy]-3-methoxyphenyl] ethanone A stirred mixture of 6-fluoro-3-(4-piperidinyl)-1,2-benzisoxazole (2.2 g, 10 mmoles), $K_2CO_3$(1.8 g, 13 mmoles) and (Z)-1-[4-[(4-chloro-2-butenyl)oxy]-3-methoxyphenyl]ethanone (3.43 g, 9.7 mmoles) in acetonitrile (100 ml) was heated at reflux for 1½ hr. At the end of the reaction, the solvent was removed and the inorganics were filtered after addition of dichloromethane (250 ml). The dichloromethane solvent was removed again. The crude oil was purified on two flash chromatography columns to give a colorless oil (2.78 g). The oil was solidified by vigorously drying on a vacuum pump. Recrystallization from ethanol (10 ml) and hexane (2 ml) gave analytically pure (Z)-1-[4-[[4-[4-(6-fluoro-1,2-benzisoxazol-3-yl)-1-piperidinyl]-2-butenyl]oxy]3-methoxyphenyl]ethanone, 1.83 g, m.p.=57°–59° C.

ANALYSIS

Calculated for $C_{25}H_{27}FN_2O_4$: 68.48% C 6.21% H 6.39% N.

Found: 68.26% C 6.18% H 6.32% N.

EXAMPLE 84

(E)-1-[3-[[4-[4-(6-Fluoro-1,2-benzisoxazol-3-yl)-1-piperidinyl]-2-butenyl]oxy]-4-hydroxyphenyl] ethanone hydrochloride The mixture of (E)-1-[3-[[4-[4-(6-fluoro-1,2-benzisoxazol-3-yl)-1-piperidinyl]-2-butenyl]oxy]-4benzyloxyphenyl]ethanone (5.5 g, 10.7 mmole), acetic acid (50 ml), and hydrochloric acid (6 ml) was heated at 75° C. for 2 hr. At the end of reaction, the solvent was reduced about 20 ml on a rotary evaporator. The solution was poured into ice water (350 ml) and extracted with dichloromethane (3>250 ml). The dichloromethane solution was washed with brine and dried over $Na_2SO_4$. A solid formed on concentration of the solvent. This was collected by filtration (3.4 g). Recrystallization from hot methanol (40 ml) gave 1.82 g of (E)-1-[3-[[4-[4-(6-fluoro-1,2-benzisoxazol-3-yl)-1-piperidinyl]-2-butenyl]oxy]-4-hydroxyphenyl]ethanone hydrochloride as white crystals, 37.5%, m.p.=208°–210° C.

ANALYSIS

Calculated for $C_{24}H_{25}FN_2O_4$.HCl: 62.54% C 5.69% H 6.08% N.

Found: 62.40% C 5.60% H 6.04% N.

EXAMPLE 85

(E)-1-[3-[[4-[4-(6-Fluoro-1,2-benzisoxazol-3-yl)-1-piperidinyl]-2-butenyl]oxy]-4-benzyloxyphenyl] ethanone (A) (E)-3-[(4'-bromo-2'-butenyl)oxy]-4-benzyloxyacetophenone To 4-benzyloxy-3-hydroxyacetophenone (17.6 g) in acetonitrile (200 ml) was added potassium carbonate (10 g), followed by the addition of (E)-1,4-dibromobutene (19 g). The resulting mixture was heated at reflux for 3 hours. The mixture was concentrated, extracted into dichloromethane, and the potassium salt was removed by filtration. Solvent was removed, and the resulting material was purified by flash chromatography to yield 20.5 g of (E)-3-[(4'-bromo-2'-butenyl)oxy]-4-benzyloxyacetophenone as white crystals.

(E)-1-[3-[[4-[4-(6-fluoro-1,2-benzisoxazol-3-yl)-1-piperidinyl]-2-butenyl]oxy]-4-benzyloxyphenyl] ethanone A mixture of 6-fluoro-3-(4-piperidinyl)-1,2-benzisoxazole (5.62 g, 25.5 mmoles), $K_2CO_3$ (4 g, 29 mmoles), and (E)-3-[(4-bromo-2'-butenyl)oxy]-4-benzyloxyacetophenone (10 g, 26.6 mmole) in acetonitrile (125 ml) was heated at reflux for 3.5 hr. The mixture was cooled and concentrated to a crude solid. The residue was extracted into dichloromethane (300 ml) and insolubles were filtered. The crude material form the dichloromethane solu tion was purified on a flash chromatography column. The product thus purified weighed 8 g as a pale white solid. Recrystallization from hot ethanol gave 7.11 g of (E)-1-[3-[[4-[4-(6-fluoro-1,2-benzisoxazol-3-yl)-1-piperidinyl]-2-butenyl]oxy]-4benzyloxyphenyl]ethanone as off-white crystals, m.p.=124°–125° C.

ANALYSIS

Calculated for $C_{31}H_{31}FN_2O_4$: 72.36% C 6.07% H 5.44% N.

Found: 72.23% C 6.04% H 5.04% N.

EXAMPLE 86

6-Fluoro-3-[1-[3-[(5-methoxy-1H-indol-6-yl)oxy]propyl]-4-piperidinyl]-1,2-benzisoxazole (A) 6-(3-Chloropropoxy]-5-methoxyindole To a stirred suspension of sodium hydride (0.94 g, 19.6 mmol of a 50% oil dispersion) in dimethylformamide (20 ml) under nitrogen and cooled to −5° was added, dropwise, 5-methoxy-6-hydroxyindole (3.2 g, 19.6 mmol) dissolved in dimethylformamide (60 ml) so that the temperature did not exceed −2°. After complete addition, the reaction was stirred for 45 minutes at 0°. While maintaining the reaction temperature between −5° and 0°, a solution of 1-bromo-3-chloropropane (3.1 g, 19.6 mmol) dissolved in dimethylformamide (15 ml) was slowly added. The mixture was stirred at ambient temperature under nitrogen for 21 hours. The reaction was cooled in an ice bath, and water was added to destroy the excess sodium hydride, and the aqueous mixture was extracted with ethyl acetate. The ethyl acetate extract was washed with water, dried with $MgSO_4$ and concentrated to yield 5.3 g of a dark, oily liquid. This was combined with an additional sample, for a total of 10.0 g, and purification by preparative HPLC (Waters Associates prep LC/System 500) provided 5.1 g of a brown solid. A 2.5 g sample was recrystallized from isopropyl alcohol to yield 1.1 g (30%) of 6-(3-chloropropoxy)-5-methoxyindole as beige crystals, m.p.=73°–75° C.

ANALYSIS

Calculated for $C_{12}H_{14}ClNO_2$: 60.13% C 5.89% H 5.84% N.

Found: 60.26% C 5.86% H 5.77% N.

B.

6-Fluoro-3-[1-[3-[(5-methoxy-1H-indol-6-yl]oxy]propyl]-4-piperidinyl]-1,2-benzisoxazole A mixture of 6-fluoro-3-(4-piperidinyl)-1,2-benzisoxazole (2.5 g, 11.5 mmol), 6-(3-chloropropxy)-5-methoxyindole (2.5 g, 10.4 mmol), $K_2CO_3$ (1.6 g, 11.5 mmol), KI (200 mg) and acetonitrile (100 ml) was stirred at reflux under nitrogen for 40 hours. The cooled reaction was poured into water and extracted with ethyl acetate. The ethyl acetate extract was washed with water, washed with brine, dried with $MgSO_4$ and concentrated to yield 4.0 g of a solid. The compound was recrystallized from ethanol to afford 3.3 g. Another recrystallization from ethanol (utilizing a charcoal treatment) provided 2.9 g (66%) of 6-fluoro-3-[1-[3-[(5-methoxy-1H-indol-6-yl)oxy]propyl]-4-piperidinyl]-1,2-benzisoxazole as a beige solid, m.p.=156°–158° C.

ANALYSIS

Calculated for $C_{24}H_{26}FN_3O_3$: 68.07% C 6.19% H 9.92% N.

Found: 67.89% C 6.07% H 9.91% N.

EXAMPLE 87

6-Fluoro-3-[1-[3-[(1H-indol-7-yl)oxy]phenyl]-4-piperidinyl]-1,2-benzisoxazole hemifumarate (A) 7-(3-Chloropropoxy)indole To a stirred suspension of sodium hydride (0.8 g, 0.017 mmol of a 50% oil dispersion) in dimethylformamide (20 ml), under nitrogen, was added dropwise 7-hydroxyindole (2.1 g, 0.0157 mol) in dimethylformamide (20 ml). After complete addition, the reaction was stirred at ambient temperature for 0.5 hour and then cooled to 15° C. To this cooled solution was added, dropwise, 1-bromo-3-chloropropane (2.5 g, 0.0157 mol) in dimethylformamide (5 ml). The reaction was then stirred at ambient temperature for 16 hours. The reaction was poured into water, and the aqueous suspension extracted with ethyl acetate. The ethyl acetate was washed with water, dried ($MgSO_4$), and the solvent was concentrated to afford a dark brown oil. Following flash chromatography on silica gel, 7-(3-chloropropoxy)indole was obtained as a colorless oil, 1.0 g.

ANALYSIS

Calculated for $C_{11}H_{12}ClNO$: 63.01% C 5.77% H 6.68% N.

Found: 63.25% C 5.61% H 6.65% N.

(B) 6-Fluoro-3-[1-[3-[(1H-indol-7-yl)oxy]propyl]-4-piperidinyl]-1,2-benzisoxaole hemifumarate A stirred mixture of 7-(3-chloropropoxy)-1H-indole (3.5 g, 0.017 mol), 6-fluoro-3-(4-piperidinyl)-1,2-benzisoxazole (3.5 g, 0.017 mol), $K_2CO_3$ (2.3 g) and acetonitrile (60 ml) was refluxed for 11 hours. The reaction was poured into water, and the aqueous mixture was extracted with ethyl acetate. The ethyl acetate was washed with water, dried ($MgSO_4$), and the solvent was concentrated to afford a dark oil. The oil was flash chromatographed on silica gel. Upon concentration of the appropriate fractions, 3.0 g of white, foamy substance was obtained. The substance was dissolved in ethyl acetate (75 ml) and fumaric acid (0.97 g, 0.083 mol) was added. The mixture was briefly heated to reflux, and then stirred at ambient temperature for 1.5 hours. The resultant insoluble white fumaric salt was collected and afforded 4.2 g of product. Recrystallization of the salt from dimethylformamide yielded 3.1 g (36%) of 6-fluoro-3-[3-[(1H-indol-7-yl)oxy]propyl]-4-piperidinyl]-1,2-benzisoxazole hemifumarate as a white solid, m.p.=213°–215° C.

ANALYSIS

Calculated for $C_{25}H_{26}FN_3O_4$: 66.50% C 5.80% H 9.31% N.

Found: 66.23% C 6.14% H 9.39% H.

EXAMPLE 88

6-Fluoro-3-[1-(3-hydroxypropyl)-4-piperidinyl]-1,2-benzisoxazole

A stirred mixture of 6-fluoro-3-(4-piperidinyl)-1,2-benzisoxazole (10.0 g, 0.045 mol), $K_2CO_3$ (10.0 g), 3-bromo-1-propanol (7.3 g, 0,046 mol) and acetonitrile (200 ml) was refluxed for 3 hours. The reaction was poured into $H_2O$ and 7.1 g of a beige solid was collected. The filtrate was extracted with dichloromethane, and after concentration an additional 6.7 g of crude solid was harvested. The solids were combined and triturated with refluxing ethyl acetate to afford 8.0 g of 6-fluoro-3-[1-(3-hydroxypropyl)-4-piperidinyl]-1,2-benzisoxazole as an off-white solid. A sample (4.0 g) was recrystallized from ethanol-water (with charcoal treatment) to yield 2.4 g (40%) of the alcohol as a white solid, m.p.=140°–142° C.

ANALYSIS

Calculated for $C_{15}H_{19}FN_2O_2$: 64.73% C 6.88% H 10.06% N.

Found: 64.79% C 6.97% H 10.03% N.

EXAMPLE 89

6-Fluoro-3-[1-(2-pyrimidinoxy)propyl]-4-piperidinyl]-1,2-benzisoxazole fumarate

To a stirred suspension of 6-fluoro-3-[1-(3-hydroxypropyl)-4-piperidinyl]-1,2-benzisoxazole (3.6 g, 0.013 mol) in tetrahydrofuran (50 ml) was added dropwise, potassium bistrimethylsilylamide (2.6 g, 0.013 mol) dissolved in tetrahydrofuran (20 ml). After complete addition, the reaction was stirred at ambient temperature for 5 min, and then 2-chloropyrimidine (1.6 g, 0.014 mol) was added. The reaction was stirred at ambient temperature for 4 hours, and TLC at this time indicated an incomplete reaction. An additional quantity of the base (0.5 g) was added, and the reaction was allowed to proceed at ambient temperature for 14 additional hours. The reaction was poured into water and the aqueous mixture was extracted with dichloromethane. The extract was washed ($H_2O$), dried ($K_2CO_3$), and the solvent was concentrated to afford a wet solid. The solid was triturated with diethyl ether and the product that separated was collected to yield 1.0 g of the starting alcohol. The filtrate was then concentrated to afford 3.8 g of a waxy, yellow solid. This material was combined with 2.6 g from another run and the combined sample flash chromatographed on silica gel, eluting first with ethyl acetate and then with 8% diethylamine-ethyl acetate. Concentration of the appropriate fractions afforded 3.0 g of the desired compound as a yellow solid. The solid was converted to a fumarate salt with fumaric acid in acetone, and then reversed to its free base. It was combined with another sample and the combined sample (3.8 g) chromatographed on silica gel on HPLC (4.5% methanoldichloromethane as eluent). Concentration of the appropriate fractions yielded 1.6 g of a yellow solid. A fumarate salt was prepared to yield 2.1 g (16%) of 6-fluoro-3-[1-[(2-pyrimidinoxy)propyl]-4-piperidinyl]-1,2-benzisoxazole fumarate, m.p.=184°–186° C.

ANALYSIS

Calculated for $C_{23}H_{25}FN_4O_6$: 58.47% C 5.33% H 11.86% N.

Found: 58.52% C 5.34% H 11.80% N.

EXAMPLE 90

6-Aceto-2-[4-(6-fluoro-1,2-benzisoxazol-3-yl)-1-piperidinyl]methyl-1,4-benzodioxan (A) 6-aceto-2-mesyloxymethyl-1,4-benzodioxan 6-Aceto-2-hydroxyethyl-1,4-benzodioxan (3.39 g, 16.3 mmol) was dissolved in trichloromethane (100 ml). Triethylamine (2.5 g) was added to methylchloride (2.5 g, 1.35 eq) at 0° C. The mixture was stirred for 2 hours at room temperature. The mixture was then diluted, washed with an ice/dilute hydrochloric acid mixture (150 ml), washed with sodium bicarbonate and brine, dried over magnesium sulfate, and concentrated to yield 5.6. Following chromatography on a $SiO_2$ column, 3.64 g (78% yield) of 6-aceto-2-methoxymethyl-1,4-benzodioxan were obtained.

(B) 6-aceto-2-[4-(6-fluoro-1,2-benzisoxazol-3-yl)-1-piperidinyl]methyl-1,4-benzodioxan A stirred mixture of 6-fluoro-3-(4-piperidinyl)-1,2-benzisoxazole (3.0 g, 13.6 mmoles), $K_2CO_3$ (2 g, 14.5 mmoles) and 6-aceto-2-mesyloxymethyl-1,4-benzodioxan (3.5 g, 12 mmoles) in acetonitrile (100 ml) was heated at reflux for 3 hr. At the end of the reaction the solvent was removed on a rotary evaporator. The residue was extracted into dichloromethane (350 ml) and the insolubles were filtered off. The dichloromethane solution was concentrated and the crude oil was purified by flash chromatography. The product thus obtained weighed 3.38 g (59%). Recrystallization from ethanol gave 6-aceto-2-[4-(6-fluoro-1,2-benzisoxazol-3-yl)-1-piperidinyl]methyl-1,4-benzodioxan as light yellow crystals (3.2 g), m.p.=122°–123° C.

ANALYSIS

Calculated for $C_{23}H_{23}FN_2O_4$: 67.31% C 5.65% H 6.83% N.

Found: 67.24% C 5.50% H 6.75% N.

EXAMPLE 91

2-[4-(6-Fluoro-1,2-benzisoxazol-3-yl)-1-piperidinyl]methyl-1,4-benzodioxan

A stirred mixture of 6-fluoro-3-(4-piperidinyl)-1,2-benzisoxazole (3.0 g, 13.6 mmoles), $K_2CO_3$ (2.45 g, 17.7 mmoles), 2-methanesulfonyloxymethyl-1,4-benzodioxan (3.35 g, 13.7 mmole) in acetonitrile (100 ml) was heated at reflux for 12 hours. At the end of the reaction, the insolubles were filtered and rinsed with dichloromethane. The organic solution was concentrated. The crude oil was purified by flash chromatography on a silica gel column. The fractions containing the pure product were pooled and concentrated to a light yellow oil (3.94: g, 74%). Crystallization from ethanol and petroleum ether gave 2-[4-(6-fluoro-1,2-benzisoxazol-3-yl)-1-piperidinyl]methyl-1,4-benzodioxan as off-white crystals, 2.22 g, m.p.=86°–87° C.

ANALYSIS

Calculated for $C_{21}H_{21}FN_2O_3$: 68.47% C 5.75% H 7.60% N.

Found: 68.33% C 5.75% H 7.51% N.

EXAMPLE 92

2-[4-(6-Fluoro-1,2-benzisoxazol-3-yl)-1-piperidinyl]ethyl]-1,4-benzodioxan (A) 2-mesyloxyethyl-1,4-benzodioxan To the compound 2-hydroxymethyl-1,4-benzodioxan (11.96 g) in dichloromethane (450 ml) was added triethylamine (0.12 mol, 10 ml). Mesylchloride (9.2 g) was then added dropwise and the reaction mixture was stirred for one hour at room temperature. After completion of the reaction, the solution was washed with water, brine, and concentrated to an oil, which was purified by chromatography on silica gel to yield 2-mesyloxyethyl-1,4-benzodioxan, 17.08 g.

(B) 2-[4-(6-fluoro-1,2-benzisoxazol-3-yl)-1-piperidinyl]ethyl]-1,4-benzodioxan

A mixture of 6-fluoro-3-(4-piperidinyl)-1,2-benzisoxazole (4.7 g, 21 moles), $K_2CO_3$ (3.5 g, 25.4 moles) and 2-mesyloxyethyl-1,4-benzodioxan (5.5 g, 21.3 mmoles) in acetonitrile (250 ml) was heated at reflux for 3.5 hours. At the end of the reaction, insolubles were filtered. The solid was washed with dichloromethane (200 ml). The solutions were combined and evaporated to an oil. This crude oil was purified by flash chromatography on a silica gel column. The material thus obtained was crystallized from ethanol. The 2-[4-(6-fluoro-1,2-benzisoxazol-3-yl)-1-piperidinyl]ethyl]-1,4-benzodioxan crystals were collected and weighed 3.8 g, 48%, m.p.=112°–113° C.

ANALYSIS

Calculated for $C_{22}H_{23}FN_2O_3$: 69.09% C 6.06% H 7.32% N.

Found: 69.17% C 6.02% H 7.31% N.

EXAMPLE 93

6-[3-[4-(6-Fluoro-1,2-benzisoxazol-3-yl)-1-piperidinyl]propoxy]-7-methoxy-1-tetralone (A) 6-(3-chloropropoxy)-1-tetralone A mixture of 6-hydroxy-7-methoxy-1-tetralone (J. Org. Chem., 1985, 50, 4937) (1.5 g, 7.8 mmol), $K_2CO_3$ (1.7 g, 12.3 mmol), and acetone (30 ml) was stirred at reflux under nitrogen for 45 minutes. The reaction was cooled to ambient temperature and a solution of 1-bromo-3-chloropropane (1.9 g, 12.1 mmol) dissolved in 8 ml acetone was dripped into the mixture. After total addition, the reaction was heated to reflux and stirred under nitrogen for 21 hours. The reaction was cooled to ambient temperature and filtered. The filter cake was washed well with acetone and the filtrate was concentrated to yield 2.0 g 6-(3-chloropropoxy)-7-methoxy-1-tetralone as an amber oil.

(B) 6-[3-[4-(6-fluoro-1,2-benzisoxazol-3-yl)-1-piperidinyl]propoxy]-7-methoxy-1-tetralone A mixture of 6-fluoro-3-(4-piperidinyl)-1,2-benzisoxazole (0.78 g, 3.6 mmol), $K_2CO_3$ (0.60 g, 4.1 mmol), KI (100 mg), 6-(3-chloropropoxy)-7-methoxy-1-tetralone (0.87 g, 3.2 mmol), and acetonitrile (50 ml) was stirred at reflux under nitrogen for 17 hours. The cooled reaction was poured into 100 ml of water and the aqueous mixture was extracted with ethyl acetate. The ethyl acetate extract was washed with brine, dried with $MgSO_4$ and concentrated to yield 1.7 g of a brown oil. The oil was purified by preparative HPLC (Waters Associates Prep LC/system 500) to afford 1.0 of a light brown solid. This was combined with an additional sample (2.3 g total) and recrystallization from ethanol yielded 1.7 g. A subsequent recrystallization from ethanol gave 1.25 g (36%) of 6-[3-[4-(6-fluoro-1,2-benzisoxazol-3-yl)-1-piperidinyl]propoxy]-7-methoxy-1-tetralone as a beige powder, m.p.=129°–131° C.

ANALYSIS

Calculated for $C_{26}H_{29}FN_2O_4$: 69.01% C 6.46% H 6.19% N.

Found: 68.77% C 6.43% H 6.16% N.

EXAMPLE 94

N-[3-[4-(6-Fluoro-1,2-benzisoxazol-3-yl)-1-piperidinyl]propyl]-6-acetyl-2-benzoxazolinone (A) N-(3-chloropropyl)-2-benzoxazolinone To a stirred suspension of sodium hydride (7.8 g, 0.16 mol, ether-washed) in dimethylformamide (75 ml) was added dropwise under nitrogen, 2-benzoxazolinone (20.0 g, 0.15 mol) dissolved in dimethylformamide (150 ml). After complete addition the reaction was stirred at ambient temperature for 30 min, and then it was cooled to −5° C. with an ice-acetone bath. A solution of 3-chloro-1-bromopropane (46.6 g, 0.30 mol) in dimethylformamide (50 ml) was added dropwise (temperature never exceeded 0° C.). The reaction was allowed to reach ambient temperature and was stirred for 16 hours. The reaction was poured into water, and the aqueous mixture was extracted with ethyl acetate. The ethyl acetate was washed with water, dried ($MgSO_4$), and the extract concentrated to afford 21.9 of a brown solid. The solid was recrystallized from toluene-hexane to afford N-(3-chloropropyl)-2-benzoxazolinone as large needles, 15.6 g, m.p.=264°–266° C.

(B) N-(3-chloropropyl)-6-acetyl-2-benzoxazolinone

A mixture of N-(3-chloropropyl)-2-benzoxazolinone (8.5 g, 0.04 mol), polyphosphoric acid (100 g), and acetic acid (2.4 g, 2.3 ml, 0.04 mol), was stirred and heated at 100° C. for 2 hours. The hot solution was poured into ice-water to deposit a yellow gum. The mixture was extracted with dichloromethane, and insolubles were filtered. The dichloromethane extract was washed with water, dried ($K_2CO_3$), and concentrated to afford 6.4 g of a slightly green solid. This was recrystallized from ethanol (95%) to yield N-(3-chloropropyl)-6-acetyl-2-benzoxazolinone as a brown solid, 3.5 g, m.p.=100°–103° C.

(C) N-[3-[4-(6-fluoro-1,2-benzisoxazol-3-yl)-1-piperidinyl]propyl]-6-acetyl-2-benzoxazolinone A mixture of 6-fluoro-3-(4-piperidinyl)-1,2-benzisoxazole (2.0 g, 0.009 mol), N-(3-chloropropyl)-6-acetyl-2-benzoxazolinone (2.4 g, 0.009 mol), $K_2CO_3$ (3.6 g), a few crystals of KI, and acetonitrile (50 ml) was stirred and refluxed for 13 hours. The reaction was poured into water, and a dark, brown solid that separated was collected to afford 3.3 g of crude product. The solid was chromatographed on a Waters Prep 500 HPLC. Concentration of appropriate fractions afforded 2.3 g of a yellow solid, and recrystallization from ethyl acetate yielded 1.2 g (31%) of N-[3-[4-(6-fluoro-1,2-benzisoxazol-3-yl)-1-piperidinyl]propyl]-6-acetyl-2-benzoxazolinone, m.p.=152°–154° C.

ANALYSIS

Calculated for $C_{24}H_{24}FN_3O_4$: 65.89% C 5.53% H 9.61% N.

Found: 65.67% C 5.48% H 9.52% N.

EXAMPLE 95

N-[3-[4-(6-fluoro-1,2-benzisoxazol-3-yl)-1-piperidinyl]propyl]phthalimide

A mixture of 6-fluoro-3-(4-piperidinyl)-1,2-benzisoxazole (6.44 g, 29.1 mmole), $K_2CO_3$ (6.4 g, 46 mmoles), N-(3-bromopropyl)phthalimide (8.4 g, 31 mmoles) in acetonitrile (150 ml) was heated at reflux for 3.5 hr. The insolubles were filtered. The solvent was removed at reduced pressure and the residue was purified by silica gel column chromatography to give N-[3-[4-(6-fluoro-1,2-benzisoxazol-3-yl)-1-piperidinyl]propyl]phthalimide as a white solid. Recrystallization from ethanol yielded 9.8 g (83%) of off-white crystals, m.p.=129°–1300C.

ANALYSIS

Calculated for $C_{23}H_{22}FN_3O_3$: 67.89% C 5.44% H 10.31% N.

Found: 67.49% C 5.38% H 10.13% N.

EXAMPLE 96

1-(3-Aminopropyl)-4-(6-fluoro-1,2-benzisoxazol-3-yl)-piperidine dihydrochloride

A mixture of N-[3-[4-(6-fluoro-1,2-benzisoxazol-3-yl)-1-piperidinyl]propyl]phthalimide (8.5 g, 21 moles), hydrazine monohydrate (1.5 g, 30 mmoles) in methanol (60 ml) was heated at reflux for 2 hours. At the end of the reaction, methanol was removed to leave a crude solid. To this was added water (60 ml), then the mixture was acidified with HCl to pH 1. The insolubles were filtered with the aid of a pad of celite. The aqueous solution was basified with 50% NaOH, (pH 13), then extracted with dichloromethane. The combined dichloromethane solution was washed with brine, then dried to a colorless oil (4.5 g). The analytical sample (1.5 g) was prepared by treating the oil with HCl in ethanol at 0° C. The 1-(3-aminopropyl)-4-(6-fluoro-1,2-benzisoxazol-3-yl)piperidine dihydrochloride was obtained as white crystals, 2.03 g, m.p.=231°–234° C.

ANALYSIS

Calculated for $C_{15}H_{20}FN_3O.2HCl$: 51.44% C 6.33% H 12.00% N.

Found: 51.35% C 6.49% H 11.90% N.

EXAMPLE 97 cis-2-[3-[4-(6-Fluoro-1,2-benzisoxazol-3-yl)-1-piperidinyl]propyl]-hexahydro-1H-isoindole-1,3-dione hydrochloride A mixture of 1-(3-aminopropyl)-4-(6-fluoro-1,2-benzisoxazol-3-yl)piperidine (3.01 g, 10.8 moles) and cis-1,2-cyclohexane-dicarboxylic anhydride (1.9 g, 12.3 mmoles) in dry pyridine (30 ml) was heated at reflux for 16 hours. The dark brown solution was concentrated to dryness on a rotary evaporator. The crude residue was purified twice by flash chromatography over a silica gel column. The pure product thus obtained weighed 2.5 g (67%). This was converted to the hydrochloride salt by treatment with HCl in ethanol (50 ml). The cis-2-[3-[4-(6-fluoro-1,2-benzisoxazol-3-yl)-1-piperidinyl]propyl]hexahydro-1H-isoindole-1,3-dione hydrochloride crystals so obtained weighed 3.0 g. m.p.=242°–245° C.

ANALYSIS

Calculated for $C_{23}H_{28}FN_3O_3.HCl$: 61.14% C 6.50% H 9.34% N.

Found: 61.32% C 6.32% H 9.27% N.

EXAMPLE 98

N-[4-[4-(6-Fluoro-1,2-benzisoxazol-3-yl)-1-piperidinyl]butyl]phthalimide

A mixture of 6-fluoro-3-(4-piperidinyl)-1,2-benzisoxazole (5.5 g, 25 mole), 4-bromobutylphthalimide (8.0 g, 28.3 moles, 1.13 eq), $K_2CO_3$ (4.55 g, 32 mmoles) in acetonitrile (100 ml) was heated at reflux for 3 hr. At the end of the reaction, the mixture was filtered. The insolubles were washed with dichloromethane (200 ml). The organic solution was concentrated gradually to allow crystallization. The crude crystals (5.9 g) were collected. The mother liquor was concentrated to a solid (5.5 g). Purification was by flash chromatography over a silica gel column. The product (3.8 g) thus purified was recrystallized from ethanol (70 ml) to give 2.48 g of N-[4-[4-(6-fluoro-1,2-benzisoxazol-3-yl)-1-piperidinyl]butyl]phthalimide as white crystals, m.p.=144°–146° C.

ANALYSIS

Calculated for $C_{24}H_{24}FN_3O_3$: 68.39% C 5.74% H 9.97% N.

Found: 68.34% C 5.74% H 9.84% N.

EXAMPLE 99

1-(4-Aminobutyl)-4-(6-fluoro-1,2-benzisoxazol-3-yl)piperidine dihydrochloride

A mixture of N-[4-[4-(6-fluoro-1,2-benzisoxazol-3-yl) piperidinyl]butyl]phthalimide (6.9 g, 16.4 mmoles) and hydrazine monohydrate <1.64 g, 32.8 mmoles) in methanol (70 ml) was heated at reflux for 3 hours. At the end of the reaction, methanol was removed to leave a crude solid. This was dissolved in water and acidified with HCl to pH 2. The insolubles were filtered. The aqueous solution was basified with 50% NaOH, and then extracted with dichloromethane. The dichloromethane solution was washed with water and brine, and then dried over $MgSO_4$. The solvent was removed to a colorless oil: 4.48. This oil was treated with 2.5 equivalents of HCl in ethanol. The solid was collected. Recrystallization from ethanol (65 ml) and methanol (20 ml) gave 2.0 of 1-(4-aminobutyl)-4-(6-fluoro-1,2-benzisoxazol-3-yl)piperidine dihydrochloride as white crystals, m.p.=234°–237° C.

ANALYSIS

Calculated for $C_{16}H_{22}FN_3O.2HCl$: 52.75% C 6.64% H 11.53% N.

Found: 52.37% C 6.59% H 11.07% N.

EXAMPLE 100 cis-2-[4-[4-(6-Fluoro-1,2-benzisoxazol-3-yl)-1-piperidinyl]butyl]-hexahydro-1H-isoindole-1,3-dione hydrochloride A mixture of 1-(4-aminobutyl)-4-(6-fluoro-1,2-benzisoxazol-3-yl)piperidine (4.7 g, 16.1 mmoles) and cis-1,2-cyclohexanedicarboxylic anhydride (3.23 g, 21 mmoles) in pyridine (45 ml) was heated at reflux for 8 hours. At the end of the reaction, pyridine was removed to dryness. The crude product was purified on a silica gel column. The material thus obtained weighed 3.18 g (45%) as a clear oil. This oil was dissolved in ethanol (15 ml), then was treated with HCl in ethanol (45 ml). Crystallization took place upon cooling. The crystals were collected, 3.2 g, m.p.=229°–231° C.

ANALYSIS

Calculated for $C_{24}H_{30}FN_3O_3.HCl$: 62.13% C 6.73% H 9.06% N.

Found: 61.79% C 6.68% H 8.92% N.

EXAMPLE 101

1-[4-[3-[4-(6-Fluoro-1,2-benzisoxazol-3-yl)-1-piperidinyl]propyl]thio]-3-methoxyphenyl]ethanone (A) 1-[4-[(3-chloropropyl)thio]-3-methoxyphenyl] ethanone A mixture of 1-(4-thio-3-methoxyphenyl)ethanone (10.0 g, 0.0549 mol), potassium carbonate (9.0 g, 0.0651 mol), and acetone (100 ml) was stirred at reflux under nitrogen for 30 minutes. The reaction was cooled to ambient temperature and a solution of 1-bromo-3-chloropropane (6.5 ml, 9.5 g, 0.0604 mol) dissolved in acetone (25 ml) was dripped into the reaction. After complete addition, the reaction was heated to reflux and stirred under nitrogen for 17 hours. After the reaction was carried to substantial completion, the reaction mixture was filtered and the resulting filter cake was washed with acetone. The filtrate was concentrated to provide an amber oil. A small sample was solidified by trituration with hot cyclohexane to provide 1-[4-[(3-chloropropyl)thio]-3-methoxyphenyl]ethanone as a yellow solid, 11.7 g, m.p. 53°–55° C.

(B) 1-[4-[[3-[4-(6-fluoro-1,2-benzisoxazol-3-yl)-1-piperidinyl]propyl]thio]-3-methoxyphenyl]ethanone A mixture of 6-fluoro-3-(4-piperidinyl)-1,2-benzisoxazol (3.0 g, 0.0136 mol), 1-[4-[(3-chloropropyl)thio]-3-methoxyphenyl]ethanone (3.5 g, 0.0136 mol), $K_2CO_3$ (2.3 g, 0.0166 mol), KI (200 mg) and $CH_3CN$ (100 ml) was stirred at reflux under nitrogen for 7.5 hours and then was left at ambient temperature for 65 hours. The reaction was poured into water and the aqueous mixture was extracted with ethyl acetate. The ethyl acetate extract was washed twice with water, once with brine and dried over $MgSO_4$. The solvent was removed in vacuo to afford 6.8 g of a light brown oil. The sample was purified by flash chromatography. Concentration of appropriate fractions yielded 3.0 g. Recrystallization from ethanol provided 2.4 g (41%) of 1-[4-[3-[4-(6-fluoro-1,2-benzisoxazol-3-yl)-1-piperidinyl] propyl]thio]-3-methoxyphenyl]ethanone as a beige solid, m.p.=93°–95° C.

ANALYSIS

Calculated for $C_{24}H_{27}FN_2O_3S$: 65.14% C 6.15% H 6.33% N.

Found: 64.66% C 6.17% H 6.26% N.

EXAMPLE 102

4-(6-Fluoro-1,2-benzisoxazol-3-yl)-1-[4-(2'-methoxyphenyl)]butylpiperidine maleate (A) 2-(4-bromobutyl]anisole 2-Bromoanisole (2.0 g, 1.07 mmol) in tetrahydrofuran (20 ml) was cooled to −78° C. under nitrogen and secondary butyllithium (1.3M, 10 ml, 1.3 eq) was charged into the resulting solution for two hours. The solution was quenched with 1,4-dibromobutane (3.2 g) and allowed to stir at ambient temperature overnight. The mixture was diluted with ethyl acetate, washed with water and brine, and concentrated to an oil. Following chromatography on a $SiO_2$ column, 2.4 g of 2-(4-bromobutyl)anisole were obtained.

(B) 4-(6-fluoro-1,2-benzisoxazol-3-yl)-1-(2-methoxyphenyl]butylpiperidine maleate A mixture of 6-fluoro-3-(4-piperidinyl)-1,2-benzisoxazole (2.36 g, 10.7 mole), $K_2CO_3$ (2 g, 14.5 mmoles) and 2-(4-bromobutyl)anisole (2.4 g, 10 moles) in acetonitrile (100 ml) was heated at reflux for 2.5 hr. At the end of reaction, the solvent was removed. The residue was extracted into dichloromethane (200 ml) and filtered. The dichloromethane solution was concentrated. The crude oil obtained was purified on a flash chromatography column. The material thus purified was a light yellow oil (2.73 g, 53%). This oil was dissolved in ethanol and treated with maleic acid (607 mg, 1.0 eq) in ethanol. The 4-(6-fluoro-1,2-benzisoxazol-3-yl)-1-(2'-methoxyphenyl)butylpiperidine maleate crystals formed on concentration and subsequent cooling to 0° C. These were collected and dried to yield 2.05 g, m.p.=132°–133° C.

ANALYSIS

Calculated for $C_{23}H_{27}FN_2O_2.C_4H_4O_4$: 65.05% C 6.27% H 5.62% N.

Found: 65.25% C 6.30% H 5.70% N.

EXAMPLE 103

1-[4-[4-[1-(1,3-Dithian-2-yl)ethyl]phenyl]butyl]-4-(6-fluoro-1,2-benzisoxazol-3-yl)piperidine (A) 4-bromo-1-[1,3-dithian-2-yl)ethylbenzene To the compound p-bromoacetophenone (36.85 g, 0.185 mol) in trichloromethane (300 ml) was added 1,3-propanedithiol (25 g, 0.23 mol) and boron trifluoride etherate (3 ml). The resulting mixture was stirred at room temperature for 48 hours. The mixture was diluted with dichloromethane (500 ml), washed twice with 10% sodium hydroxide (200 ml), water, and brine, and then dried ($Na_2SO_4$). The product was concentrated to an oil. A portion was stirred with ether (100 ml) and a crystalline product was formed. The crystalline product was recovered by filtration and purified by recrystallization to yield 4-bromo-1-(1,3-dithian-2-yl)ethylbenzene.

(B) 4-(4-bromobutyl]-1-[1,3-dithian-2-yl) ethylbenzene

A solution of 4-bromo-1-(1,3-dithian-2-yl)ethylbenzene (27.2 g, 94 moles) in tetrahydrofuran (200 ml) was charged with sec-butyllithium (99 ml, 1.3M in cyclohexane, 0.13 mole) dropwise at −78° C. under nitrogen. The mixture was stirred at ambient temperature for 1.5 hours, and then quenched with 1,4-dibromobutane (4.2 g, 0.2 mole). After being stirred for 3 hours, the mixture was poured into ethyl acetate, and then washed with water and brine. The organic solution was then dried ($Na_2SO_4$) and concentrated to an oil. The crude product was purified by flash chromatography over silica gel column. The 4-(4-bromobutyl)-1-(1,3-dithian-2-yl)ethylbenzene thus purified was a light oil, 22.3 g.

ANALYSIS

Calculated for $C_{15}H_{21}BrS_2$: 52.17% C 6.13% H.

Found: 52.60% C 6.25% H.

(C) 1-[4-(1,3-dithian-2-yl)ethyl]phenyl-4-(6-fluoro-1,2-benzisoxazol-3-yl]butylpiperidine A mixture of 6-fluoro-3-(4-piperidinyl)-1,2-benzisoxazole (5.4 g, 24.5 mmoles), $K_2CO_3$ (4.2 g, 30 mmoles), 4-(4-bromobutyl)-1-(1,3-dithian-2-yl) ethylbenzene (8.5 g, 24.6 mmoles) in acetonitrile (200 ml) was heated at reflux for 2.5 hours. At the end of the reaction, the mixture was filtered and the solvent was concentrated. The crude (13 g) was purified by flash chromatography over a silica gel column. The material thus purified (8.67 g; 72%) was recrystallized from ethanol (50 ml) and hexane (100 ml) to afford 6.6 g of 1-[4-(1,3-dithian-2-yl)ethyl]phenyl-4-(6-fluoro-1,2-benzisoxazol-3-yl)butylpiperidine as light yellow crystals, m.p.=108°–110° C.

ANALYSIS

Calculated for: 66.91% C 6.86% H 5.78% N.

Found: 66.72% C 6.76% H 5.71% N.

EXAMPLE 104

1-[4-(4'-Acetophenyl)butyl]-4-(6-fluoro-1,2-benzisoxazol-3-yl)piperidine

A solution of 1-[4-(1,3-dithian-2-yl)ethylphenyl]butyl-4-(6-fluoro-1,2-benzisoxazol-3-yl)piperidine (5.6 g, 11.6 mmoles), water (5 ml), and methanol (30 ml), in acetone (50 ml), was treated with mercury (II) perchloroate trihydrate (5 g, 1.1 eq) at room temperature. After 30 minutes, the reaction was completed. The solids were filtered, and the solvent was removed on a rotary evaporator. The crude product was dissolved in ethyl acetate (500 ml) and washed with water, brine, then dried over $Na2SO_4$. The solvent was removed to give a crude oil. The purification was by flash chromatography over a silica gel column. The oil thus obtained (2.67 g, 50%) was combined with 1.1 g of oil prepared in the same fashion. Crystallization from ethanol (10 ml) and hexane (20 ml) yielded 1-[4-(4'-acetophenyl) butyl]-4-(6-fluoro-1,2-benzisoxazol-3-yl)piperidine as off-white crystals, 2.32 g, m.p.=85°–86° C.

ANALYSIS

Calculated for $C_{24}H_{27}FN_2O_2$: 73.07% C 6.90% H 7.10% N.

Found: 72.68% C 7.05% H 7.09% N.

EXAMPLE 105

1-[4-[3-[4-(6-Fluoro-1,2-benzisoxazol-3-yl)-1-piperidinyl]propylamino]-3-methoxyphenyl] ethanone To a stirred suspension of sodium hydride (0.37 g, 0.007 mol of a 50% oil dispersion), in dimethylformamide (20 ml) was added, dropwise, 1-[4-[3-[4-(6-fluoro-1,2-benzisoxazol-3-yl)-1-piperidinyl]propylamino]-3hydroxyphenyl]ethanone (2.9 g, 0.007 mol) dissolved in dimethylformamide (25 ml). The reaction was stirred at ambient temperature for 15 minutes, and then it was cooled with an ice bath to about 5° C., whereupon methyl iodide (1.0 g, 0.007 mol) in dimethylformamide (1 ml) was added dropwise. The reaction was stirred at ambient temperature for 30 min, and then water was added. The resulting aqueous mixture was extracted with ethyl acetate, the extract washed with water, dried ($MgSO_4$), and the solvent was concentrated to afford 4.9 g of a brown oil, which solidified on standing. The solid was flash chromatographed on silica gel. The appropriate fractions were concentrated to yield 2.7 g of product as a yellow solid. Recrystallization from toluene-hexane yielded 2.0 g (67%) of analytically pure 1-[4-[3-[4-(6-fluoro-1,2-benzisoxazol-3-yl)-1-piperidinyl]propylamino]-3-methoxyphenyl]ethanone as a yellow solid, m.p.=96°–98° C.

ANALYSIS

Calculated for $C_{24}H_{28}FN_3O_3$: 67.75% C 6.63% H 9.88% N.

Found: 67.93% C 6.72% H 9.80% N.

EXAMPLE 106

(2,4-Difluorophenyl)-[1-(phenylmethyl)-3-pyrrolidinyl]methanone oxalate

In a 1 l round bottom flask, a solution of ethyl-N-benzyl-3-pyrrolidine carboxylate (21.8 g, 11.7 mmoles) in 140 ml of 6N HCl was heated at reflux for 2.5 hours. The solution was cooled and the solvent was removed to dryness with a vacuum pump. The residue was then treated with thionyl chloride (100 ml) for 16 hours at room temperature. After the reaction, the excess thionyl chloride was vacuum stripped to dryness (60° C., 4 hrs). To the residue in the flask was added 1,3-difluorobenzene (30 g, 26 mmoles) followed by aluminum chloride (25 g, 18.7 mmoles) in portions at room temperature. When the mixture turned homogeneous (in about 10 minutes) it was then heated at 55° C. for 1 hour. After the reaction was complete, excess 1,3-difluorobenzene was removed under reduced pressure. The residue was partitioned between ice/water and dichloromethane (700 ml) and basified with 50% NaOH solution to pH 10. The dichloromethane solution was washed with water and brine, then dried over anhydrous $MgSO_4$. The solvent was stripped and the crude oil (31 g) was purified by flash chromatography over a silica gel column. The pure product thus obtained weighed 26 g (74%) as a yellow oil. An analytical sample was prepared by dissolving 4.2 of the oil in ethanol and treating with an ethanol solution of oxalic acid (1.33 g, 14.8 mmoles). To the mixture was added ether dropwise to cause crystallization. Recrystallization from ethanol and ether gave 2.63 g of (2,4 -difluorophenyl)[1-phenylmethyl)-3-pyrrolidinyl]methanone oxalate as white crystals, m.p.=114°–116° C.

ANALYSIS

Calculated for $C_{20}H_{19}FNO_5$: 61.38% C 4.89% H 3.58% N.

Found: 61.16% C 4.80% H 3.60% N.

EXAMPLE 107

6-Fluoro-3-[1-phenylmethyl)-3-pyrrolidinyl]-1,2-benzisoxazole fumarate (A) (2,4-difluorophenyl)[1-(phenylmethyl)-3-pyrrolidinyl]methanone oxime To the compound (2,4-difluorophenyl)[1-(phenylmethyl)-3-pyrrolidinyl]methanone (22 g) in 95% ethanol (350 ml) and water (100 ml) was added $NH_2OH.HCl$ (10.1 g) and ammonium acetate (12.7 g, 2.1 eq). The resulting mixture was refluxed for 3.5 hours. The mixture was then allowed to stir at room temperature for 24 hours. The reaction mixture was concentrated to remove ethanol, poured into water (500 ml), and extracted with dichloromethane (500 ml). This was followed by washing with water, brine, and drying over magnesium sulfate. The product was concentrated to an oil and purified by column chromatography to yield 12 g of (2,4-difluorophenyl)[1-(phenylmethyl)-3-pyrrolidinyl]methanone oxime.

(B) 6-fluoro-3-[1-(phenylmethyl)-3-pyrrolidinyl]-1,2-benzisoxazole fumarate

A mixture of (2,4-difluorophenyl)[1-(phenylmethyl)-3-pyrrolidinyl]methanone oxime (10.8 g, 34.2 mmoles), potassium hydroxide (10 g), water (100 ml), and ethanol (100 ml) was heated at reflux for 2 hr. At the end of the reaction, the solution was cooled and ethanol was removed on a rotary evaporator. The aqueous mixture was diluted with water (100 ml) then extracted with dichloromethane (500 ml). The organic solution was washed with brine and dried over anhydrous $MgSO_4$. The solution was concentrated to an oil (9.8 g). The crude product was purified by flash chromatography over a silica gel column. The product thus obtained weighed 4.46 g (44%) as a light yellow oil. The oily product was dissolved in ethanol, and then treated with a solution of fumaric acid (1.73 g, 1.0 eq) in ethanol. Crystallization took place slowly with the addition of isopropyl ether. Recrystallization from ethanol (15 ml) gave 4.6 g of 6-fluoro-3-[1-(phenylmethyl)-3-pyrrolidinyl]-1,2-benzisoxazole fumarate as white crystals, m.p.=142°–144° C.

ANALYSIS

Calculated for $C_{22}H_{21}FN_2O_5$: 64.07% C 5.13% H 6.81% N.

Found: 64.11% C 5.05% H 6.89% N.

EXAMPLE 108

(E)-1-[4-[(4-bromo-2-butenyl)oxy]-3-methoxyphenyl]ethanone

A mixture of 4-hydroxy-3-methoxyacetophenone (10 g, 59 moles), $K_2CO_3$ (10 g, 1.2 q) and 1,4-dibromo-2-butene (>95% trans, Aldrich, 18 g, 1.2 eq) in acetone (500 ml) was heated at 55° C. for 3 hr. At the end of the reaction, the solvent was concentrated. The crude product was extracted into dichloromethane (750 ml) and the insolubles were filtered; then the solution was concentrated again to an oil. Purification on a silica gel column ($SiO_2$, 100 g, eluted with dichloromethane) yielded 7.25 g (40%) of white solid. Recrystallization from ether gave analytically pure (E)-1-[4-[(4-bromo-2-butenyl)oxy]-3-methoxyphenyl]ethanone (3.91 g), m.p.=71°–72° C.

ANALYSIS

Calculated for $C_{13}H_{15}BrO_3$: 52.19% C 5.50% H.

Found: 52.12% C 4.94% H.

EXAMPLE 109

4-(3-Chloropropoxy)-3-methoxybenzaldehyde

A mixture of vanillin (30.4 g, 0.2 mol), $K_2CO_3$ (27.6 g) and acetone (150 ml) was stirred and refluxed for 0.5 hours. Heating was removed and 1-bromo-3-chloropropane (40.8 g, 0.26 mol) in acetone was added dropwise. The reaction was stirred and refluxed for 16 hours, and then it was poured into water. The aqueous mixture was extracted with diethyl ether, the extract was dried ($MgSO_4$), and the solution, was concentrated to afford an oil, which upon evacuation solidified to a white solid (50.2 g). An 8.0 g sample was flash chromatographed on silica gel with 50% ethyl acetate-hexane as eluent. Concentration of appropriate fractions gave 2.7 g (37%) of 4-(3-chloropropoxy)-3-methoxybenzaldehyde as a white solid m.p.=53°–55° C.

ANALYSIS

Calculated for $C_{11}H_{13}ClO_3$: 57.78% C 5.73% H.

Found: 57.21% C 5.52% H.

EXAMPLE 110

6-Fluoro-3-(3-pyrrolidinyl)-1,2-benzisoxazole hydrochloride

A mixture of 3-(6-fluoro-1,2-benzisoxazol-3-yl)-1-pyrrolidinylcarboxylic acid ethenyl ester (5.1 g, 18.4 mmol, hydrochloride acid (5 ml), and isopropyl alcohol (50 ml) was heated at reflux for 3.5 hr. At the end of the reaction, the solvent was reduced to about 30 ml on a rotary evaporator and the mixture was cooled to 0° C. for 2 hr. The crystals were collected by filtration and rinsed with cold isopropyl alcohol. The 6-fluoro-3-(3-pyrrolidinyl)-1,2-benzisoxazole hydrochloride product weighed 3.09 g (69%), m.p.=225°–227° C.

ANALYSIS

Calculated for $C_{11}H_{11}FN_2O.HCl$: 54.44% C 4.99% H 11.54% N.

Found: 54.35% C 4.99% H 11.38% N.

EXAMPLE 111

1-[4-[3-[4-(6-Fluoro-1,2-benzisoxazol-3-yl)-1-piperidinyl]propylamino]-3-hydroxyphenyl]ethanone A mixture of N-[3-[4-(6-fluoro-1,2-benzisoxazol-3-yl)-1-piperidinyl]propyl-6-acetyl-2-benzoxazolinone (6.0 g, 0.014 mol) and 10% aqueous sodium hydroxide (50 ml) was stirred and refluxed for 40 minutes. Water was added and the reaction was made acidic with 5% hydrochloric acid. Saturated $Na_2CO_3$ was added until effervescence ceased. The aqueous mixture was extracted with dichloromethane. The dichloromethane extract was washed (water), dried ($K_2CO_3$) and concentrated to afford 2.6 g of a tacky solid. The crude solid was treated with saturated $NaHCO_3$, and extracted into dichloromethane. The dichloromethane was washed (brine and then water), and dried ($MgSO_4$) yield. The organic extract was then concentrated to 2.4 g of a brown solid, which was combined with another sample to yield 5.0 g. This sample was flash chromatographed on silica. A small sample (0.25 g) was recrystallized from toluene to yield 1-[4-[3-[4-(6-fluoro-1,2-benzisoxazol-3-yl)-1-piperidinyl]propylamino]-3-hydroxyphenyl]ethanone as a brownish solid, 0.15 g, m.p.=150°–152° C.

ANALYSIS

Calculated for $C_{23}H_{26}FN_3O_3$: 67.14% C 6.37% H 10.21% N.

Found: 67.54% C 6.58% H 9.95% N.

EXAMPLE 112

1-[3-Acetylamino-4-[3-chloropropoxy)phenyl] ethanone

A stirred mixture of 1-[3-acetylamino-4-hydroxyphenyl] ethanone (7.7 g, 0.04 mol), $K_2CO_3$ (5.7 g), 3-chloro-1-bromopropane (8.9 g, 0.056 mol), and acetone (100 ml) was refluxed for 16 hours. The reaction was allowed to cool to ambient temperature, and filtered. Concentration of the filtrate yielded 8.5 g of a white solid. The solid was recrystallized from toluene and then from ethanol to afford 6.5 g of an off-white solid. A 3.3 g sample of this material was flash chromatographed on silica gel. Concentration of the appropriate fractions afforded 2.8 g of a white solid. The solid was recrystallized from toluene and then from ethanol-water to yield 2.2 g (51%) of 1-[3-acetylamino-4-(3-chloropropoxy)phenyl]ethanone as a white solid, m.p.=124°–126° C.

ANALYSIS

Calculated for $C_{13}H_{16}ClNO_3$: 57.89% C 5.98% H 5.19% N.

Found: 57.08% C 5.85% H 5.13% N.

EXAMPLE 113

N-[2-(3-hydroxypropoxy)phenyl]acetamide

A stirred mixture of 2-hydroxyphenylacetamide (10.0 g, 0.066 mol), $K_2CO_3$ (6.9 g), 3-bromopropanol (12.8 g, 0.012 mol), and acetone (250 ml) was refluxed for 16 hours. The reaction mixture was allowed to cool, and then it was filtered. The filtrate was concentrated to yield 19.0 g of a thick, broom oil. The oil was distilled with a Kugelrohr apparatus and 11.2 g (82%) of a viscous, orange oil was collected. The oil solidified upon standing. An analytical sample was obtained by recrystallization from ethyl acetate to afford the alcohol as an off-white solid m.p.=78°–80° C.

ANALYSIS

Calculated for $C_{11}H_{15}NO_3$: 63.14% C 7.23% H 6.69% N.

Found: 63.10% C 7.32% H 6.64% N.

EXAMPLE 114

4-[4-(6-Fluoro-1,2-benzisoxazol-3-yl)-1-piperidinyl] butyl bromide

A mixture of 6-fluoro-3-(4-piperidinyl)-1,2-benzisoxazole (12 in, 55 mmol), $K_2CO_3$ (13 m) and 1,4-dibromobutane (20 m, 9.3 mmol, 1.7 eq) in acetonitrile (300 ml) was stirred at room temperature overnight. The inorganic material was filtered. The solution was concentrated to ~80 ml, when crystals crashed out. The product was filtered to yield 14.16 m (73%), m.p.=243°–245° C.

ANALYSIS

Calculated for $C_{16}H_{20}BrFN_2O$: 54.09% C 5.67% H 7.89% N.

Found: 54.13% C 5.52% H 7.83% N.

EXAMPLE 115

2-[4-(6-Fluoro-1,2-benzisoxazol-3-yl)-1-piperidinyl] ethyl acetate fumarate

A mixture of 6-fluoro-3-(4-piperidinyl)-1,2-benzisoxazole (3.0 gm, 13.6 mmol), $K_2CO_3$ (3.5 m, 25 mmol), 2-bromoethyl acetate (4 gm, 26.5 mmol) in acetonitrile (50 ml) was heated at reflux for 4 hr. After cooling to room temperature, the inorganic salts were filtered and washed with DCM (dichloromethane 50 ml). The organic solvent was removed on a rotary evaporator to give an oil. The oily product was purified on a flash chromatography column (60 gm of $SiO_2$; eluted with MeOH 2%–4% in DCM). The pure product thus obtained weighed 4.43 gm. This oil was dissolved in ethanol and treated with a solution of fumaric acid (1.2 gm) in ethanol. The salt crystallized out at room temperature to yield 3.44 gm (57%), m.p.=154°–155° C.

ANALYSIS

Calculated for $C_{16}H_{19}FN_2O_3.C_4H_4O_4$: 56.86% C 5.49% H 5.63% N.

Found: 56.75% C 5.41% H 6.54% N.

EXAMPLE 116

N-[2-[4-(6-Fluoro-1,2-benzisoxazol-3-yl)-1-piperidinyl]ethyl]morpholine

A mixture of 6-fluoro-3-(4-piperidinyl)-1,2-benzisoxazole (3.0 gm, 13.6 mmol), 2-chloroethyl morpholine hydrochloride (4.46 gm, 29.7 mmol) and $K_2CO_3$ (7.3 gm, 2.2 eq) in acetonitrile (60 ml) was heated at reflux for 24 hr. The crude mixture was diluted with DCM and filtered. The solvent was concentrated to an oil (~7.1 gm). Purification on a silica gel column (55 gm, $SiO_2$, eluted with MeOH:DCM) yielded a solid product weighing 4 gm. Recrystallization from hot ethanol yielded 2.1 gm (48%), m.p.=131°–132° C.

ANALYSIS

Calculated for $C_{18}H_{24}FN_3O_2$: 64.84% C 7.26% H 12.60% N.

Found: 64.80% C 7.09% H 12.77% N.

EXAMPLE 117

N-[2-[4-(6-Fluoro-1,2-benzisoxazol-3-yl)-1-piperidinyl]ethyl]phthalimide

A mixture of 6-fluoro-3-(4-piperidinyl)-1,2-benzisoxazole (5 15 gm 23 4 mmol) $K_2CO_3$ (4.2 gm, 30.4 mmol) and 2-bromoethyl phthalimide (7.13 gm, 28 mmol) in acetonitrile (250 ml) was heated at reflux for 3.5 hr. The solids and solvent were removed. The residue was purified by flash chromatography ($SiO_2$, 110 m, eluted with 2–4% $CH_3OH$:DCM). The product thus obtained weighed 7.8 gm (84%). Part of the material was recrystallized to give 2.35 gm of off white crystals, m.p.=148°–149° C.

ANALYSIS

Calculated for $C_{22}H_{20}FN_3O_3$: 67.17% C 5.12% H 10.68% N.

Found: 67.01% C 5.20% H 10.76% N.

EXAMPLE 118

2-[4-(6-Fluoro-1,2-benzisoxazol-3-yl)-1-piperidinyl] ethyl methyl ether fumarate A mixture of 6-fluoro-3-(4-piperidinyl)-1,2-benzisoxazole (3.75 gm, 17 mmol), $K_2CO_3$ (3 gm, 21.7 mmol), bromoethyl methyl ether (2.84 gm, 20.4 mmol) in acetonitrile (150 ml) was heated at reflux for 3.5 hr. The reaction was cooled. The inorganics were filtered and rinsed with DCM. The organic solution was concentrated down to an oil (7 gm). Purification on a flash chromatography column ($SiO_2$, 45 gm; eluted with methanol/DCM) gave a light yellow oil as product (4 gm, 87%). This oil was dissolved into ethanol and treated with a solution of fumaric acid (1.67 gm) in ethanol (20 ml). White crystals (5.15 gm) were collected, m.p.=157°–158° C.

ANALYSIS

Calculated for $C_{15}H_{19}FN_2O_2.C_4H_4O_4$: 57.86% C 5.88% H 7.10% N.

Found: 57.53% C 5.94% H 6.94% N.

EXAMPLE 119

4-[4-(6-Fluoro-1,2-benzisoxazol-3-yl)-1-piperidinyl] butyl acetate fumarate

A mixture of 6-fluoro-3-(4-piperidinyl)-1,2-benzisoxazole (9.5 gm, 41 mmol), $K_2CO_3$ (7.2 m, 51 mmol), and 4-bromobutyl acetate (10 gm, 51 mmol) in acetonitrile (200 ml) was heated at reflux for 3½ hr. At the end of the reaction, the solution was cooled and filtered. The inorganic salt was washed with DCM (50 ml). The organic solvent was removed. The residue was purified on a flash chromatography column (packed with Sorbsil C30 silica gel, 100 gm, eluted with DCM, 1 liter, increasing methanol from 2 to 4%, 2.51). The material thus purified weighed 12.92 gm (89%). A small sample (1.67 gm) was dissolved in ethanol and treated with 1 equivalent of fumaric acid (580 mg) in ethanol to yield white crystals: 1.8 gm, m.p.=142°–143° C.

ANALYSIS

Calculated for $C_{18}H_{23}FN_2O_3.C_4H_4O_4$: 58.66% C 6.04% H 6.22% N.

Found: 58.56% C 6.02% H 6.13% N.

EXAMPLE 120

4-[4-(6-Fluoro-1,2-benzisoxazol-3-yl)-1-piperidinyl] butanol fumarate

A mixture of 4-[4-(6-fluoro-1,2-benzisoxazol-3-yl)-1-piperidinyl]butyl acetate (11.5 gm, 34.4 mmol), 15% NaOH (100 ml) and ethanol (100 ml) was heated at reflux for 4 hrs. After cooling to room temperature, the base was neutralized with HCl to pH=7. The solution was concentrated down to a small volume ml), then extracted with DCM. The DCM solution was washed with brine and dried over $MgSO_4$. The solvent was concentrated to give ~10 gm of crude oil. Purification by flash chromatography (Sorbsil C-30, 100 gm, eluted with MeOH:DCM, 3 liters) yielded 9.8 gm of white solid. The sample for testing was prepared by treatment of the free base (2.0 gm) with fumaric acid (780 mg, 1.0 eq) in ethanol. The crystals were collected and dried: 1.5 gm, m.p.=131°–132° C.

ANALYSIS

Calculated for $C_{16}H_{21}FN_2O_2.C_4H_4O_4$: 58.82% C 6.17% H 6.86% N.

Found: 58.81% C 6.37% H 6.66% N.

EXAMPLE 121

4-[4-(6-Fluoro-1,2-benzisoxazol-3-yl)-1-piperidinyl] butyl decanoate fumarate

To a solution of 4-[4-(6-fluoro-1,2-benzisoxazol-3-yl)-1-piperidinyl]butanol (2.0 gm, 6.84 mmol), triethylamine (1.0 gm, 10 mmol) in DCM (70 ml) decanoyl chloride (1.7 gm, 8.9 mmol) was added dropwise at room temperature. The mixture was stirred for 1 hr., then was concentrated to a crude solid. The solid was extracted into ethyl acetate, and the insoluble salts were filtered. The solvents were removed. The crude product was purified by flash chromatography (Sorbsil C-30, 30 in, eluted -with a mixture of MeOH in DCM). The oil thus obtained (2.5 gm, 81%) was converted to a fumarate salt with fumaric acid (650 mg), 1.0 eq) in ethanol. Crystals were collected: 1.48 gm, m.p.=109°–110° C.

ANALYSIS

Calculated for $C_{26}H_{39}FN_2O_3.C_4H_4O_4$: 64.04% C 7.70% H 4.98% N.

Found: 64.30% C 7.86% H 4.78% N.

EXAMPLE 122

3-[4-(6-Fluoro-1,2-benzisoxazol-3-yl)-1-piperidinyl] propyl decanoate fumarate

To a solution 3-[4-(6-fluoro-1,2-benzisoxazol-3-yl)-1-piperidinyl]propanol (1.81 gm, 6.5 mmol) triethylamine (0.9 gm, 9.0 mmol) in DCM (45 ml) was added decanoyl chloride (1.5 gm, 7.8 mmol) dropwise at room temperature. The mixture was stirred for 20 minutes, then concentrated down to a crude solid. The solid was extracted into EtOAc (20 ml), and the insoluble salts were filtered. The EtOAc was removed. The crude oil was purified by flash chromatography (Sorbsil C-30, 30 gm; eluted with MeOH:DCM). The oil thus obtained (2.54 gm, 90%) was converted to a fumarate salt with fumaric acid (670 mg) in ethanol. The crystals collected weighed 1.61 gm, m.p.=100°–102° C.

ANALYSIS

Calculated for $C_{25}H_{27}FN_2O_3.C_4H_4O_4$: 63.52% C 7.54% H 5.11% N.

Found: 63.63% C 7.74% H 5.03% N.

EXAMPLE 123

N,N-Diethyl-4-[4-(6-fluoro-1,2-benzisoxazol-3-yl)-1-piperidinyl]butyl carbamate fumarate To a mixture of 4-[4-(6-fluoro-1,2-benzisoxazol-3-yl)-1-piperidinyl]butanol (1.55 gm, 5.3 mmol) potassium t-butoxide (750 mg, 6.7 mmol) in THF (100 ml), diethylcarbamyl chloride (900 mg, 6.63 mmol) was added dropwise at room temperature. The mixture was stirred for 2 hr, then the solvent was removed. The residue was extracted into DCM. The DCM solution was washed with brine and dried over $MgSO_4$. The solution was concentrated. The product was purified on a flash chromatography column ($SiO_2$, 14 gm, eluted with 2% MeOH in DCM), to yield 1.84 gm of oil. This oil was dissolved into ethanol (~5 ml) and treated with a solution of fumaric acid (850 mg, 1.0 eq) in ethanol. Crystallization was induced with a small volume of isopropyl ether to produce 2.09 gm, m.p.=152°–153° C.

ANALYSIS

Calculated for $C_{21}H_{30}FN_3O_3.C_4H_4O_4$: 59.16% C 6.75% H 8.28% N.

Found: 59.17% C 6.84% H 8.16% N.

EXAMPLE 124

N-Methyl-4-[4-(6-fluoro-1,2-benzisoxazol-3-yl)-1-piperidinyl]butyl carbamate fumarate To a mixture of 4-[4-(6-fluoro-1,2-benzisoxazol-3-yl)-1-piperidinyl]butanol (1.84 gm, 6.3 mmol), $K_2CO_3$ (850 mg) in chloroform, methyl isocyanate (448 mg, 7.7 mmol and 360 mg, 6.2 mmol) was added dropwise in two portions. The mixture was filtered and concentrated to a crude oil. Purification was done on a flash chromatography column ($SiO_2$, 11 gm, eluted with 2% $CH_3OH$ in DCM) to yield a light yellow oil (2.05 gm, 93%). This oil was dissolved into ethanol and treated with a solution of fumaric acid (800 mg, 1.0 eq). Crystallization was induced with drops of isopropyl ether. Weight: 1.36 in, m.p.=96°–98° C.

ANALYSIS

Calculated for $C_{18}H_{24}FN_3O_3.C_4H_4O_4$: 56.76% C 6.06% H 9.02% N.

Found: 56.27% C 6.03% H 8.86% N.

EXAMPLE 125

2-[2-[4-(6-Fluoro-1,2-benzisoxazol-3-yl)-1-piperidinyl]ethyl]-1,3-dioxane fumarate A mixture of 6-fluoro-3-(4-piperidinyl)-1,2-benzisoxazole (2.0 gm, 9.1 mmol), $K_2CO_3$ (1.5 gm, 10.9 mmol) and bromoethyl-1,3-dioxane (2.1 gm, 10.7 mmol) in acetonitrile (50 ml) was heated at reflux for 3 hr. At the end, the insolubles were filtered and rinsed with DCM and the filtrate was evaporated down. The crude mixture was purified by flash chromatography over a silica gel column (Sorbsil C-30, 25 gm; eluted with DCM and MeOH (1–3%) in DCM). The fractions containing the pure product were combined and concentrated to give 3.13 gm of oil. The oil was treated with a fumaric acid (1.0 in) ethanol solution. The crystals were collected: 3.98 gm (77%), m.p.=161°–162° C.

ANALYSIS

Calculated for $C_{18}H_{23}FN_2O_3.C_4H_4O_4$: 58.66% C 6.04% H 6.22% N.

Found: 58.69% C 5.96% H 6.20% N.

EXAMPLE 126

2-[4-(6-Fluoro-1,2-benzisoxazol-3-yl-1-piperidinyl] ethanol hemifumarate (A) 2-[4-(6-Fluoro-1,2-benzisoxazol-3-yl)-1-piperidinyl]ethyl acetate 2-[4-(6-Fluoro-1,2-benzisoxazol-3-yl)-1-piperidinyl] ethyl acetate was prepared according to Example 115.

(B) 2-[4-(6-Fluoro-1,2-benzisoxazol-3-yl-1-piperidinyl]ethanol hemifumarate

2-[4-(6-Fluoro-1,2-benzisoxazol-3-yl)-1-piperidinyl] ethyl acetate (10.58 gm, 34.6 mmol), 15% NaOH (100 ml) and ethanol (100 ml) was heated at reflux for 4 hr. The solution was cooled (~5° C.) and neutralized with HCl to pH~7. The ethanol was removed under reduced pressure. The aqueous solution was basified with $NaHCO_3$ and extracted with DCM (2×200 ml). The DCM solution was washed with brine and dried over $MgSO_4$ and evaporated to give a white solid: 6.88 gm (75%). A sample (2.03 gm) was dissolved in ethanol and treated with fumaric acid (600 mg, 1.0 eq). Crystallization was induced with drops of isopropyl ether to yield off-white crystals: 143 in, m.p.=159°–161° C.

ANALYSIS

Calculated for $C_{14}H_{17}FN_2O_2.0.5C_4H_4O_4$: 59.62% C 5.94% H 8.69% N.

Found: 59.55% C 5.95% H 8.53% N.

EXAMPLE 127

2-[4-(6-Fluoro-1,2-benzisoxazol-3-yl)-1-piperidinyl] ethyl decanoate fumarate

A mixture of 2-[4-(6-fluoro-1,2-benzisoxazol-3-yl)-1-piperidinyl]ethyl alcohol (1.6 gm, 5 mmol) and triethylamine (800 mg, 8 mmoles) in chloroform (100 ml) was treated with decanoyl chloride (1.3 gm, 7.2 mmol) dropwise at room temperature. The mixture was stirred for 4 hours. The solvent was removed to leave a crude solid. The solid was dissolved into a small amount of DCM (15 ml), then was filtered. The solution was concentrated.

The purification was done by flash chromatography over a silica gel column (Sorbsil C-30, 30 gm; eluted with MeOH: DCM). The purified oil (2.45 gm, 95%) was treated with a fumaric acid (660 gm, 1.0 eq)/ethanol solution (15 ml). Crystallization was induced by adding drops of ether; yield: 1.97 gm, m.p.=109°–110° C.

ANALYSIS

Calculated for $C_{24}H_{35}FN_3O_3.C_4H_4O_4$: 62.90% C 7.35% H 5.24% N.

Found: 62.93% C 7.30% H 5.14% N.

EXAMPLE 128

N,N-Diethyl-2-[4-(6-fluoro-1,2-benzisoxazol-3-yl)-1-piperidinyl]ethylcarbamate fumarate To a mixture of 2-[4-(6-fluoro-1,2-benzisoxazol-3-yl)-1-piperidinyl]ethanol (1.6 gm, 6 mmol) and potassium t-butoxide (860 mg, 7.6 mmol) in THF (100 ml) diethyl carbamyl chloride (1.03 gm, 7.5 mmol) was added dropwise at room temperature. The mixture was stirred for 4 hr. The reaction mixture was concentrated to a crude solid. The solid was dissolved in DCM and purified on a flash chromatography column (Sorbsil C-30, 27 gm; eluted with a MeOH: DCM mixture). The product thus purified as a light oil (2.2 gm, 91%) was dissolved into ethanol and treated with a fumaric acid (690 mg, 1.0 eq)/ethanol solution (15 ml). Crystallization on cooling yielded 2.15 gm of white crystals, m.p.=133°–135° C.

ANALYSIS

Calculated for $C_{19}H_{26}FN_3O_3.C_4H_4O_4$: 57.61% C 6.31% H 8.76% N.

Found: 57.49% C 6.25% H 8.54% N.

EXAMPLE 129

2-[4-(6-Fluoro-1,2-benzisoxazol-3-yl)-1-piperidinyl] ethylamine hemifumarate (A) 2-[4-(6-fluoro-1,2-benzisoxazol-3-yl)-1-piperidinyl]ethyl phthalimide 2-[4-(6-fluoro-1,2-benzisoxazol-3-yl)-1-piperidinyl]ethyl phthalimide was prepared according to Example 117.

(B) 2-[4-(6-Fluoro-1,2-benzisoxazol-3-yl)-1-piperidinyl]ethylamine hemifumarate

A mixture of 2-[4-(6-fluoro-1,2-benzisoxazol-3-yl)-1-piperidinyl]ethyl phthalimide (4.6 in, 11.7 mmol) and hydrazine monohydrate (1.17 gm, 23.4 mmol) in methanol (50 ml) was heated at reflux overnight. At the end of the reaction, methanol was removed to leave a crude solid. This was stirred with water (150 ml) and acidified with HCl to pH=2. The insolubles were filtered. The aqueous solution was basified with 50% NaOH then extracted with DCM (2×250 ml). The DCM solution was washed with brine and dried over $MgSO_4$. The solvent was removed to produce a colorless oil: 2.12 gm. This oil was treated with a solution of fumaric acid (935 mg, 1.0 eq) in ethanol. The salt crystallized out: 0.99 gm, 203°–205° C. A second crop of 0.73 in (m.p.=198°–200° C.) was collected later.

ANALYSIS

Calculated for $C_{14}H_{18}FN_3O.0.5C_4H_4O_4$: 59.80% C 6.27% H 13.07% N.

Found: 59.51% C 6.35% H 13.31% N.

EXAMPLE 130

2-[4-(6-Fluoro-1,2-benzisoxazol-3-yl)-1-piperidinyl] ethyl decanamide fumarate

To a mixture of 2-[4-(6-fluoro-1,2-benzisoxazol-3-yl)-1-piperidinyl]ethylamine (1.49 gm, 5.5 mmol) and triethylamine (1.0 gm, 10 mmol) in chloroform (50 ml) decanoyl chloride (1.26 gm, 6.6 mmol) was added at room temperature. The mixture was stirred for 3 hr at room temperature. The solvent was stripped down to a crude mixture. This crude mixture was purified by flash chromatography over a silica gel column ($SiO_2$, 20 gm; eluded with a solution of MeOH (0–3%) in DCM). The fractions containing the pure product were pooled and concentrated to give 2.3 gm of oil. This oil was converted to a fumarate salt by treatment with fumaric acid (655 mg) in ethanol. The ethanol was concentrated down to a small volume and 3 volumes of isopropyl ether was added. This mixture was stirred overnight to cause crystallization. The solids were collected, weighed: 1.83 gm (60.5%), m.p.=108°–110° C.

ANALYSIS

Calculated for $C_{24}H_{36}FN_3O_2.C_4H_4O_4$: 63.02% C 7.56% H 7.87% N.

Found: 62.42% C 7.58% H 7.66% N.

EXAMPLE 131

2-[4-(6-Fluoro-1,2-benzisoxazol-3-yl)-1-piperidinyl] ethyl acetamide fumarate

A mixture of 2-[4-(6-fluoro-1,2-benzisoxazol-3-yl)-1-piperidinyl]ethylamine (2.56 g, 9.7 mmol) and triethylamine (1.45 gm, 14.5 mmol) in DCM (50 ml) was treated with dropwise addition of acetyl chloride (1.0 gm, 12.7 mmol) at room temperature. The mixture was stirred for 4 hr at room temperature. The reaction mixture was diluted with DCM and washed with brine. The organic solution was dried over $MgSO_4$ and concentrated to a crude oil. The crude oil was purified by flash chromatography over a silica gel column ($SiO_2$, 20 gm; eluted with (0–2%) $CH_3OH$ in DCM). The pure product thus obtained weighed 1.36 gm (46%). It was converted to a fumarate salt by treatment with fumaric acid (517 mg) in ethanol. Recrystallization from ethanol gave white crystals; weight: 1.53 gm, m.p.=132°–133° C.

ANALYSIS

Calculated for $C_{16}H_{20}FN_3O_2.C_4H_4O_4$: 57.00% C 5.74% H 9.97% N.

Found: 57.05% C 5.85% H 9.95% N.

EXAMPLE 132

2-[[2-[4-(6-Fluoro-1,2-benzisoxazol-3-yl)-1-piperidinyl]ethyl]amino]ethyl acetate fumarate A mixture of 2-[4-(6-fluoro-1,2-benzisoxazol-3-yl)-1-piperidinyl]ethylamine (2.0 gm, 7.6 mmol), $K_2CO_3$ (1.38 gm, 10 mmol) and bromoethyl acetate (1.40 gm, 8.3 mmol) in acetonitrile (50 ml) was heated at reflux for 4 hr. At the end, the insolubles were filtered off and rinsed with DCM. The solvent was evaporated down. The crude mixture was purified by flash chromatography over a silica gel column (Sorbsil C-30, 30 gm; eluted with 2% $CH_3OH$ in DCM, 800 ml). The oil (1.15 gm) thus obtained was treated with a solution of fumaric acid (358 mg) in ethanol. Crystallization was induced by adding drops of ethyl ether, yield: 1.09 gm, m.p.=116°–118° C.

ANALYSIS

Calculated for $C_{18}H_{24}FN_3O_3.C_4H_4O_4$: 56.77% C 6.06% H 9.03% N.

Found: 56.32% C 5.97% H 8.94% N.

EXAMPLE 133

N-[2-(4-(6-fluoro-1,2-benzisoxazol-3-yl)-1-piperidinyl]ethyl]carbamate fumarate

A mixture of 2-[4-(6-fluoro-1,2-benzisoxazol-3-yl)-1-piperidinyl]ethylamine (2.0 gm, 7.6 mmol) and triethylamine (1.0 gm, 10 mmol) in DCM (50 ml) was treated with methyl chloroformate (860 mg, 9.12 mmol) dropwise at room temperature. The mixture was stirred for 1 hr. The reaction mixture was diluted with DCM and washed with brine. The organic solution was dried over $MgSO_4$ and concentrated to a crude oil. The purification was done by flash chromatography over a silica gel column (28 gm of Sorbsil C-30, eluted with DCM and MeOH/DCM). The pure oil thus obtained weighed 2.34 gm. It was converted to a fumarate salt by treatment with fumaric acid (840 mg, 1.0 eq) in ethanol. Crystallization was induced by adding drops of isopropyl ether, yield: 2.31 gm, m.p.=163°–165° C.

ANALYSIS

Calculated for $C_{16}H_{20}FN_3O_3.C_4H_4O_4$: 54.92% C 5.53% H 9.61% N.

Found: 54.49% C 5.45% H 9.24% N.

EXAMPLE 134

Z-2-[2-[4-(6-Fluoro-1,2-benzisoxazol-3-yl)-1-piperidinyl]ethyl]hexahydro-1H-isoindole-1,3-dione fumarate A mixture of 1-(2-aminoethyl)-4-(6-fluoro-1,2-benzisoxazol-3yl)piperidine (3.77 gm, 14.3 mmol) and cis-1,2-cyclohexanedicarboxylic anhydride (2.82 gm, 18.2 mmol, 1.25 eq) in dry pyridine (50 ml) was heated at 65° C. for 48 hr. The dark brown solution was concentrated to dryness on a rotary evaporator. The crude residue was purified twice by flash chromatography over a silica gel column ($SiO_2$, 45 gm and 50 gm, eluted with DCM and 1% $CH_3OH$ in DCM). The pure product thus obtained 2.35 gm (41%), was converted to the fumarate salt by treatment with fumaric acid (660 mg) in ethanol. The crystals after two recrystallizations weighed 1.37 gm, m.p.=172°–173° C.

ANALYSIS

Calculated for $C_{22}H_{26}FN_3O_3.C_4H_4O_4$: 60.57% C 5.87% H 8.15% N.

Found: 60.40% C 5.55% H 7.82% N.

EXAMPLE 135

(S)-(+)-13-[4-(6-Fluoro-1,2-benzisoxazol-3-yl)-1-piperidinyl]-2-methyl-1-propanol fumarate A mixture of 4-(6-fluoro-1,2-benzisoxazol-3-yl) piperidine (7.2 gm, 32.7 mmol), (S)-(+)-3-bromo-2-methyl-1-propanol (5.0 gm, 32.6 mmol), $K_2CO_3$(7.19 gm, 52 mmol) in acetonitrile (250 ml) was heated at reflux overnight. The insolubles were filtered off. The solvent was removed at reduced pressure and the crude residue was purified by silica gel chromatography ($SiO_2$, 84 gm, eluted with 21 of 1% $CH_3OH$ in DCM) to give the target compound as an off-white solid (8.83 in, 94%). A sample of 1.7 gm was converted to the fumarate salt by treatment with fumaric acid (710 mg) in ethanol. Recrystallization from ethanol yielded 1.74 gm of white crystals, m.p.=119°–12.1° C.

ANALYSIS

Calculated for $C_{20}H_{25}FN_2O_6$: 58.82% C 6.17% H 6.86% N.

Found: 58.81% C 6.24% H 6.76% N.

EXAMPLE 136

4-(6-Fluoro-1,2-benzisoxazol-3-yl)-1-[3-(1-piperidinyl]propyl]piperidine difumarate A mixture of 4-(6-fluoro-1,2-benzisoxazol-3-yl) piperidine (3.0 gm, 13.6 mmol), N-(3-chloropropyl) piperidine hydrochloride (4.05 gm, 20.4 mmol), $K_2CO_3$ (6 gm, 43.4 mmol), tetrabutyl-ammonium hydrogen sulfate (phase transfer catalyst, 2.3 gm) in acetonitrile (100 ml) and water (15 ml) was heated at reflux for 16 hr. The mixture was washed with brine and the layers were separated. The organic solution was concentrated. The crude product (6.4 gm) was purified by flash chromatography over a silica gel column (55 gm, sorbsil C-30; eluted with 2% $CH_3OH$:0°–5% DEA in DCM, 1.41). The oil thus purified (4.5 gm) was treated with fumaric acid (1.6 gm) in ethanol. The solid was collected: weight 3.1 in, m.p.178°–181° C. Recrystallization from ethanol yielded 2.28 gm of white crystals, m.p.=190°–192° C.

ANALYSIS

Calculated for $C_{20}H_{24}FN_3O.2C_4H_4O_4$ 58.22% C 6.28% H 7.27% N.

Found: 58.39% C 6.36% H 7.34% N.

EXAMPLE 137

1-(3-Dimethylaminopropyl)-4-(6-fluoro-1,2-benzisoxazol-3-yl)piperidine difumarate A mixture of 6-fluoro-3-(4-piperidinyl)-1,2-benzisoxazole (3.05 gm, 13.8 mmol), 3-dimethylaminopropyl chloride hydrochloride (3.4 gm, 21 mmol), $K_2CO_3$ (6.2 gm 45 mmol), tetrabutylammonium hydrogen sulfate (phase transfer catalyst, 1.5 gm) in acetonitrile (100 ml) and water (50 ml) was heated at 60° C. overnight. The aqueous phase was separated, the acetonitrile was removed at reduced pressure. The residue was extracted into DCM. The organic solution was washed with $H_2O$ and brine, then dried with $MgSO_4$. The solvent was removed and the crude product (4.3 gm) was treated with fumaric acid (1.58 gm, 1.0eq) in dilute ethanol. The crystals were collected (2.53 gm), m.p.=192°–194° C. Recrystallization from ethanol yielded 2.08 gm of white crystals, m.p.=194°–195° C.

ANALYSIS

Calculated for $C_{17}H_{24}FN_3O_2.C_4H_4O_4$: 55.86% C 6.00% H 7.82% N.

Found: 56.11% C 5.94% H 7.86% N.

EXAMPLE 138

(R)-(−)-3-[4-(6-Fluoro-1,2-benzisoxazol-3-yl)-1-piperidinyl]-2-methyl-1-propanol fumarate A mixture of 4-(6-fluoro-1,2-benzisoxazol-3-yl) piperidine (14.5 gm, 65 mmol), $K_2CO_3$ (10 gm, 72 mmol), (R)-(−)-3-bromo-2-methyl-1-propanol (10 gm, 65.3 mmol), tetrabutylammonium hydrogen sulfate (1.27 gm, phase transfer catalyst) in acetonitrile (300 ml) and $H_2O$ (5 ml) was heated at reflux for 6 hr. The mixture was cooled and the solvent was removed on rotary evaporator. The residue was extracted into methylene chloride (DCM), and the insolubles were filtered. After concentration of the extract, the crude product was purified by flash chromatography over a silica gel column ($SiO_2$, 1.50 gm; eluted with DCM, 11; 2% $CH_3OH$ in DCM, 1.61). The material thus purified weighed 17 gm (89%). The sample for testing was prepared by treatment of a sample (2.28 gm) with fumaric acid (953 mg) in ethanol. The crystals formed slowly upon addition of isopropyl ether. These were collected and dried: weight 1.84 gm, m.p.=114°–115° C.

Elemental ANALYSIS

Calculated for $C_{16}H_{21}FN_2O_2.C_4H_4O_4$: 58.82% C 6.17% H 6.85% N.

Found: 58.48% C 6.08% H 6.57% N.

EXAMPLE 139

3-[1-[3-[4-(1-Methoxyethyl)-2-hydroxyphenoxyl] propyl]-4-piperidinyl]-6-fluoro-1,2-benzisoxazole A mixture of 6-fluoro-3-(4-piperidinyl)-1,2-benzisoxazole (5.7 gm, 26.0 mmol), 4-(3-chloropropoxy)-3-hydroxy-α-methylbenzenemethanol (6.0 g, 26.0 mmol), $NaHCO_3$ (2.4 g, 28.6 mmol), KI (200 mg) and $CH_3CN$ (150 ml) was stirred at reflux under $N_2$ for 17 hours. A TLC allowed a trace of the alkylating side chain, therefore additional 6-fluoro-3-(4-piperidinyl)-1,2-benzisoxazole (0.6 g, 2.7 mmol) and $NaHCO_3$ (0.22 g, 2.6 mmol) was added and the reaction was refluxed 3 hours longer. The cooled reaction was concentrated and the residue was partitioned between EtOAc and $H_2O$. The EtOAc extract was washed with $H_2O$ then brine and after drying with $MgSO_4$ the extract was concentrated to yield 11.9 g of a beige oil. The sample was purified by preparative HPLC (Water's Associates Prep LC/System 500 utilizing 2 silica gel columns and eluting with 5% MeOH—$CH_2Cl_2$). Concentration of later fractions afforded 4.2 g of 4-[3-[4-(6-fluoro-1,2-benzisoxazol-3-yl)-1-piperidinyl]propoxy]-3-hydroxy-α-methylbenzenemethanol. Concentration of earlier fractions gave 4.0 g of a mixture of 4-[3-[4-(6-fluoro-1,2-benzisoxazol-3-yl)-1-piperidinyl]propoxy]-3-hydroxy-α-methylbenzenemethanol and 3-[1-[3-[4-(1-methoxyethyl)-2-hydroxyphenoxy]propyl]-4-piperidinyl]-6-fluoro-1,2-benzisoxazole (the latter was apparently formed by the reaction of the former with MeOH on silica gel).

The mixture was dissolved in anhydrous $Et_2O$ (330 ml) and anhydrous MeOH (100 ml) and ethereal HCl was added. After stirring 1.5 hours, anhydrous $Et_2O$ was added and the resultant solid was collected and dried to yield 2.9 g of a mixture of the respective HCl salts. The solid was suspended in $H_2O$ and was basified with $NH_4OH$. The aqueous mixture was extracted with $CH_2Cl_2$ and the extract was washed with $H_{20}$, dried with $MgSO_4$ and concentrated to yield 2.7 g of a light beige oil. The oil was purified by preparative HPLC (Water's Associates Prep LC/System 500 using 2 silica gel columns and 3% MeOH—$CH_2Cl_2$ as eluent). Concentration of later fractions yielded 0.5 g of 4-[3-[4-(6-fluoro-1,2-benzisoxazol-3-yl)-1-piperidinyl]propoxy]-3-hydroxy-α-methylbenzenemethanol. Concentration of earlier fractions gave an oil that solidified upon standing. The product was triturated with heptane and filtered to yield 1.2 g of a white powder. The compound was recrystallized from EtOH to provide 1.1 g (10%) of 3-[1-[3-[4-(1-methoxyethyl)-2-hydroxyphenoxy]propyl]-4-piperidinyl]-6-fluoro-1,2-benzisoxazole as clean white crystals m.p.=98°–100° C.

ANALYSIS

Calculated for $C_{24}H_{29}FN_2O_4$: 67.27% C 6.82% H 6.54% N. Found: 67.18% C 6.84% H 6.54% N.

EXAMPLE 140

6-Fluoro-3-[1-[3-[(1H-indol-5-yl)oxy]propyl]-4-piperidinyl]-1,2-benzisoxazole

A mixture of 6-fluoro-3-(4-piperidinyl)-1,2-benzisoxazole (2.6 g, 11.8 mmol), $K_2CO_3$ (1.6 g, 11.6 mmol), KI (200 mg), 5-(3-chloropropoxy)indole (2.2 g, 10.5 mmol) and $CH_3CN$ (100 ml) was stirred at reflux under $N_2$ for 18 hours. The cooled reaction was poured into $H_2O$ and the aqueous mixture was extracted with EtOAc. The EtOAc extract was washed 2 times with $H_2O$, 2 times with brine and after drying with $MgSO_4$ the solvent was removed in vacuo to yield 5.1 g of a dark oil. The oil was purified by preparative HPLC (Water's Associates Prep LC/System 500, using 2 silica gel columns and 4% MeOH—$CH_2Cl_2$ as eluent) to afford 2.65 g (65%) of a beige solid. Recrystallization from ethanol gave 2.2 g (54%) of a beige powder, m.p.=118°–121° C.

ANALYSIS

Calculated for $C_{23}H_{24}FN_3O_2$: 70.21% C 6.15% H 10.68% N.

Found: 69.80% C 6.21% H 10.78% N.

EXAMPLE 141

6-Fluoro-3-[1-[3-[(isoquinol-5-yl)oxy]propyl]-4-piperidinyl]-1,2-benzisoxazole sesquifumarate A stirred mixture of 6-fluoro-3-(4-piperidinyl)-1,2-benzisoxazole (2.8 g, 0.013 mol), 5-(3-chloropropoxy) isoquinoline (2.8 g, 0.013 mol), $K_2CO_3$ (1.7 g) and $CH_3CN$ (50 ml) was refluxed for 16 h. The reaction was filtered and the filtrate was concentrated to an oil. The filter cake was treated with $H_2O$, and the aqueous suspension was extracted with $CH_2Cl_2$. The filtrate was also extracted with $CH_2Cl_2$, and the extracts were combined, washed ($H_2O$), dried ($K_2CO_3$) and concentrated to yield 5.4 g of a brown oil. The oil was purified by HPLC on silica gel columns, eluting with $CH_2Cl_2$/MeOH (5%), to afford 2.3 g of a yellow oil. The oil was dissolved in EtOAc and fumaric acid (0–66 g, 1 eq) was added. The mixture was refluxed briefly, and then stirred at ambient temperature for 16 h. The resulting white solid was collected to afford 2.2 g of the fumarate salt. The compound was recrystallized from DMF to yield 1.4 g (18.6%) of the isoquinoline as a sesquifumarate, m.p.=213°–215° C.

ANALYSIS

Calculated for $C_{30}H_{30}FN_3O_8$: 62.17% C 5.22% H 7.25% N.

Found: 62.01% C 5.11% H 7.28% N.

EXAMPLE 142

6-Fluoro-3-[1-[3-[(1-H-indol-4-yl)oxy]propyl]-4-piperidinyl]-1,2-benzisoxazole

A mixture of 6-fluoro-3-(4-piperidinyl)-1,2-benzisoxazole (3.5 g, 16 mmol), $K_2CO_3$ (2.2 g, 16 mmol), KI (200 mg), 4-(3-chloropropoxy)indole (3.0 g, 14 mmol) and $CH_3CN$ (100 ml) was stirred at reflux under $N_2$ for 7 hours and then at ambient temperature for 68 hours. Reflux was resumed for an additional 6 hours whereupon a TLC revealed incomplete reaction. $K_2CO_3$ (0.5 g, 4 mmol) was added and the reaction was stirred at reflux for 17 hours. The cooled reaction was poured into $H_2O$ and the aqueous mixture was extracted with EtOAc. The organic extract was washed with $H_2O$ and saturated NaCl and after drying over $MgSO_4$ the solvent was removed to afford 5.7 g of a beige solid. The product was purified by preparative HPLC (Water's Associates Prep LC/System 500 using 2 silica gel columns and 4% MeOH—$CH_2Cl_2$ as eluent) to yield 3.4 g (61%) of a beige solid. Two consecutive recrystallizations from EtOH provided 2.3 g (41%) of a white powder, m.p.=129°–131° C.

ANALYSIS

Calculated for $C_{23}H_{24}FN_3O_2$: 70.21% C 6.15% H 10.68% N.

Found: 69.90% C 6.15% H 10.65% N.

EXAMPLE 143

6-Fluoro-3-[1-[3-[(6-methoxy-1H-indol-5-yl)oxy]propyl]-4-piperidinyl]-1,2-benzisoxazole hemifumarate A mixture of 6-fluoro-3-(4-piperidinyl)-1,2-benzisoxazole (3.0 g, 14 mmol), 5-(3-chloropropoxy)-6-methoxyindole (3.0 g, 13 mmol), $K_2CO_3$ (2.1 g, 14 mmol), KI (200 mg) and $CH_3CN$ (150 ml) was stirred at reflux under $N_2$ for 48 hours. The cooled reaction was poured into $H_2O$ and the aqueous mixture was extracted with EtOAc. The EtOAc extract was washed with $H_2O$ and brine and was dried with $MgSO_4$. Removal of the solvent in vacuo gave 5.6 g of a dark oil. The oil was purified by preparative HPLC (Water's Associates Prep LC/System 500 using 2 silica gel columns and 2% $Et_2NH$-EtOAc as eluent) to yield 2.5 g (47%) of a beige solid. Recrystallization from EtOH afforded 2.0 g of an off White powder. A 1.8 g (4 mmol) sample was dissolved in warm EtOAc and fumaric acid (0.5 g, 4 mmol) was added. The reaction was stirred at ca 40° C.

for 30 minutes and was then allowed to gradually cool to ambient temperature. The resultant hemifumarate salt was collected and dried to yield 2.0 g. The product was recrystallized from EtOH to provide 1.5 g (25%) of a light being powder m.p.=186°–188° C.

ANALYSIS

Calculated for $C_{26}H_{28}FN_3O_5$: 64.84% C 5.87% H 8.73% N

Found: 64.22% C 5.85% H 8.55% N.

EXAMPLE 144

1-[4-[3-[4-(6-Fluoro-1,2-benzisothiazol-3-yl)-1-piperidinyl]propoxy]-3-hydroxyphenyl]ethanone A mixture of 6-fluoro-3-(4-piperidinyl)-1,2-benzisothiazole (2.4 g, 10.1 mmol), 1-[4-(3-chloropropoxy)-3-hydroxyphenyl]ethanone (2.5 g, 11.1 mmol), $NaHCO_3$ (0.94 g, 11.1 mmol), KI (100 mg) and $CH_3CN$ (100 ml) was stirred at reflux under $N_2$ for 65 hours. The cooled reaction was poured into $H_2O$ and the aqueous mixture was extracted with EtoAc. The EtoAc extract was washed with $H_2O$ (1×) and brine (3×) and after drying with $MgSO_4$ the solvent was evaporated to give 4.2 g of a dark solid. Three consecutive recrystallizations from EtOH provided 2.1 g (48%) of glittery beige crystals m.p.=135°–137° C.

ANALYSIS

Calculated for $C_{23}H_{25}FN_2O_3S$: 64.47% C 5.88% H 6.54% N.

Found: 64.44% C 5.69% H 6.29% N.

EXAMPLE 145

4-[3-[4-(6-Fluoro-1,2-benzisothiazol-3-yl)-1-piperidinyl]propoxy]-3-methoxy-alpha-methylbenzenemethanol To a stirred solution of 1-[4-[3-[4-(6-fluoro-1,2-benzisothiazol-3-yl)-1-piperidinyl]propoxy]3-methoxyphenyl]ethanone (4.1 g, 9.3 mmol), in 60 ml MeOH-THF (1:1) under $N_2$ at ambient temperature, $NaBH_4$ (0.386 g, 10.2 mmol) was added portionwise. After complete addition, the reaction was stirred for 3.5 hours and was concentrated to yield a white gum. This was triturated with $H_2O$ (2×) and the aqueous fraction was decanted away. Residual water was removed under high vacuum to afford 5.0 g of a white powder. The compound was taken up in boiling toluene and the insolubles were filtered away. Concentration of the toluene filtrate afforded 3.8 g of a beige solid. Purification via preparative HPLC (Water's Associates prep LC/System 500, using 2 silica gel columns and 2% $Et_2NH$-EtoAc) provided 2.7 g of a light beige solid. The product was recrystallized from EtoAc to afford 1.7 g (42%) of a pure white powder, m.p.=113°–115° C.

ANALYSIS

Calculated for $C_{24}H_{29}FN_2O_3S$: 64.84% C 6.58% H 6.30% N.

Found: 64.85% C 6.44% H 6.19% N.

EXAMPLE 146

(R)-(−)-3-[4-(6-Fluoro-1,2-benzisoxazol-3-yl)-1-piperidinyl]-2-methyl-1-propyl acetate fumarate To a mixture of (R)-(−)-3-[4-(6-fluoro-1,2-benzisoxazol-3-yl)-1-piperidinyl]-2-methyl-1-propanol (3.2 gm, 11 mmoles), triethylamine (3.2 gm, 11 mmoles) in DCM (100 ml), acetyl chloride (890 mg, 11.3 mmoles) was added dropwise at 0° C. The mixture was stirred at room temperature for 4½ hrs. The solvent was removed on a rotary evaporator. The triethylamine HCl salt was filtered off using a small amount of DCM. The crude product was dissolved in DCM was purified by flash chromatography over a silica gel column ($SiO_2$, 30 gm; eluted with DCM and 1% $CH_3OH$ in DCM). The oil, thus purified, weighed 2.11 gm (58%). This oil was treated with a solution of fumaric acid (695mg, 1.0 eq.) in ethanol give the fumarate salt. Recrystallization from ethanol and isopropyl ether again yielded white crystals, 2.09 gm, m.p.=118°–120° C.

ANALYSIS

Calculated for $C_{18}H_{23}FN_2O_3.C_4H_4O_4$: 58.66% C 6.04% H 6.22% N.

Found: 58.53% C 5.76% H 8.91% N.

EXAMPLE 147

1-(R)-(−)-[4-[3-(6-Fluoro-1,2-benzisoxazol-3-yl)-1-piperidinyl]-2-methyl-1-propoxy]-3-methoxyphenyl] ethanone fumarate (A) (R)-(−)-3-[4-(6-fluoro-1,2-benzisoxazol-3-yl)-1-piperidinyl]-2-methyl-1-propyl methanesulfonate To a mixture of (R)-(−)-3-[4-(6-fluoro-1,2-benzisoxazol-3-yl)-1-piperidinyl]-2-methyl-1-propanol (7.26 gm, 24.8 mmoles), triethylamine (3ml, 30 mmoles) in methylene chloride (DCM, 120 ml), methanesulfonyl chloride (3.13 gm, 27.3 moles) was added dropwise at 0° C. The mixture was stirred at room temperature for 1 hr., then concentrated down to a crude mixture. Triethylamine hydrochloride salt was removed by filtration with DCM/ether as solvent. The crude oily mixture was purified with a flash chromatography column ($SiO_2$, 90 gm; eluted with DCM). The colorless oil, which is the methanesulfonate ester, weighed 6.48 gm (70%), and was used directly in the following step.

(B) 1(R)-(−)-[4-[3-[4-(6-fluoro-1,2-benzisoxazol-3-yl)-1-piperidinyl]-2methyl-propoxy]-3-ethoxyphenyl]ethanone fumarate A solution of the above methanesulfonate (6.48 gm, 175 mmoles) in DMF (5 ml) was added in one portion to an aged (½ hr) cold mixture of acetovanillone (4.13 gm, 24.9 moles) and sodium hydride (670 mg, 26.5 moles) in DMF (40 ml) at 0° C. The resulting mixture was warmed to ~50° C. briefly and stirred at room temperature for 16 hrs. The mixture was extracted into DCM (500 ml) and washed twice with water, then brine. The organic solution was dried over $MgSO_4$ and concentrated to an oil. This crude mixture was purified twice by flash chromatography over a silica gel column. The material thus purified weighed 5.37 gm. The fumarate salt was prepared by treatment of purified oil with fumaric acid (1.0 eq.) in ethanol and ether. Slightly off-white crystals were collected: 3.76 gm (38%), m.p.=141°–142° C.

ANALYSIS

Calculated for $C_{25}H_{29}FN_2O_4.C_4H_4O_4$ 62.58% C 5.98% H 5.03% N.

Found: 62.52% C 5.75% H 4.96% N.

EXAMPLE 148

3-[4-(6-Fluoro-1,2-benzisoxazol-3-yl)-1-piperidinyl]-2,2-dimethyl-1-propanol fumarate A mixture of 4-(6-fluoro-1,2-benzisoxazol-3-yl) piperidine (3.0 gm, 13.6 mmoles), $K_2CO_3$ (12.5 gm, 17.5 mmoles), 3-bromo-2,2-dimethyl-1-propanol (3 gm, 21 mmoles, 1.5 eq.), tetrabutylammonium hydrogen sulfate (1 gm, phase transfer catalyst) in water (5 ml) and acetonitrile (150 ml) was heated at reflux for 43 days. TLC showed a small spot for the expected product. The mixture was diluted with EtOAc (400 ml) and washed with brine. The organic solution was dried and concentrated to a dark brown mixture. The crude mixture was purified carefully by flash chromatography ($SiO_2$, 95 gm to afford the dried pure product; 260 mg, (6%) as an oil. This oil was converted to the fumarate salt by treatment with fumaric acid (98.5 mg, 1.0 eq.) in ethanol. Recrystallization from ethanol:ether yielded 210 mg of white crystals, m.p.=144°–145° C.

ANALYSIS

Calculated for $C_{17}H_{23}FN_2O_2.C_4H_4O_4$: 59.70% C 6.44% H 6.63% N.

Found: 59.52% C 6.38% H 6.52% N.

EXAMPLE 149

1-(S)-(+)1[4-[3-[4-(6-Fluoro-1,2-benzisoxazol-3-yl)-1-piperidinyl]-2-methyl-1-propoxy]-3-methoxyphenyl]ethanone fumarate (A) (S)-(+)-3-[4-(6-fluoro-1,2-benzisoxazol-3-yl)-1-piperidinyl]-2-methyl-1-propyl methanesulfonate To a mixture of (S)-(+)-3-[4-(6-fluoro-1,2-benzisoxazol-3-yl)-1-piperidinyl]-2-methyl-1-propanol (8.8 gm, 30 mmoles), triethylamine (3.2 gm, 32 mmoles) in dichloromethane (DCM, 150 ml), methanesulfonyl chloride (4 gm, 35 mmoles) was added dropwise at 0° C. over 10 minutes. The mixture was stirred at room temperature for 1 hr, then concentrated. Triethylamine HCl salt was filtered off with a little DCM as solvent. The crude oil was purified with a flash chromatography column ($SiO_2$, 90 gm; eluted with DCM). The colorless oil thus purified weighed 5.28 in (47%) was used immediately in the following step.

(B) 1-(S)-(+)-[4-[3-[4-(6-fluoro-1,2-benzisoxazol-3-yl)-1-piperidinyl]-2-methyl-proproxy]-3-methoxyphenyl]ethanone fumarate A solution of (S)-(+)-3-[4-(6-fluoro-1,2-benzisoxazol-3-yl-1-piperidinyl]-2-methyl-1-propyl methanesulfonate (5.28 gm, 14.27 mmoles) in dimethylformamide (DMF, 10 ml) was added in one portion to an aged (1 hr) cold mixture of acetovanillone (3.55 in, 33.1 mmoles) and sodium hydride (530 mg, 22 moles) in DMF (35 ml) at 0° C. under $N_2$. The reaction was stirred overnight (1.6 hrs.) at room temperature. The mixture was diluted with EtOAc and washed with $H_2O$ (2 times) and brine. The organic solution was dried and concentrated to an oil (9.4 gm). The crude oil mixture was purified by flash chromatography ($SiO_2$, 60 gm). The oil thus purified weighed 4.3 gm, (68%) and was converted to the fumarate salt (fumaric acid, 1.13 gm) in ethanol. Recrystallization from ethanol gave 1.36 gm of white crystals, m.p.=163°–165° C.

ANALYSIS

Calculated for $C_{25}H_{29}FN_2.O_4C_4H_4O_4$ 62.58% C 5.98% H 5.03% N.

Found: 62.40% C 5.84% H 4.92% N.

EXAMPLE 150

2-[4-(6-Fluoro-1,2-benzisoxazol-3-yl)-1-piperidinyl] ethyl thioacetate fumarate

To a stirred solution of 0° C. of triphenylphosphine (13.3 g, 0.05 mol) in THF (150 ml), diisopropylazodicarboxylate (10.2 ml, 0.05 mol) was added dropwise. After stirring at 0° C. for 0.5 h, a solution of 6-fluoro-3-[1-(2-hydroxyethyl)-4-piperidinyl]-1,2-benzisoxazole (8.5 g, 0.032 mol) and thioacetic acid (10.2 ml, 0.14 mol) in DMF (35 ml) was added dropwise. The reaction was then stirred at ambient temperature for 16 h, and then it was concentrated at 60° C., under vacuum, to yield a red oil. The oil was tritrated with $H_2O$, and then it was flash chromatographed on silica gel, eluting first with $CH_2Cl_2$ and then with 10% MeOH-CH—$_2Cl_2$. The appropriate fractions were concentrated to yield 16.5 g of an oil. The oil was tritrated with $Et_2O$ and the solid (reaction by-products) that formed was removed by filtration. The filtrate was treated with fumaric acid (4.3 g), and 7.2 g of the fumarate salt of the desired product was obtained as an off white solid. The salt was recrystallized from EtOAc and then twice from EtOH to afford 1.0 g (7.0%) of the thioacetate as an off white solid, m.p.=118°–120° C.

EXAMPLE 151

N-[2-[4-(6-Fluoro-1,2-benzisoxazol-3-yl)-1-piperidinyl]ethyl]-4,5-dichlorophthalimide A mixture of 2-[4-(6-fluoro-1,2-benzisoxazol-3-yl)-1-piperidinyl]ethylamine (2.83 gm, 10.7 mmol) and 4,5-dichlorophthalic anhydride (2.56 gm, 11.93 mmol, 1.1 eq) in methylene chloride (100 ml, DCM) was stirred for 2 h, white solids precipitated and the TLC showed disappearance of the starting material. The solvent was removed, and the crude solid was loaded onto a flash chromatography column (28 gm, $SiO_2$, sorbsil C-30, eluted with 1% MeOH in DCM; 0.5% of $NH_4OH$ was added towards the end of elution). The material thus purified weighed 2.26 gm as white crystals. Recrystallization twice from a large volume of hot ethanol (400 ml) yielded 1.57 gm of white shining crystals, m.p.=132°–134° C.

ANALYSIS

Calculated for $C_{22}H_{18}Cl_2FN_3O_3$: 57.16% C 3.92% H 9.09% N.

Found: 57.13% C 3.63% H 8.93% N.

EXAMPLE 152

N-[2-[4-(6-Fluoro-1,2-benzisothiazol-3-yl)-1-piperidinyl]ethyl]phthalimide

A stirred mixture of 6-fluoro-3-(4-piperidinyl)-1,2-benzisothiazole (4.72 g, 0.02 mole), potassium carbonate (4.14 g, 0.03 mole) and N-(2-bromoethyl)phthalimide (6.35 g, 0.0025 mole) in 200 ml of acetonitrile is heated at reflux for 4 hours. The solids are then removed by filtration and the filtrate is concentrated under reduced pressure. The residue is purified by chromatography over silica gel to provide N-[2-[4-(6-fluoro-1,2-benzisothiazol-3-yl)-1-piperidinyl] ethyl]phthalimide.

EXAMPLE 153

N-[2-[4-(6-Fluoro-1,2-benzisoxazol-3-yl)-1-piperidinyl]ethyl]-3,6-dichlorophthalimide A mixture of 2-[4-(6-fluoro-1,2-benzisoxazol-3-yl)-1-piperidinyl]ethylamine (2.44 gm, 9.24 mmoles) and 3,6-dichlorophthalic anhydride (2.01 gm; 9.27 mmoles) in dichloromethane (DCM, 50 ml) was stirred at room temperature for 1 hr. White precipitates formed and the TLC of the reaction mixture showed that there was no starting amine remaining. The solvent was stripped down and the white solids which were poorly soluble in DCM were loaded onto a flash chromatography column, ($SiO_2$; 30 gm) and the column was eluted with a solution of 1% $CH_3OH$ in DCM.

The desired product thus obtained weighed 2.29 gm (54%). Recrystallization from hot ethanol yielded 2.15 gm of white crystals, m.p.=163°–164° C.

ANALYSIS

Calculated for $C_{22}H_{18}Cl_2FN_3O_3$: 57.16% C 3.92% H 9.09% N.

Found: 57.16% C 3.64% H 9.13% N.

EXAMPLE 154

N-[2-[4-(6-Fluoro-1,2-benzisoxazol-3-yl)-1-piperidinyl]ethyl]-4-chlorophthalimide A stirred mixture of 2-[4-(6-fluoro-1,2-benzisoxazol-3-yl)-1-piperidinyl]ethylamine (2.63 g, 0.01 mole) and 4-chlorophthalic anhydride (1.82 g, 0.01 mole) in dichloromethane (100 ml) is stirred at room temperature for 3 hours. The solvent is removed under reduced pressure and the residual material is purified by flash chromatography. The product was purified further by recrystallization to give N-[2-[4-(6-fluoro-1,2-benzisoxazol-3-yl)-1-piperidinyl]ethyl]-4-chlorophthalimide.

EXAMPLE 155

N-[2-[4-(6-Fluoro-1,2-benzisoxazol-3-yl)-1-piperidinyl]ethyl]-3-fluorophthalimide A mixture of 2-[4-(6-fluoro-1,2-benzisoxazol-3-yl)-1-piperidinyl]ethylamine (2.37 gm, 8.98 mmoles), 3-fluorophthalic acid (1.82 in, 9.9 moles) and dicyclohexylcarbodiimide (DCC, 5.5 gm, 26.7 mmoles, 2.6 eq) in dichloromethane (DCM, 250 ml) was stirred at room temperature for 18 hrs. The solids were filtered off. The organic solution was concentrated down. The residue was purified on a flash chromatography column ($SiO_2$, 50 in; eluted with 1% $CH_3OH$:99% DCM, 1.4 liter; 2–6% $CH_3OH$:DCM, liter). The desired product thus obtained weighed 2.64 gm (71%) as an off-white solid. Recrystallization from hot ethanol gave 1.41 gm of white crystals, m.p.=142°–143° C.

ANALYSIS

Calculated for $C_{22}H_{19}F_2N_3O_3$: 64.22% C 4.66% H 10.21% N.

Found: 64.11% C 4.70% H 10.14% N.

EXAMPLE 156

N-[2-[4-(6-Fluoro-1,2-benzisoxazol-3-yl)-1-piperidinyl]ethyl]-4-fluorophthalimide A stirred mixture of 2-[4-(6-fluoro-1,2-benzisoxazol-3-yl)-1-piperidinyl]ethylamine (2.63 g, 0.01 mole) and 4-fluorophthalic anhydride (1.83 g, 0.011 mole) in dichloromethane (100 ml) is stirred at room temperature for 4 hours. The solvent is then removed under reduced pressure and the residual solids are purified by flash chromatography. The product is further purified by recrystallization to afford N-[2-[4-(6-fluoro-1,2-benzisoxazol-3-yl)-1-piperidinyl]ethyl]-4-fluorophthalimide.

EXAMPLE 157

N-[2-[4-(6-Fluoro-1,2-benzisoxazol-3-yl)-1-piperidinyl]ethyl]-4-methylphthalimide A mixture of 2-[4-(6-fluoro-1,2-benzisoxazol-3-yl)-1-piperidinyl]ethylamine (2.44 gm, 9.24 mmoles), 4-methylphthalic anhydride (1.76 gm, 10.8 moles) and dicyclohexylcarbodiimide (2.1 gm, 1.0 moles) in dichloromethane (DCM, 100 ml) was stirred at room temperature for 2 hr. The insolubles were filtered off. The DCM solution was concentrated to a crude solid. This was purified on a flash chromatography column (35 gm, SiO2, Sorbsil-C-30; eluted with 1% $CH_3OH$ in 99% DCM). The material thus purified weighed 1.0 gm (26%) as a white solid. Recrystallization from hot ethanol gave 665 mg of crystals, m.p.=138°–140° C.

ANALYSIS

Calculated for $C_{23}H_{22}FN_3O_3$: 67.80% C 5.44% H 10.31% N.

Found: 67.67% C 5.48% H 10.30% N.

EXAMPLE 158

N-[2-[4-(6-Fluoro-1,2-benzisoxazol-3-yl)-1-piperidinyl]ethyl]-4-methoxyphthalimide A stirred mixture of 2-[4-(6-fluoro-1,2-benzisoxazol-3-yl)-1-piperidinyl]ethylamine (2.63 g, 0.01 mole) and 4-methoxyphthalic anhydride (1.78 g, 0.01 mole) in dichloromethane (100 ml) is stirred at room temperature for 3 hours. The solvent is then removed under reduced pressure and the residual material is purified by flash chromatography. The product is purified further by recrystallization to give N-[2-[4-(6-fluoro-1,2-benzisoxazol-3yl)-1-piperidinyl]ethyl]-4-methoxyphthalimide.

EXAMPLE 159

N-[2-[4-(6-Fluoro-1,2-benzisoxazol-3-yl)-1-piperidinyl]ethyl]-4-nitrophthalimide A stirred mixture of 2-[4-(6-fluoro-1,2-benzisoxazol-3-yl)-1-piperidinyl]ethylamine (2.63 g, 0.01 mole) and 4-nitrophthalic anhydride (1.93 g, 0.01 mole) in dichloromethane (200 ml) is stirred at room temperature for 3 hours. The solvent is then removed under reduced pressure and the residual material is purified by flash chromatography. The product is purified further by recrystallization to give N-[2-[4-(6-fluoro-1,2-benzisoxazol-3-yl)-1-piperidinyl]ethyl]-4-nitrophthalimide.

EXAMPLE 160

4-[4-(6-Fluoro-1,2-benzisoxazol-3-yl)-1-piperidinyl]-2-methyl-2-hydroxybutane fumarate To a solution of ethyl 3-[4-(6-fluoro-1,2-benzisoxazol-3-yl)-1-piperidinyl]propionate (3.21 gm, 10 mmoles) in tetrahydrofuran (THF, 100 ml), methylmagnesium bromide (10 ml, 30 moles, 3M solution in ether) was added dropwise over 15 minutes at room temperature under $N_2$. The resulting mixture was stirred for 16 hours. The mixture was slowly hydrolyzed with aqueous $NH_4Cl$ solution. The THF solution was diluted with EtOAc (300 ml), then was washed with water and brine. The organic solution was separated and dried over $MgSO_4$. After removal of solvent, the crude product was purified by flash chromatography (25 gm, $SiO_2$; eluted with 1% $CH_3OH$:99% DCM). The material thus purified weighed 2.36 gm (77%) as white crystals. This was converted to the fumerate salt by treatment with fumaric acid (895 mg) in ethanol. Recrystallization from ethanol yielded with crystals, 2.47 gm, m.p.=156°–158° C.

ANALYSIS

Calculated for $C_{17}H_{23}FN_2O_2.C_4H_4O_4$: 59.70% C 6.44% H 5.63% N.

Found: 59.40% C 6.27% H 6.28% N.

EXAMPLE 161

Ethyl 3-[4-(6-fluoro-1,2-benzisoxazol-3-yl)-1-piperidinyl]propionate fumarate

A mixture of 4-(6-fluoro-1,2-benzisoxaxol-3-yl) piperidine (5 gm, 22.7 mmoles), $K_2CO_3$ (3.8 gm, 27.5 mmoles) and ethyl bromopropionate (5 gm, 27.6 mmoles, 1.2 eq) in acetonitrile (200 ml) was heated at reflux for 16 hours. The mixture was cooled and filtered. The solvent was removed, and the residue was purified on a flash chromatography column (60 gm, $SiO_2$, eluted with DCM). The material thus purified weighed 7.27 gum (83%). The fumarate salt was prepared by treatment of the free base (2.17 gm) with fumaric acid (820 mg, 1.0 eq) in ethanol. Recrystallization from ethanol yielded 2.49 gm of white crystals, m.p.=135°–136° C.

ANALYSIS

Calculated for $C_{17}H_{21}FN_2O_3.C_4H_4O_4$: 57.79% C 5.77% H 6.42% N.

Founded: 57.86% C 5.67% H 6.30% N.

This invention thus provides a group of chemical compounds that are capable of producing antipsychotic effects and may be capable of affecting negative symptoms of schizophrenia in a beneficial manner. In addition, many of the compounds may also have reduced tendencies to produce extrapyramidal side effects in mammals.

What is claimed is:

1. A compound of the formula:

[

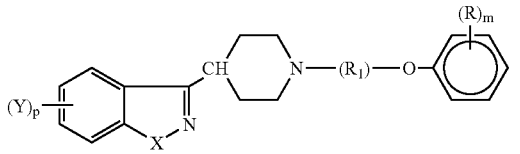

]

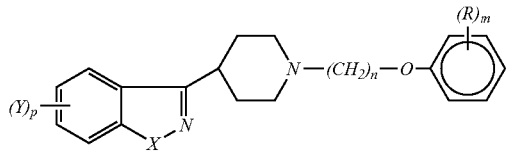

wherein

X is —O— or —S—;

p is 1 or 2;

Y is hydrogen, lower alkyl, hydroxy, chlorine, fluorine, bromine, iodine, lower alkoxy, trifluoromethyl, nitro, or amino, when p is 1;

Y is lower alkoxy[, hydroxy and halogen] when p is 2 and X is —O—;

[$(R_1)$ is $R_{20}$, $R_{21}$, or $R_{22}$, wherein:

$R_{20}$ is $—(CH_2)_n—$ where] n is 2, 3, 4 or 5;

[$R_{21}$ is $—CH_2—CH═CH—CH_2—$, $—CH_2—C≡C—CH_2—$, $—CH_2—CH═CH—CH_2—CH_2$, $—CH_2—CH_2—CH═CH—CH_2—$, $—CH_2—C≡C—CH_2—CH_2—$, or $—CH_2—CH_2—C≡C—CH_2—$, the —CH═CH— bond being cis or trans;

$R_{22}$ is $R_{20}$ or $R_{21}$ in which one or more carbon atoms of $R_{20}$ or $R_{21}$ are substituted by at least one $C_1$–$C_6$ linear alkyl group, pheny group or

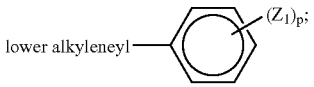

where $Z_1$ is lower alkyl, —OH, lower alkoxy, $—CF_3$, $—NO_2$, $—NH_2$ or halogen;]

R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, [monoalkylaminocarbonyl, dialkylaminocarbonyl, formyl,] —C(═O)-alkyl, —C(═O)—O-alkyl, —C(═O)-aryl, —C(═O)-heteroaryl, [—CH($OR^7$)-alkyl, —C(═W)-alkyl, —C(═W)-aryl, and —C(═W)-heteroaryl;] *or* —*CH*($OR_7$)-*alkyl;*

*wherein* alkyl is lower alkyl;

aryl is phenyl or

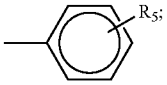

where*in* $R_5$ is hydrogen, lower alkyl, lower alkoxy, hydroxy, chlorine, fluorine, bromine, iodine, lower monoalkylamino, [lower dialkylamino,] nitro, cyano, trifluoromethyl, *or* trifluoromethoxy;

heteroaryl is

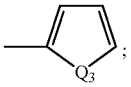

*wherein* $Q_3$ is —O—, —S—, —NH—, *or* —CH═N—;

[W is $CH_2$ or $CHR_8$ or $N—R_9$;]

$R_7$ is hydrogen, lower alkyl, or acyl;

[$R_8$ is lower alkyl;

$R_9$ is hydroxy, lower alkoxy, or $—NHR_{10}$; and $R_{10}$ is hydrogen, lower alkyl, $C_1$–$C_3$ acyl, aryl, —C(═)-aryl or —C(═O)-heteroaryl, where aryl and heteroaryl are as defined above;] and m is 1, 2, or 3;

[all geometric, optical and stereoisomers thereof,] or a pharmaceutically acceptable acid addition salt thereof.

2. A compound as claimed in claim 1, which is 1-[4-[3-[4-(1,2-benzisoxazol-3-yl)-1-piperidinyl]propoxy]-3-methoxyphenyl]ethanone or a pharmaceutically acceptable acid addition salt thereof.

3. A compound as claimed in claim 1, which is 1-[4-[3-[4-(6-fluoro-1,2-benzisoxazol-3-yl)-1-piperidinyl]-propoxy]-3-methoxyphenyl]ethanone or a pharmaceutically acceptable acid addition salt thereof.

4. A compound as claimed in claim 1, which is 1-[4-[4-[4-(1,2-benzisoxazol-3-yl)-1-piperidinyl]butoxy]-3-methoxyphenyl]ethanone or a pharmaceutically acceptable acid addition salt thereof.

5. A compound as claimed in claim 1, which is 1-[4-[4-[4-(6-fluoro-1,2-benzisoxazol-3-yl)-1-piperidinyl]butoxy]-3-methoxyphenyl]ethanone or a pharmaceutically acceptable acid addition salt thereof.

6. A compound as claimed in claim 1, which is 1-[4-[2-[4-(1,2-benzisoxazol-3-yl)-1-piperidinyl]ethoxy]-3-methoxyphenyl]ethanone or a pharmaceutically acceptable acid addition salt thereof.

7. A compound as claimed in claim 1, which is 1-[4-[2-[4-(6-fluoro-1,2-benzisoxazol-3-yl)-1-piperidinyl]ethoxy-3-methoxyphenyl]ethanone or a pharmaceutically acceptable acid addition salt thereof.

8. A compound as claimed in claim 1, which is 1-[4-[3-[4-(1,2-benzisothiazol-3-yl)-1-piperidinyl]propoxy]-3-methoxyphenyl]ethanone or a pharmaceutically acceptable acid addition salt thereof.

9. A compound as claimed in claim 1, which is 4-[3-[4-(6-fluoro-1,2-benzisoxazol-3-yl)-1-piperidinyl]propoxy]-3-methoxy-α-methylbenzenemethanol or a pharmaceutically acceptable acid addition salt thereof.

10. A compound as claimed in claim 1, which is 1-[4-[3-[4-(6-fluoro-1,2-benzisoxazol-3-yl)-1-piperidinyl]-propoxy]-3-hydroxyphenyl]ethanone or a pharmaceutically acceptable acid addition salt thereof.

11. A compound as claimed in claim 1, which is 1-[4-[3-[4-(6-chloro-1,2-benzisoxazol-3-yl)-1-piperidinyl]-propoxy]-3-methoxyphenyl]ethanone or a pharmaceutically acceptable acid addition salt thereof.

12. A compound as claimed as claim 1, which is 1-[4-[4-[4-(6-chloro-1,2-benzisoxazol-3-yl)-1-piperindyl]-butoxy]-3-methoxyphenyl]ethanone or a pharmaceutically acceptable acid addition salt thereof.

13. A compound as claimed in claim 1, which is 1-[4-[3-[4-(5-fluoro-1,2-benzisoxazol-3-yl)-1-piperidinyl]-propoxy]-3-methoxyphenyl]ethanone or a pharmaceutically acceptable acid addition salt thereof.

14. A compound as claimed in claim 1, which is 6-fluoro-3-[1-[1-[3-(2-methoxyphenoxy)propyl]-4-piperidinyl]-1,2-benzisoxazole or a pharmaceutically acceptable acid salt thereof.

15. A compound as claimed in claim 1, which is 1-[3-[3-[4-(6-fluoro-1,2-benzisoxazol-3-yl)-1-piperidinyl]-propoxy]-4-methoxyphenyl]phenylmethanone or a pharmaceutically acceptable acid addition salt thereof.

16. A compound as claimed in claim 1, which is 1-[4-[2-[4-(6-chloro-1,2-benzisoxazol-3-yl)-1-piperidinyl]ethoxy]-3-methoxyphenyl]ethanone or a pharmaceutically acceptable acid addition salt thereof.

17. A compound as claimed in claim 1, which is 1-[3-[3-[4-(6-fluoro-1,2-benzisoxzol-3-yl)-1-piperidinyl]-propoxy]phenyl]ethanone or a pharmaceutically acceptable acid addition salt thereof.

18. A compound as claimed in claim 1, which is 1-[4-[3-[4-(6-fluoro-1,2-benzisoxazol-3yl)-1-piperidinyl]-propoxyl]-2-methylphenyl]ethanone or a pharmaceutically acceptable acid addition salt thereof.

19. A compound as claimed in claim 1, which is 1-[2-[3-[4-(6-fluoro-1,2-benzisoxazol-3-yl)-1-piperidinyl]-propoxy]-5-methylphenyl]ethanone or a pharmaceutically acceptable acid addition salt thereof.

20. A compound as claimed in claim 1, which is N-[3-[3-[4-(6-fluoro-1,2-benzisoxazol-3-yl)-1-piperidinyl]-propoxy]-4-methoxyphenyl]acetamide or a pharmaceutically acceptable acid addition salt thereof.

21. A compound as claimed in claim 1, which is 1-(4-[3-[4-(6-fluoro-1,2-benzisoxazol-3-yl)-1-piperidinyl]-propoxy]-3-methylphenyl]ethanone or a pharmaceutically acceptable acid addition salt thereof.

22. A compound as claimed in claim 1, which is 1-[4-[3-[4-(6-fluoro-1,2-benzisoxazol-3-yl)-1-piperidinyl]-propoxy]phenyl]ethanone or a pharmaceutically acceptable acid addition salt thereof.

23. A compound as claimed in claim 1, which is 4-[3-[4-(6-fluoro-1,2-1,2-benzisoxazol-3-yl)-1-piperidinyl]-propoxy]-3-methoxybenzonitrile or a pharmaceutically acceptable acid addition salt thereof.

24. A compound as claimed in claim 1, which is 1-[3,5-dibromo-4-[3-[4-(6-fluoro-1,2-benzisoxazol-3-yl)-1-piperidinyl]propoxy]phenyl]ethanone or a pharmaceutically acceptable acid addition salt thereof.

25. A compound as claimed in claim 1, which is 6-fluoro-3-[1-(3-phenoxypropyl)-4-piperidinyl]-1,2-benzisoxazole or a pharmaceutically acceptable acid addition salt thereof.

26. A compound as claimed in claim 1, which is [1-[4-[3-[4-(6-fluoro-1,2-benzisoxazol-3-yl]-1-piperidinyl]-propoxy]-3-methylmercaptophenyl]ethanone] *1-[4-[3-[4-(6-fluoro-1,2-benzisoxazol-3-yl)-1-piperidinyl]propoxy]-3-methylmercaptophenyl]ethanone* or a pharmaceutically acceptable acid addition salt thereof.

27. A compound as claimed in claim 1, which is 1-[4-[4-[4-(1,2-benzisothiazol-3-yl)-1-piperidinyl]butoxy]-3-methoxyphenyl]ethanone or a pharmaceutically acceptable acid addition salt thereof.

28. A compound as claimed in claim 1, which is 1-[4-[3-[4-(6-fluoro-1,2-benzisoxazol-3-yl)-1-piperidinyl]-propoxy]-3-methoxyphenyl]phenylmethanone or a pharmaceutically acceptable acid addition salt thereof.

29. A compound as claimed in claim 1, which is 3-[1-[3-[4-ethoxyethyl)-2-methoxyphenoxy]propyl]-4-piperidinyl]-6-fluoro-1,2-benzisoxazole or a pharmaceutically acceptable acid addition salt thereof.

30. A compound as claimed in claim 1, which is 3-[1-[3-[4-(1-acetoxyethyl)-2-methoxyphenoxy]propyl]-4-piperidinyl]-6-fluoro-1,2-benzisoxazole or a pharmaceutically acceptable acid addition salt thereof.

31. A compound as claimed in claim 1, which is 1-[4-[3-[4-(6-fluoro-1,2-benzisoxazol-3-yl)-1-piperidinyl]-propoxy]-3-methoxyphenyl]pentanone or a pharmaceutically acceptable acid addition salt thereof.

32. A compound as claimed in claim 1, which is 2-[3-[4-(6-fluoro-1,2-benzisoxazol-3-yl)-1-piperidinyl]-propoxy]-N-methylbenzeneamine or a pharmaceutically acceptable acid addition salt thereof.

33. A compound as claimed in claim 1, which is 3-[1-[3-(4-bromo-2-methoxyphenoxy)propyl]-4-piperidinyl]-6-fluoro-1,2-benzisoxazole or a pharmaceutically acceptable acid addition salt thereof.

34. A compound as claimed in claim 1, which is 1-[4-[3-[4-(6-fluoro-1,2-benzisoxazol-3-yl)-1-piperidinyl]-propoxy]-3-methoxyphenyl]propanone or a pharmaceutically acceptable acid addition salt thereof.

35. A compound as claimed in claim 1, which is 4-[3-[4-(6-fluoro-1,2-benzisoxazol-3-yl)-1-piperidinyl]-propoxy]-3-methoxybenzamide or a pharmaceutically acceptable acid addition salt thereof.

36. A compound as claimed in claim 1, which is 1-[4-[3-[4-(6-fluoro-1,2-benzisoxazol-3-yl)-1-piperidinyl]-propoxy]-3-(methylamino)phenyl]ethanone or a pharmaceutically acceptable acid addition salt thereof.

37. A compound as claimed in claim 1, which is 1-[4-[3-[4-(6-fluoro-1,2-benzisoxazol-3-yl)-1-piperidinyl]-propoxy]-3-ethoxyphenyl]ethanone or a pharmaceutically acceptable acid addition salt thereof.

38. A compound as claimed in claim 1, which is N-[2-[3-[4-(6-fluoro-1,2-benzisoxazol-3-yl)-1-piperidinyl]-propoxy]phenyl]acetamide, or a pharmaceutically acceptable acid addition salt thereof.

39. A compound as claimed in claim 1, which is 1-[4-[3-[4-(6-fluoro-1,2-benzisoxazol-3-yl)-1-piperidinyl]-propoxy]-3-dimethylaminophenyl]ethanone, or a pharmaceutically acceptable acid addition salt thereof.

40. A compound as claimed in claim 1, which is 1-[4-[3-[4-(6-fluoro-1,2-benzisoxazol-3-yl)-1-piperidinyl]-propoxy]-2-methoxyphenyl]ethanone, or a pharmaceutically acceptable acid addition salt thereof.

41. A compound as claimed in claim 1, which is 4-[3-[4-(6-fluoro-1,2-benzisoxazol-3-yl)-1-piperidinyl]-propoxy]-3-hydroxy-α-methylbenzene methanol, or a pharmaceutically acceptable acid addition salt thereof.

42. A compound as claimed in claim 1, which is 2-[3-[4-(6-fluoro-1,2-benzisoxazol-3-yl)-1-piperidinyl]-propoxy]aniline, or a pharmaceutically acceptable acid addition salt thereof.

43. A compound as claimed in claim 1, which is N-[5-acetyl-2-[3-[4-(6-fluoro-1,2-benzisoxazol-3-yl)-1-piperidinyl]propoxy]phenyl]acetamide, or a pharmaceutically acceptable acid addition salt thereof.

44. A compound as claimed in claim 1, which is 3-[1-[3-(4-ethyl-2-methoxyphenoxy)propyl]-4-piperidinyl]-6-fluoro-1,2-benzisoxazole, or a pharmaceutically acceptable acid addition salt thereof.

45. A compound as claimed in claim 1, which is 1-[3,5-dimethoxy-4-[3-[4-(6-fluoro-1,2-benzisoxazol-3-yl)-1-piperidinyl]propoxy]phenyl]ethanone, or a pharmaceutically acceptable acid addition salt thereof.

46. A compound as claimed in claim 1, which is N-[3-[3-[4-(6-fluoro-1,2-benzisoxaxol-3-yl)-1-piperidinyl]-propoxy]phenyl]acetamide, or a pharmaceutically acceptable acid addition salt thereof.

47. A compound as claimed in claim 1, which is 3-[3-[4-(6-fluoro-1,2-benzisoxazol-3-yl)-1-piperidinyl]-propoxy] aniline, or a pharmaceutically acceptable acid addition salt thereof.

48. A compound as claimed in claim 1, which is 3-[3-[4-(6-fluoro-1,2-benzisoxazol-3-yl)-1-piperidinyl]-propoxy]-4-methoxyaniline, or a pharmaceutically acceptable acid addition salt thereof.

49. A compound as claimed in claim 1, which is 1-[4-[3-[4-(6-fluoro-1,2-benzisothiazol-3-yl)-1-piperidinyl]-propoxy]-3-methylaminophenyl]ethanone, or a pharmaceutically acceptable acid addition salt thereof.

50. A compound as claimed in claim 1, which is N-[3-[3-[4-(6-fluoro-1,2-benzisothiazol-3-yl)-1-piperidinyl]-propoxy]-4-methoxyphenyl]acetamide, or a pharmaceutically acceptable acid addition salt thereof.

51. A compound as claimed in claim 1, which is 1-[4-[3-[4-(6-fluoro-1,2-benzisothiazol-3-yl)-1-piperidinyl]-propoxy]-3-methoxyphenyl]ethanone, or a pharmaceutically acceptable acid addition salt thereof.

52. A compound as claimed in claim [1] *132*, which is N,N-dimethyl-4-[3-[4-(6-fluoro-1,2-benzisoxazol-3-yl)-1-piperidinyl]propoxy]-3-methoxybenzamide, or a pharmaceutically acceptable acid addition salt thereof.

53. A compound as claimed in claim [1] *132*, which is 1-[4-[3-[4(6-fluoro-1,2-benzisoxazol-3-yl)-1-piperidinyl]-propoxy]-3-(methylamino)phenyl]ethanone oxime, or a pharmaceutically acceptable acid addition salt thereof.

54. A compound as claimed in claim [1] *132*, which is 1-[4-[3-[4-(6-fluoro-1,2-benzisoxazol-3-yl)-1-piperidinyl]-propoxy]methoxyphenyl]ethanone oxime O-methyl ether, or a pharmaceutically acceptable acid addition salt thereof.

55. A compound as claimed in claim [1] *132*, which is 1-[4-[3-[4-(6-fluoro-1,2-benzisoxazol-3-yl)-1-piperidinyl]-propoxy]-3-methoxyphenyl]ethanone hydrazone, or a pharmaceutically acceptable acid addition salt thereof.

56. A compound as claimed in claim [1] *132*, which is 6-fluoro-3-[1-[3-[2-methoxy-4-(1-methylethenyl)phenoxy] propyl]-4-piperidinyl]-1,2-benzisoxazole, or a pharmaceutically acceptable acid addition salt thereof.

57. A compound as claimed in claim [1] *87*, which is (Z)-1-[4-[[4-[4-(6-fluoro-1,2-benzisoxazol-3-yl)-1-piperidinyl]-2butenyl]oxy]-3-methoxyphenyl]ethanone, or a pharmaceutically acceptable acid addition salt thereof.

58. A compound as claimed in claim [1] *87*, which is (E)-1-[3-[4-[[4-(6-fluoro-1,2-benzisoxazol-3-yl)-1-piperidinyl]-2-butenyl]oxy]-4-hydroxyphenyl]ethanone, or a pharmaceutically acceptable acid addition salt thereof.

59. A compound [as claimed in claim 1], which is (E)-1-[3-[4-[[4-(6-fluoro-1,2-benzisoxazol-3-yl)-1-piperidinyl]-2butenyl]oxy]-4-benzyloxyphenyl]ethanone, or a pharmaceutically acceptable acid addition salt thereof.

60. A compound as claimed in claim 1, which is 1-[4-[3-[4-(6-Fluoro-1,2-benzisoxazol-3-yl)-1-piperidinyl]-propoxy]-3-bromophenyl]ethanone or a pharmaceutically acceptable acid addition salt thereof.

61. A compound as claimed in claim 1, which is 1-[4-[3-[4-(6-fluoro-1,2-benzisoxazol-3-yl)-1-piperidinyl]-propoxy]-3-methoxyphenyl]-2,2,2-trifluoroethanone, or a pharmaceutically acceptable acid addition salt thereof.

62. A compound as claimed in claim 1, which is 3-[1-[3-[4-(1-methoxyethyl)-2-hydroxyphenoxyl]propyl]-4-piperidinyl]-6-fluoro-1,2-benzisoxazole, or a pharmaceutically acceptable acid addition salt thereof.

63. A compound as claimed in claim 1, which is 1-[4-[3-[4-(6-fluoro-1,2-benzisothazol-3-yl)-1-piperidinyl]-propoxy]-3-hydroxyphenyl]ethanone, or a pharmaceutically acceptable acid addition salt thereof.

64. A compound as claimed in claim 1, which is 4-[3-[4-(6-fluoro-1,2-benzisothiazol-3-yl)-1-piperidinyl]-propoxy]-3-methoxy-alpha-methylbenzenemethanol, or a pharmaceutically acceptable acid addition salt thereof.

65. A compound as claimed in claim [1, which is 1-(R)-(−)-[4-[3-(6-fluoro-1,2-benzisoxazol-3-yl)-1-piperidinyl]-2-methyl-1-propoxy]-3-methoxyphenyl]ethanone, or] *104, which is 1-(R)-(−)-[4-[3-[4-(6-fluoro-1,2-benzisoxazol-3-yl)-1-piperidinyl]-2-methyl-1-propoxy]-3-methoxyphenyl] ethanone, or* a pharmaceutically acceptable acid addition salt thereof.

66. A compound as claimed in claim [1] *104*, which is 1-(S)-(+)-[4-[3-[4-(6-fluoro-1,2-benzisoxazol-3-yl)-1-piperidinyl]-2-methyl-1-propoxy]-3-methoxyphenyl] ethanone, or a pharmaceutically acceptable acid addition salt thereof.

67. The compound of claim 1, wherein the pharmaceutically acceptable addition salt is selected from the group consisting of salts of mineral acids, salts of monobasic carboxylic acids, slats of dibasic carboxylic acids, and salts of tribasic carboxylic acids.

68. The compound of claim 67, wherein said pharmaceutically acceptable addition salts are selected from the group consisting of salts of hydrochloric acid, sulfuric acid, nitric acid, acetic acid, propionic acid, maleic acid, fumaric acid, carboxysuccinic acid, and citric acid.

69. The compound of claim 1, wherein Y is in the 5 position.

70. The compound of claim 1, wherein Y is in the 6 position.

71. The compound of claim 1, wherein Y is selected from the group consisting of hydrogen, chlorine, bromine and fluorine.

72. The compound of claim 71, wherein Y is fluorine.

73. The compound of claim 72, wherein Y is in the 6 position.

74. The compound of claim 1, wherein p is 2, X is —O—, and Y is [selected from the group consisting of] lower alkoxy[, hydroxy and halogen groups].

75. The compound of claim 74, wherein Y is a methoxy group.

[76. The compound of claim 1, wherein $R_1$ is —$CH_2$—CH═CH—$CH_2$—.]

77. The compound of claim 1, wherein R is selected from the group consisting of hydrogen, $C_1$–$C_3$ alkyl, $C_1$–$C_3$alkoxy, hydroxyl, —$COCF_3$, $C_1$–$C_6$alkanoyl, Cl, F, Br, I, $C_1$–$C_3$ alkylamino, [—$NO_3$,] —$NO_2$, —$CF_3$, —$OCF_3$, and —C(═O)-lower alkyl.

78. A compound of the formula:

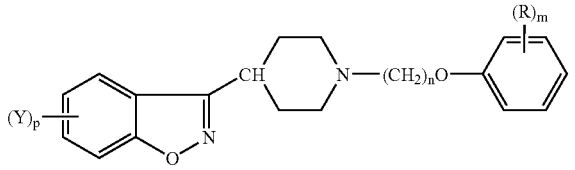

wherein p is 1 or 2;

Y is hydrogen, Cl, Br, or F, when p is 1;

Y is lower alkoxy, [hydroxy, or halogen] when p is 2;

n is 2, 3, or 4;

R is hydrogen, $C_1$–$C_3$ alkyl, $C_1$–$C_3$ alkoxy, hydroxyl, [alkanoyl,] Cl, F, Br, I, amino, $C_1$–$C_3$ mono or dialkyl amino, acylamino, —$NO_2$, —$OCF_3$, —$CF_3$, alkyl-C(═O)—, $CF_3$—C(═O)—, or —CH($OR_7$)-alkyl;

alkyl is lower alkyl $R_7$ is hydrogen, lower alkyl-C(═O)—, or $CF_3$—C(═O)—;

and m is 1, 2, or 3;

R is hydrogen, $C_1$–$C_3$ alkyl, $C_1$–$C_3$ alkoxy, hydroxyl, [alkanoyl,] Cl, F, Br, I, amino, $C_1$–$C_3$ mono or dialkyl amino, acylamino, —$NO_2$, —$OCF_3$, —$CF_3$, alkyl-C(═O)—, $CF_3$—C(═O)—, or —CH($OR_7$)-alkyl;

alkyl is lower alkyl;

$R_7$ is hydrogen, lower alkyl, lower alkyl-C(═O)—, or $CF_3$—C(═O)—;

and m is 1, 2, or 3;

all geometric, optical and stereoisomers thereof or a pharmaceutically acceptable acid addition salt thereof.

79. A compound of the formula:

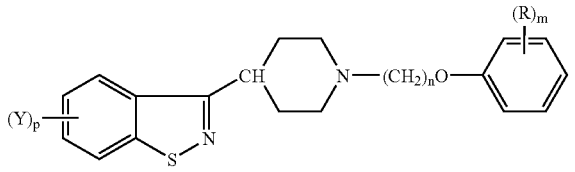

wherein p is 1 or 2;

Y is hydrogen, Cl, Br, or F, when p is 1;

Y is lower alkoxy, [hydroxy, or halogen] when p is 2;

n is 2, 3, or 4;

R is hydrogen, $C_1$–$C_3$ alkyl, $C_1$–$C_3$ alkoxy, hydroxyl, acyl, alkanoyl, Cl, F, Br, I, amino, $C_1$–$C_3$ mono or dialkyl amino, acylamino, —$NO_2$, —$OCF_3$, —$CF_3$, alkyl-C(═O)—, $CF_3$—C(═O)—, or —CH($OR_7$)-alkyl;

alkyl is lower alkyl;

$R_7$ is hydrogen lower alkyl, [or] lower alkyl-C(═O)—, *or* $CF_3$—C(═O)—;

and m is 1, 2, or 3;

all geometric, optical and stereoisomers thereof or a pharmaceutically acceptable acid addition salt thereof.

80. A compound [of the formula:

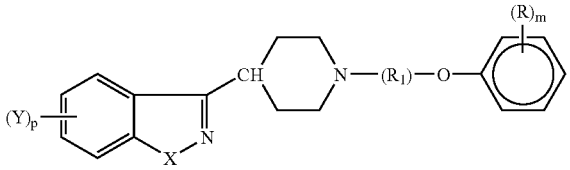

wherein

X is —O— or —S—;

p is 1 or 2;

Y is hydrogen, lower alkyl, hydroxy, chlorine, fluorine, bromine, iodine, lower alkoxy, trifluoromethyl, nitro, or amino, when p is 1;

Y is lower alkoxy, hydroxy and halogen when p is 2 and X is —O—, ($R_1$) is $R_{20}$, $R_{21}$, or $R_{22}$, wherein:

$R_{20}$ $R_{21}$ is

—$CH_2$ —CH═CH—$CH_2$—,

—$CH_2$—C≡C—$CH_2$—,

—$CH_2$—CH═CH—$CH_2$—$CH_2$ —,

—$CH_2$—$CH_2$—CH═CH—$CH_2$—,

—$CH_2$—CH≡C—$CH_2$—$CH_2$—, or

—$CH_2$—$CH_2$—C≡C—$CH_2$—, the —CH═CH— bond being cis or trans;

$R_{22}$ is $R_{20}$ is $R_{21}$ in which one or more carbon atoms of $R_{20}$ or $R_{21}$ are substituted by at least one $C_1$–$C_6$ linear alkyl group, phenyl group or

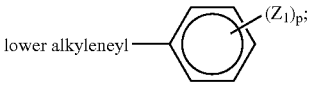

wherein $Z_1$ is lower alkyl, —OH, lower alkoxy, —$CF_3$, —$NO_2$, —$NH_2$ or halogen; and R and m are as defined hereinafter;

m is 1, 2, or 3; and when m is 1, 2, or 3, R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoalkylaminocarbonyl, dialkylaminocarbonyl, formyl, —C(═O)-alkyl, —C(═O)—O-alkyl, —C(═O)-aryl, —C(═O)-heteroaryl, —CH($OR^7$)-alkyl, —C(═W)-alkyl, —C(═W)-aryl, and —C(═W)-heteroaryl;

alkyl is lower alkyl;

aryl is phenyl or

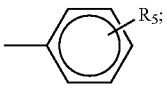

where $R_5$ is hydrogen, lower alkyl, lower alkoxy, hydroxy, chlorine, fluorine, bromine, iodine, lower monoalkylamino, lower dialkylamino, nitro, cyano, trifluoromethyl, trifluoromethoxy;

heteroaryl is

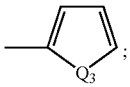

$Q_3$ is —O—, —S—, —NH—, —CH═N—;

W is $CH_2$ or $CHR_8$ or N—$R_9$;

$R_7$ is hydrogen, lower alkyl, or acyl;

$R_8$ is lower alkyl;

$R_9$ is hydroxy, lower alkoxy, or —$NHR_{10}$; and $R_{10}$ is hydrogen, lower alkyl, $C_1$–$C_3$ acyl, aryl, —C(═O)-aryl or —C(═O)-heteroaryl, where aryl and heteroaryl are as defined above; and] *as claimed in claim 1 with the proviso that* when m is 3, R is not —C(═O)-heteroaryl or —C(═W)-heteroaryl;

[all geometric, optical and stereoisomers thereof,] or *a* pharmaceutically acceptable acid addition salt thereof.

81. A compound as claimed in claim [1] *87*, which is (E)-1-[4-[[4-[4-(6-fluoro-1,2-benzisoxazol-3-yl)-1-piperidinyl]-2-butenyl]oxy]-3-methoxyphenyl]ethanone, or a pharmaceutically acceptable acid addition salt thereof.

82. A pharmaceutical composition, which comprises *a* compound as claimed in any one of claims [1–81] *1–75 and 77–81*, and a pharmaceutically acceptable carrier therefor.

83. An antipsychotic composition which comprises a compound as claimed in any one of claims [1–81] *1–75 and 77–81*, in an amount sufficient to produce an antipsychotic effect, and a pharmaceutically acceptable carrier therefor.

84. A method of treating psychoses, which comprises administering to a mammal a psychoses-treating effective amount of a compound as claimed in any one of claims [1–81] *1–75 and 77–81*.

85. An analgesic composition which comprises a compound as claimed in any one of claims [1–81] *1–75 and 77–81*, in an amount sufficient to produce a pain-relieving effect, and a pharmaceutically acceptable carrier therefor.

86. A method of alleviating pain, which comprises administering to a mammal a pain-relieving effective amount of a compound as claimed in any one of claims [1–81] *1–75 and 77–81*.

*87. A compound of the formula*

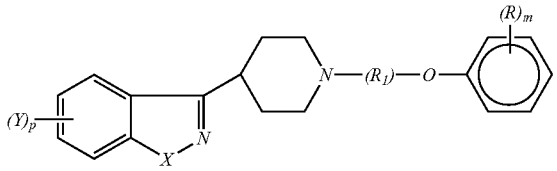

*wherein*

*X is —O— or —S—;*

*p is 1 or 2;*

*Y is hydrogen, lower alkyl, hydroxy, chlorine, fluorine, bromine, iodine, lower alkoxy, trifluoromethyl, nitro, or amino, when p is 1;*

*Y is lower alkoxy, hydroxy and halogen, when p is 2 and X is —O—;*

*($R_1$) is*

*—$CH_2$—CH═CH—$CH_2$—,*

*—$CH_2$—C≡C—$CH_2$—,*

*—$CH_2$—CH═CH—$CH_2$—$CH_2$—,*

*—$CH_2$—$CH_2$ —CH═CH—$CH_2$—,*

*—$CH_2$—C≡C—$CH_2$ —$CH_2$—, or*

*—$CH_2$—$CH_2$—C≡C—$CH_2$—,*

*the —CH═CH— bond being cis or trans;*

*R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, dialkylaminocarbonyl, formyl, —C(═O)-alkyl, —C(═O)—O-alkyl, —C(═O)-aryl, —C(═O)-heteroaryl, —CH($OR_7$)-alkyl, —C(═W)-alkyl, —C(═W)-aryl, or —C(═W)-heteroaryl;*

*wherein alkyl is lower alkyl;*

*aryl is phenyl or*

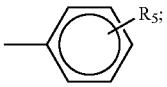

*wherein $R_3$ is hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;*

*heteroaryl is*

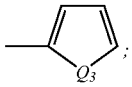

*wherein $Q_3$ is —O—, —S—, —NH—, or —CH═N—;*

*W is $CH_2$ or $CHR_8$ or N—$R_9$;*

*$R_7$ is hydrogen, lower alkyl, or acyl;*

*$R_8$ is lower alkyl;*

*$R_9$ is hydroxy, lower alkoxy, or —$NHR_{10}$; and*

*$R_{10}$ is hydrogen, lower alkyl, $C_1$–$C_3$ acyl aryl, —C(═O)-aryl, or —C(═O)-heteroaryl,*

*wherein aryl and heteroaryl are as defined above; and*

*m is 1, 2, or 3;*

*all geometric, optical and stereoisomers thereof, or a pharmaceutically acceptable acid addition salt thereof.*

*88. The compound of claim 87, wherein the pharmaceutically acceptable addition salt is selected from the group consisting of salts of minerals acids, salts of monobasic carboxylic acids, salts of dibasic carboxylic acids, and salts of tribasic carboxylic acids.*

*89. The compound of claim 88, wherein said pharmaceutically acceptable addition salts are selected from the group consisting of salts of hydrochloric acid, sulfuric acid, nitric acid acetic acid, propionic acid, maleic acid, fumaric acid, carboxysuccinic acid, and citric acid.*

*90. The compound of claim 87, wherein Y is in the 5 position.*

*91. The compound of claim 87, wherein Y is in the 6 position.*

*92. The compound of claim 87, wherein Y is selected from the group consisting of hydrogen, chlorine, bromine and fluorine.*

*93. The compound of claim 92, wherein Y is fluorine.*

*94. The compound of claim 93, wherein Y is in the 6 position.*

*95. The compound of claim 87, wherein p is 2, X is —O—, and Y is selected from the group consisting of lower alkoxy, hydroxy, and halogen groups.*

96. The compound of claim 95, wherein Y is a methoxy group.

97. The compound of claim 87, wherein $R_7$ is $—CH_2—CH=CH—CH_2$.

98. The compound of claim 87, wherein R is selected from the group consisting of hydrogen, $C_1—C_3$ alkyl, $C_1—C_3$ alkoxy, hydroxyl, $—COCF_2$, $C_1–C_6$ alkanoyl, Cl, F, Br, I, $C_1–C_3$ alkylamino, $—NO_2$, $—CF_3$, $—OCF_2$, and alkylamino,

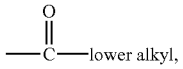

99. A pharmaceutical composition, which comprises a compound as claimed in claim 87, and a pharmaceutically acceptable carrier therefor.

100. An antipsychotic composition which comprises a compond as claimed in claim 87, in an amount sufficient to produce an antipsychotic effect, and a pharmaceutically acceptable carrier therefor.

101. A method of treating psychoses, which comprises administering to a mammal a psychoses-treating effective amount of a compound as claimed in claim 87.

102. An analgesic composition which comprises a compound as claimed in claim 87, in an amount sufficient to produce a pain-relieving effect, and a pharmaceutically acceptable carrier therefor.

103. A method of alleviating pain, which comprises administering to a mammal a pain-relieving effective amount of a compound as claimed in claim 87.

104. A compound of the formula

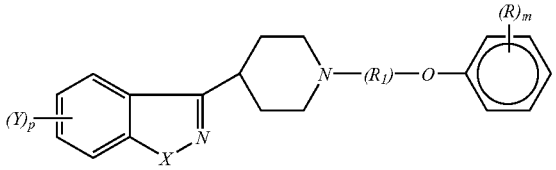

wherein

X is —O— or —S—;

p is 1 or 2;

Y is hydrogen, lower alkyl, hydroxy, chlorine, fluorine, bromine, iodine, lower alkoxy, trifluoromethyl, nitro, or amino, when p is 1;

Y is lower alkoxy, hydroxy, or halogen when p is 2 and X is —O—;

$(R_1)$ is $R_{20}$ or $R_{21}$ in which one or more carbon atoms of $R_{20}$ or $R_{21}$ are substituted by at least one $C_1–C_6$ linear alkyl group, phenyl group or

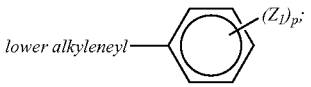

wherein $Z_1$ is lower alkyl, —OH, lower alkoxy, $—CF_3$, $—NO_2$, $—NH_2$, or halogen.

105. The compound of claim 104, wherein the pharmaceutically acceptable addition salt is selected from the group consisting of salts of mineral acids, salts of monobasic carboxylic acids, salts of dibasic carboxylic acids, and salts of tribasic carboxylic acids.

106. The compound of claim 105, wherein said pharmaceutically acceptable addition salts are selected from the group consisting of salts of hydrochloric acid, sulfuric acid, nitric acid, acetic acid, propionic acid, maleic acid, fumaric acid, carboxysuccinic acid, and citric acid.

107. The compound of claim 104, wherein Y is in the 5 position.

108. The compound of claim 104, wherein Y is in the 6 position.

109. The compound of claim 104, wherein Y is selected from the group consisting of hydrogen, chlorine, bromine and fluorine.

110. The compound of claim 109, wherein Y is fluorine.

111. The compound of claim 110, wherein Y is in the 6 position.

112. The compound of claim 104, wherein p is 2, X is —O—, and Y is selected from the group consisting of lower alkoxy, hydroxy and halogen groups.

113. The compound of claim 112, wherein Y is a methoxy group.

114. The compound of claim 104, wherein R is selected from the group consisting of hydrogen, $C_1–C_3$ alkyl, $C_1–C_3$ alkoxy, hydroxyl, $—COCF_3$, $C_1–C_6$ alkanoyl, Cl, F, Br, I, $C_1–C_3$ alkylamino,

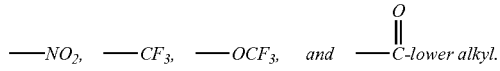

115. A pharmaceutical composition, which comprises a compound as claimed in claim 104, and pharmaceutically acceptable carrier therefor.

116. A antipsychotic composition which comprises a compound as claimed in claim 104, in an amount sufficient to produce an antipsychotic effect, and a pharmaceutically acceptable carrier therefor.

117. A method of treating psychoses, which comprises administering to a mammal a psychoses-treating effective amount of a compound as claimed in claim 104.

118. An analgesic composition which comprises a compound as claimed in claim 104, in an amount sufficient to produce a pain-relieving effect, and a pharmaceutically acceptable carrier therefor.

119. A method of alleviating pain, which comprises administering to a mammal a pain-relieving effective amount of a compound as claimed in claim 104.

120. A compound as claimed in claim 87, with the proviso that when m is 3, R is not —C(=O)-aryl, or —C(=O)-heteroaryl, all geometric, optical and stereoisomers thereof, or a pharmaceutically acceptable acid addition salt thereof.

121. A pharmaceutically composition, which comprises a compound as claimed in claim 120, and a pharmaceutically acceptable carrier therefor.

122. An antipsychotic composition which comprises a compound as claimed in claim 120, in an amount sufficient to produce an antipsychotic effect, and a pharmaceutically acceptable carrier therefor.

123. A method of treating psychoses, which comprises administering to a mammal a psychoses-treating effective amount of a compound as claimed in claim 120.

124. An analgesic composition which comprises a compound as claimed in claim 120, in an amount sufficient to produce a pain-relieving effect, and a pharmaceutically acceptable carrier therefor.

125. A method of alleviating pain, which comprises administering to a mammal a pain-relieving effective amount of a compound as claimed in claim 120.

126. A compound as claimed in claim 104, with the proviso that when m is 3, R is not —C(=O)-aryl, or —C(=O)-heteroaryl, all geometric, optical and stereoisomers thereof, or a pharmaceutically acceptable acid addition salt thereof.

127. A pharmaceutical composition, which comprises a compound as claimed in claim 126, and a pharmaceutically acceptable carrier therefor.

128. An antipsychotic composition which comprises a compound as claimed in claim 126, in an amount sufficient to produce an antipsychotic effect, and a pharmaceutically acceptable carrier therefor.

129. A method of treating psychoses, which comprises administering to a mammal a psychoses-treating effective amount of a compound as claimed in claim 126.

130. An analgesic composition which comprises a compound as claimed in claim 126, in an amount sufficient to produce a pain-relieving effect, and a pharmaceutically acceptable carrier therefor.

131. A method of alleviating pain, which comprises administering to a mammal a pain-relieving effective amount of a compound as claimed in claim 126.

132. A compound of formula

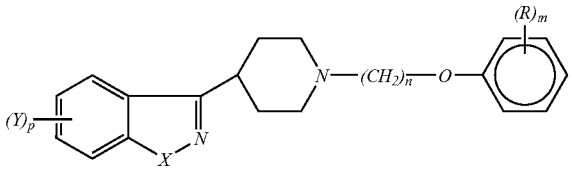

wherein

X is —O— or —S—;

p is 1 or 2;

Y is hydrogen, lower alkyl, hydroxy, chorine, fluorine, bromine, iodine, lower alkoxy, trifluoromethyl, nitro, or amino, when p is 1;

Y is lower alkoxy, hydroxy or halogen when p is 2 and X is —O—;

n is 2, 3, 4 or 5;

R is hydrogen, lower alkyl, lower alkoxy, hydroxyl, carboxyl, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, dialkylaminocarbonyl, formyl, —C(=O)-alkyl, —C(=O)-O-alkyl, —C(=O)-aryl, —C(=O)-heteroaryl, —CH($OR_7$)-alkyl, —C(=W)-alkyl, —C(=W)-aryl, or —C(=W)-heteroaryl;

wherein alkyl is lower alkyl;

aryl is phenyl or

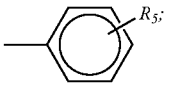

wherein $R_5$ is hydrogen, lower alkyl, lower alkoxy, hydroxy, chlorine, fluorine, bromine, iodine, lower monoalkylamino, nitro, cyano, trifluoromethyl, or trifluoromethoxy;

heteroaryl is

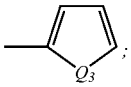

wherein $Q_3$ is —O—, —S—, —NH—, or —CH=N—;

W is $CH_2$ or $CHR_8$ or N—$R_9$;

$R_7$ is hydrogen, lower alkyl, or acyl;

$R_8$ is lower alkyl;

$R_9$ is hydroxy, lower alkoxy, or —$NHR_{10}$; and $R_{10}$ is hydrogen, lower alkyl, $C_1$–$C_3$ acyl, aryl, —C(=O)-aryl or —C(=O)-heteroaryl;

wherein aryl and heteroaryl are as defined above; and m is 1, 2, or 3;

with the proviso that at least one R is selected from the group consisting of dialkylaminocarbonyl, formyl, —C(=W)-alkyl, —C(=W)-aryl, and —C(=W)-heteroaryl;

all geometric, optical and stereoisomers thereof, or a pharmaceutically acceptable acid addition salt thereof.

133. The compound of claim 132, wherein the pharmaceutically acceptable addition salt is selected from the group consisting of salts of mineral acids, salts of monobasic carboxylic acids, salts of dibasic carboxylic acids, and salts of tribasic carboxylic acids.

134. The compound of claim 133, wherein said pharmaceutically acceptable addition salts are selected from the group consisting of salts of hydrochloric acid, sulfuric acid, nitric acid, acetic acid, propionic acid, maleic acid, furmaric acid, carboxysuccinic acid, and citric acid.

135. The compound of claim 132, wherein Y is in the 5 position.

136. The compound of claim 132, wherein Y is in the 6 position.

137. The compound of claim 132, wherein Y is selected from the group consisting of hydrogen, chlorine, bromine and fluorine.

138. The compound of claim 137, wherein Y is fluorine.

139. The compound of claim 138, wherein Y is in the 6 position.

140. The compound of claim 132, wherein p is 2, X is —O—, and Y is selected from the group consisting of lower alkoxy, hydroxy and halogen groups.

141. The compond of claim 140, wherein Y is a methoxy group.

142. The compound of claim 132, wherein one R group is selected from the group consisting of hydrogen, $C_1$–$C_3$ alkyl, $C_1$–$C_3$ alkoxy, hydroxyl, —$COCF_3$, $C_1$–$C_6$ alkanoyl, Cl, F, Br,I, $C_1$–$C_3$ alkylamino, —$NO_2$, —$CF_3$, —$OCF_3$, and —$\overset{O}{\overset{\|}{C}}$-lower alkyl.

143. A pharmaceutical composition, which comprises a compound as claimed in claim 132, and a pharmaceutical acceptable carrier therefor.

144. An antipsychotic composition which comprises a compound as claimed in claim 132, in an amount sufficient

*to produce an antipsychotic effect, and a pharmaceutically acceptable carrier therefor.*

*145. A method of treating psychoses, which comprises administering to a mammal a psychoses-treating effective amount of a compound as claimed in claim 132.*

*146. An analgesic composition which comprises a compound as claimed in claim 132, in an amount sufficient to produce a pain-relieving effect, and a pharmaceutically acceptable carrier therefor.*

*147. A method of alleviating pain, which comprises administering to a mammal a pain-relieving effective amount of a compound as claimed in claim 132.*

* * * * *